(12) United States Patent
Eliuk et al.

(10) Patent No.: US 8,386,070 B2
(45) Date of Patent: Feb. 26, 2013

(54) AUTOMATED PHARMACY ADMIXTURE SYSTEM

(75) Inventors: Walter W. Eliuk, Winnipeg (CA);
Ronald H. Rob, Dugald (CA); Lance R. Mlodzinski, Winnipeg (CA); Alex H. Reinhardt, St. Andrews (CA); Thom Doherty, Winipeg (CA); Dustin Deck, St. Andrews (CA)

(73) Assignee: Intelligent Hospital Systems, Ltd, Winnipeg (CA)

( * ) Notice: Subject to any disclaimer, the term of this patent is extended or adjusted under 35 U.S.C. 154(b) by 691 days.

(21) Appl. No.: 12/628,884

(22) Filed: Dec. 1, 2009

(65) Prior Publication Data

US 2010/0241270 A1   Sep. 23, 2010

Related U.S. Application Data

(60) Provisional application No. 61/161,381, filed on Mar. 18, 2009, provisional application No. 61/254,625, filed on Oct. 23, 2009.

(51) Int. Cl.
*B65B 3/00* (2006.01)

(52) U.S. Cl. ........ 700/214; 700/213; 700/228; 700/231; 141/1; 141/114; 141/130; 221/197; 221/191

(58) Field of Classification Search .................. 700/213, 700/214, 228, 231, 90; 141/1, 114, 130; 221/191, 197, 198
See application file for complete search history.

(56) References Cited

U.S. PATENT DOCUMENTS

| | | | |
|---|---|---|---|
| 2,988,984 A | 6/1961 | Eckert et al. | |
| 3,002,387 A | 10/1961 | Micheletti | |
| 3,556,342 A | 1/1971 | Guarr | |
| 3,878,967 A | 4/1975 | Joslin et al. | |
| 3,880,211 A | 4/1975 | Gess et al. | |
| 3,965,945 A | 6/1976 | Ross | |
| 4,058,121 A | 11/1977 | Choksi et al. | |
| 4,372,464 A | 2/1983 | Otten | |
| 4,464,336 A | 8/1984 | Hiramoto | |
| 4,634,424 A | 1/1987 | O'Boyle | |
| 4,648,430 A | 3/1987 | Di Gianfilippo et al. | |

(Continued)

FOREIGN PATENT DOCUMENTS

| CA | 1317262 | 9/1989 |
|---|---|---|
| DE | 4314657 | 11/1994 |

(Continued)

OTHER PUBLICATIONS

"Aseptic Technique Process and End-product Evaluation," Department of Pharmacy Policy, 1994, University of Kentucky Hospital, Chandler Medical Center, 4 pages.

(Continued)

*Primary Examiner* — Patrick Mackey
(74) *Attorney, Agent, or Firm* — Oblon, Spivak, McClelland, Maier & Neustadt, L.L.P.

(57) ABSTRACT

In a preferred implementation, an automated pharmacy admixture system (APAS) prepares intermediary IV bags as drug sources for creating highly diluted patient doses in syringes. During the compounding process the APAS may align needles with a vial seal opening so as to ensure repeated entry through the same vial puncture site via precise control of needle position, needle bevel orientation, and needle entry speed. These techniques can in certain implementations substantially improve bung pressure sealing and reduced particulate generation. The APAS optionally creates drug order queues for incoming drug orders wherein the orders can be sorted by priority, drug type or patient location. A phantom queue can be combined with the incoming drug order queues to include frequently used medicaments to minimize operator loading of the APAS.

26 Claims, 45 Drawing Sheets

U.S. PATENT DOCUMENTS

| | | |
|---|---|---|
| 4,669,599 A | 6/1987 | Dijkmeijer et al. |
| 4,699,186 A | 10/1987 | Palin et al. |
| 4,706,207 A | 11/1987 | Hennessy et al. |
| 4,730,435 A | 3/1988 | Riddle et al. |
| 4,811,764 A | 3/1989 | McLaughlin |
| 4,829,524 A | 5/1989 | Yoshida |
| 4,835,372 A | 5/1989 | Gombrich et al. |
| 4,835,707 A | 5/1989 | Amano et al. |
| 4,842,028 A | 6/1989 | Kaufman et al. |
| 4,847,764 A | 7/1989 | Halvorson |
| 4,861,335 A | 8/1989 | Reynolds |
| 4,871,559 A | 10/1989 | Dunn et al. |
| 4,878,705 A | 11/1989 | Arnquist |
| 4,910,942 A | 3/1990 | Dunn et al. |
| 4,918,604 A | 4/1990 | Baum |
| 4,993,598 A | 2/1991 | Groninger |
| 5,004,962 A | 4/1991 | Fonss et al. |
| 5,020,958 A | 6/1991 | Tuttobene |
| 5,034,235 A | 7/1991 | Dunn et al. |
| 5,122,342 A | 6/1992 | McCulloch et al. |
| 5,144,146 A | 9/1992 | Wekhof |
| 5,169,642 A | 12/1992 | Brinker et al. |
| 5,203,385 A | 4/1993 | Waber |
| 5,208,762 A | 5/1993 | Charhut et al. |
| 5,229,074 A | 7/1993 | Heath et al. |
| 5,267,174 A | 11/1993 | Kaufman et al. |
| 5,288,285 A | 2/1994 | Carter |
| 5,309,959 A | 5/1994 | Shaw et al. |
| 5,319,543 A | 6/1994 | Wilhelm |
| 5,324,519 A | 6/1994 | Dunn et al. |
| 5,337,919 A | 8/1994 | Spaulding et al. |
| 5,339,421 A | 8/1994 | Housel, III |
| 5,341,854 A * | 8/1994 | Zezulka et al. ................ 141/1 |
| 5,348,585 A | 9/1994 | Weston |
| 5,363,885 A | 11/1994 | McConnell et al. |
| 5,366,896 A * | 11/1994 | Margrey et al. ............. 436/48 |
| 5,411,489 A | 5/1995 | Pagay et al. |
| 5,431,201 A | 7/1995 | Torchia et al. |
| 5,451,528 A | 9/1995 | Raymoure et al. |
| 5,479,969 A | 1/1996 | Hardie et al. |
| 5,502,944 A | 4/1996 | Kraft et al. |
| 5,522,512 A | 6/1996 | Archer et al. |
| 5,522,804 A | 6/1996 | Lynn |
| 5,533,606 A | 7/1996 | Yuyama |
| 5,534,222 A | 7/1996 | Kelbrick et al. |
| 5,573,042 A | 11/1996 | De Haen |
| 5,597,995 A | 1/1997 | Williams et al. |
| 5,611,051 A | 3/1997 | Pirelli |
| 5,635,394 A | 6/1997 | Horn |
| 5,660,305 A | 8/1997 | Lasher et al. |
| 5,666,410 A | 9/1997 | McLane |
| 5,680,858 A | 10/1997 | Hansen et al. |
| 5,700,998 A | 12/1997 | Palti |
| 5,713,485 A | 2/1998 | Liff et al. |
| 5,713,487 A | 2/1998 | Coughlin |
| 5,744,094 A | 4/1998 | Castberg et al. |
| 5,768,853 A | 6/1998 | Bushnell et al. |
| 5,769,086 A | 6/1998 | Ritchart et al. |
| 5,786,598 A | 7/1998 | Clark et al. |
| 5,797,515 A | 8/1998 | Liff et al. |
| 5,798,020 A | 8/1998 | Coughlin |
| 5,805,454 A | 9/1998 | Valerino, Sr. et al. |
| 5,812,410 A | 9/1998 | Lion et al. |
| 5,832,447 A | 11/1998 | Riekr et al. |
| 5,839,836 A | 11/1998 | Yuyama et al. |
| 5,848,593 A | 12/1998 | McGrady et al. |
| 5,884,273 A | 3/1999 | Sattizahn et al. |
| 5,884,457 A | 3/1999 | Ortiz et al. |
| 5,895,019 A | 4/1999 | Ibarra |
| 5,900,211 A | 5/1999 | Dunn et al. |
| 5,907,493 A | 5/1999 | Boyer et al. |
| 5,911,252 A | 6/1999 | Cassel |
| 5,912,818 A | 6/1999 | McGrady et al. |
| 5,948,360 A | 9/1999 | Rao et al. |
| 5,963,641 A | 10/1999 | Crandall et al. |
| 5,971,593 A | 10/1999 | McGrady |
| 5,993,046 A | 11/1999 | McGrady et al. |
| 6,006,946 A | 12/1999 | Williams et al. |
| 6,013,918 A | 1/2000 | Bushnell et al. |
| 6,037,598 A | 3/2000 | Cicha |
| 6,048,086 A * | 4/2000 | Valerino, Sr. ................ 706/10 |
| 6,060,022 A | 5/2000 | Pang et al. |
| 6,068,156 A | 5/2000 | Liff et al. |
| 6,082,987 A | 7/2000 | Su et al. |
| 6,096,561 A | 8/2000 | Tayi |
| 6,108,588 A | 8/2000 | McGrady |
| 6,141,412 A | 10/2000 | Smith et al. |
| 6,155,485 A | 12/2000 | Coughlin et al. |
| 6,161,141 A | 12/2000 | Dillon |
| 6,181,979 B1 | 1/2001 | Murakami |
| 6,181,982 B1 | 1/2001 | Yuyama et al. |
| 6,200,289 B1 | 3/2001 | Hochman et al. |
| 6,202,004 B1 | 3/2001 | Valerino |
| 6,202,923 B1 | 3/2001 | Boyer et al. |
| 6,203,535 B1 | 3/2001 | Barney et al. |
| 6,249,717 B1 | 6/2001 | Nicholson et al. |
| 6,249,774 B1 | 6/2001 | Roden et al. |
| 6,279,724 B1 | 8/2001 | Davis |
| 6,318,630 B1 | 11/2001 | Coughlin et al. |
| 6,343,690 B1 | 2/2002 | Britton et al. |
| 6,355,024 B1 | 3/2002 | Small et al. |
| 6,360,794 B1 | 3/2002 | Turner |
| 6,370,841 B1 | 4/2002 | Chudy et al. |
| RE37,829 E | 9/2002 | Charhut et al. |
| 6,461,568 B1 | 10/2002 | Eckhardt |
| 6,470,234 B1 | 10/2002 | McGrady |
| 6,477,442 B1 | 11/2002 | Valerino |
| 6,564,121 B1 | 5/2003 | Wallace et al. |
| 6,566,659 B1 | 5/2003 | Clark et al. |
| 6,592,816 B1 | 7/2003 | Ebel et al. |
| 6,599,476 B1 | 7/2003 | Watson et al. |
| 6,604,903 B2 | 8/2003 | Osborne et al. |
| 6,616,771 B2 | 9/2003 | Osborne et al. |
| 6,623,455 B2 | 9/2003 | Small et al. |
| 6,673,048 B1 | 1/2004 | Duchon et al. |
| 6,722,404 B2 | 4/2004 | Osborne |
| 6,735,497 B2 | 5/2004 | Wallace et al. |
| 6,832,844 B2 | 12/2004 | Guzorek |
| 6,847,861 B2 | 1/2005 | Lunak et al. |
| 6,877,530 B2 * | 4/2005 | Osborne et al. ................ 141/27 |
| 6,883,681 B1 | 4/2005 | Coughlin et al. |
| 6,915,823 B2 | 7/2005 | Osborne et al. |
| 6,975,924 B2 | 12/2005 | Kircher et al. |
| 6,976,349 B2 | 12/2005 | Baldwin et al. |
| 6,985,870 B2 | 1/2006 | Martucci et al. |
| 6,986,234 B2 | 1/2006 | Liedtke |
| 6,991,002 B2 | 1/2006 | Osborne et al. |
| 7,007,443 B2 | 3/2006 | Liedtke et al. |
| 7,017,622 B2 * | 3/2006 | Osborne et al. ................ 141/27 |
| 7,100,792 B2 | 9/2006 | Hunter et al. |
| 7,108,679 B2 | 9/2006 | Alchas |
| 7,117,902 B2 * | 10/2006 | Osborne ................ 141/27 |
| 7,240,699 B2 * | 7/2007 | Osborne et al. ................ 141/27 |
| 7,260,447 B2 * | 8/2007 | Osborne ................ 700/216 |
| 7,278,813 B2 | 10/2007 | Davis et al. |
| 7,403,901 B1 | 7/2008 | Carley et al. |
| 7,630,788 B1 | 12/2009 | Reese |
| 7,783,383 B2 * | 8/2010 | Eliuk et al. ................ 700/245 |
| 7,930,066 B2 * | 4/2011 | Eliuk et al. ................ 700/245 |
| 2001/0018937 A1 | 9/2001 | Nemoto |
| 2002/0020459 A1 | 2/2002 | Baldwin et al. |
| 2002/0035412 A1 | 3/2002 | Kircher et al. |
| 2002/0146343 A1 | 10/2002 | Jenkins et al. |
| 2002/0198738 A1 | 12/2002 | Osborne |
| 2003/0046114 A1 | 3/2003 | Davies et al. |
| 2003/0097368 A1 | 5/2003 | Tribble et al. |
| 2003/0216831 A1 | 11/2003 | Hart et al. |
| 2004/0028553 A1 | 2/2004 | Panico |
| 2004/0034447 A1 | 2/2004 | Vollm |
| 2004/0099869 A1 | 5/2004 | Gaska et al. |
| 2004/0104243 A1 | 6/2004 | Osborne et al. |
| 2004/0123567 A1 | 7/2004 | McErlean et al. |
| 2004/0154690 A1 | 8/2004 | Osborne et al. |
| 2004/0193317 A1 | 9/2004 | Lunak et al. |
| 2004/0241041 A1 * | 12/2004 | Woodworth et al. ............ 422/22 |
| 2004/0249498 A1 | 12/2004 | William et al. |
| 2004/0250842 A1 | 12/2004 | Adams et al. |

| | | | |
|---|---|---|---|
| 2005/0045242 | A1 | 3/2005 | Osborne |
| 2005/0133729 | A1 | 6/2005 | Woodworth et al. |
| 2005/0224137 | A1 | 10/2005 | Tribble et al. |
| 2005/0236579 | A1 | 10/2005 | Jenkins et al. |
| 2005/0252572 | A1 | 11/2005 | Khan et al. |
| 2005/0252574 | A1 | 11/2005 | Khan et al. |
| 2005/0279419 | A1 | 12/2005 | Tribble et al. |
| 2006/0136095 | A1 | 6/2006 | Rob et al. |
| 2006/0224414 | A1 | 10/2006 | Astrup et al. |
| 2006/0225383 | A1 | 10/2006 | Cobb et al. |
| 2006/0259195 | A1 | 11/2006 | Eliuk et al. |
| 2008/0114328 | A1 | 5/2008 | Doherty |
| 2008/0199353 | A1 | 8/2008 | Mlodzinski et al. |
| 2009/0067973 | A1 | 3/2009 | Eliuk et al. |
| 2009/0126825 | A1 | 5/2009 | Eliuk et al. |
| 2009/0138340 | A1 | 5/2009 | Borr et al. |
| 2010/0017031 | A1 | 1/2010 | Rob et al. |

FOREIGN PATENT DOCUMENTS

| | | |
|---|---|---|
| IT | 1316152 | 12/2000 |
| WO | WO 90/09776 | 9/1990 |
| WO | WO 94/04415 | 3/1994 |
| WO | WO 95/15142 | 6/1995 |
| WO | WO 97/43915 | 11/1997 |
| WO | WO 99/29412 | 6/1999 |
| WO | WO 99/29415 | 6/1999 |
| WO | WO 99/29467 | 6/1999 |
| WO | WO 00/16213 | 3/2000 |
| WO | WO 2006/069361 | 6/2006 |
| WO | WO 2006/124211 | 11/2006 |
| WO | WO 2008/058280 | 5/2008 |
| WO | WO 2008/101353 | 8/2008 |
| WO | WO 2009/033283 | 3/2009 |
| WO | WO 2009/062316 | 5/2009 |

OTHER PUBLICATIONS

"Basic Definitions and Data for Electron Beam Sterilization," by Dr. Alex Wekhof, SteriBeam Systems, GmbH, 2005.
"BD Helping all people live health lives Prefilled. Proven. Preferred.," BD Product Literature, BD, 2000.
"Disinfection with Flash Lamps," by A. Wekhof, PDA Journal of Pharmaceutical Science & Technology, vol. 54, No. 3, May/Jun. 2000.
"Does the Engineering of the PureBright Sterilisation System Match the Pulsed Light Sterilisation Process?," by Dr. Alex Wekhof, Advanced Ultra-Fast Sterilisaton from SteriBeam Systems GmbH, Kehl, Germany, http://www.steribeam.com/articles/WTPP-Rep/html, 2001.
Industrial Automated Pulsed UV Modules, Advanced Pulsed UV and Corona Systems from SteriBeam GmbH, Kehl, Germany, http://www.steribeam.com/f-scale.puv, Printed Jan. 25, 2008.
"Pulsed UV Disintegration (PUVD): a new sterilization mechanism for packaging and broad medical-hospital applications," by Dr. Alex Wekhof, Dipl-Phys. Franz-Josef Trompeter, Dipl.-Ing. Oliver Franken, The First International Conference on Ultraviolet Technologies, Jun. 14-16, 2001, Washington, D.C.
Robotic system for i.v. antineoplastic drug preparation: Description and preliminary evaluation under simulated conditions by Dennis D. Cote and Mark G. Torchia, American Journal of Hospital Pharmacy, vol. 46, Nov. 1989.
"Two UV-flashlamps R&D/Labor Automated System," Advanced Pulsed UV and Corona Systems From SteriBeam GmbH, Kehl, Germany, http://www.steribeam.com/xe-labor-wt.html, printed Mar. 24, 2006.
Biomedical Technology Consulting, "05BTC—Cytocare: Automatic system for the preparation of cytostatic drugs," pp. 1-22 with translation; downloaded from Internet site www.tecnomedical.com on Aug. 14, 2006.
"Welcome to the Future. The Robotic IV Admixture System: The established wave of the future with real bottom line savings." Robotic IV Admixture System; Canada, 1992.
"Dose Systems." Pharmaceutical Journal; pp. 757, vol. 254, No. 6843; Jun. 3, 1995.
International Search Report and Written Opinion, PCT/CA2008/001613 dated Sep. 12, 2008, 10 pages.
International Search Report and Written Opinion, PCT/US2006/15731 dated Jul. 29, 2008, 10 pages.
International Search Report and Written Opinion, PCT/US2007/84332 dated Jul. 1, 2008, 11 pages.
International Search Report and Written Opinion, PCT/US2005/046978 dated Aug. 2, 2006, 16 pages.
International Search Report and Written Opinion, PCT/CA2008/002027 dated Feb. 25, 2009, 12 pages.
Definition of "cannula", Webster's Third New International Dictionary, Unabridged. Copyright 1993 Merriam-Webster, Incorporated.
Kohler, et al. "Standardizing the expression and nomenclature of cancer treatment regiments,", Am J Health-Svst Pharm: 1998; 55: 137-144.
Office Action in Re Exam Control No. 95/000,333; mailed Mar. 7, 2008; 36 pages.
Office Action in Re Exam Control No. 95/000,333; mailed May 5, 2009; 43 pages.
Office Action in Re Exam Control No. 95/000,334; mailed Feb. 27, 2008; 17 pages.
Office Action in Re Exam Control No. 95/000,335; mailed Mar. 7, 2008; 16 pages.
Office Action in Re Exam Control No. 95/000,336; mailed Mar. 11, 2008; 36 pages.
Office Action in Re Exam Control No. 95/000,336; mailed Oct. 15, 2008; 21 pages.
Office Action in Re Exam Control No. 95/000,340; mailed Mar. 21, 2008; 41 pages.
Office Action in Re Exam Control No. 95/000,340; mailed Mar. 30, 2009; 69 pages.
Office Action in Re Exam Control No. 95/000,342; mailed Mar. 11, 2008; 18 pages.
Office Action in Re Exam Control No. 95/000,342; mailed Oct. 15, 2008; 28 pages.
Office Action in Re Exam Control No. 95/000,345; mailed Apr. 23, 2008; 32 pages.
Office Action in Re Exam Control No. 95/000,345; mailed Mar. 30, 2009; 67 pages.
Patent Owner's Response in Re Exam Control No. 95/000,333; filed Jun. 12, 2008, 11 pages.
Patent Owner's Response in Re Exam Control No. 95/000,333; filed Jun. 7, 2008, 37 pages.
Patent Owner's Response in Re Exam Control No. 95/000,333; filed Jun. 16, 2009, 16 pages.
Patent Owner's Response in Re Exam Control No. 95/000,335; filed Jun. 7, 2008, 33 pages.
Patent Owner's Response in Re Exam Control No. 95/000,336; filed Nov. 14, 2008, 35 pages.
Patent Owner's Response in Re Exam Control No. 95/000,336; filed Jun. 12, 2008, 13 pages.
Patent Owner's Response in Re Exam Control No. 95/000,336; filed Jun. 7, 2008, 43 pages.
Patent Owner's Response in Re Exam Control No. 95/000,340; filed Jun. 12, 2008, 10 pages.
Patent Owner's Response in Re Exam Control No. 95/000,340; filed May 20, 2008, 33 pages.
Patent Owner's Response in Re Exam Control No. 95/000,342; filed Jun. 7, 2008,32 pages.
Patent Owner's Response in Re Exam Control No. 95/000,342; filed Nov. 13, 2008, 14 pages.
Patent Owner's Response in Re Exam Control No. 95/000,345; filed Jun. 23, 2008, 32 pages.
Patent Owner's Response in Re Exam Control No. 95/000,345; filed Apr. 29, 2009, 8 pages.
Request for InterPartes Reexamination in Reexam Control No. 95/000,333; filed Jan. 11, 2008; 26 pages.
Request for InterPartes Reexamination in Reexam Control No. 95/000,334; filed Jan. 11, 2008; 54 pages.
Request for InterPartes Reexamination in Reexam Control No. 95/000,335; filed Jan. 11, 2008; 73 pages.
Request for InterPartes Reexamination in Reexam Control No. 95/000,336; filed Jan. 11, 2008; 97 pages.
Request for InterPartes Reexamination in Reexam Control No. 95/000,340; filed Jan. 30, 2008; 33 pages.

Request for InterPartes Reexamination in Reexam Control No. 95/000,342; filed Feb. 1, 2008; 27 pages.
Request for InterPartes Reexamination in Reexam Control No. 95/000,345; filed Feb. 11, 2008; 32 pages.
Third Party Comments on Patent Owner Response in Reexam Control No. 95/000,333; filed Jul. 7, 2008; 29 pages.
Third Party Comments on Patent Owner Response in Reexam Control No. 95/000,335; filed Jul. 7, 2008; 18 pages.
Third Party Comments on Patent Owner Response in Reexam Control No. 95/000,336; filed Dec. 15, 2008; 7 pages.
Third Party Comments on Patent Owner Response in Reexam Control No. 95/000,336; filed Jul. 7, 2008; 15 pages.
Third Party Comments on Patent Owner Response in Reexam Control No. 95/000,340; filed Jun. 19, 2008; 19 pages.
Third Party Comments on Patent Owner Response in Reexam Control No. 95/000,342; filed Dec. 15, 2008; 7 pages.
Third Party Comments on Patent Owner Response in Reexam Control No. 95/000,342; filed Jul. 7, 2008; 28 pages.
Third Party Comments on Patent Owner Response in Reexam Control No. 95/000,345; filed Jul. 23, 2008; 16 pages.
Third Party Comments on Patent Owner Response in Reexam Control No. 95/000,333; filed Jul. 16, 2009; 11 pages.
Office Action in Re Exam Control No. 95/000,345; mailed Jul. 2, 2009 73 pages.
Office Action in Re Exam Control No. 95/000,340; mailed Jul. 20, 2009, 8 pages.
EPO Extended European Search Report for EP Application No. 06751430.7 (PCT/US2006/015731), mailed Sep. 14, 2009, 7 pages.
Office Action in Re Exam Control No. 95/000,335; mailed Oct. 1, 2009 27 pages.
Re Exam Notification re Brief, Control No. 95/000,334; mailed Sep. 29, 2009 7 pages.
Re Exam Right of Appeal Notice, Control No. 95/000,333; mailed Dec. 2, 2009, 30 pages.
International Preliminary Report on Patentabililty, PCT/CA2008/000348, dated Sep. 3, 2009, 10 pages.
International Search Report and Written Opinion, PCT/CA2008/000348 dated Jun. 3, 2008, 10 pages.
Office Action in U.S. Appl. No. 11/316,795 notification date Dec. 29, 2008, 16 pages.
Office Action in U.S. Appl. No. 11/389,995 notification date Apr. 28, 2009, 8 pages.
Patent Owner's Entry in Reexam Control No. 95/000,333; filed Jan. 22, 2010; 32 pages.
Interview Summary in U.S. Appl. No. 11/316,795 notification date Feb. 24, 2009; 4 pages.
Reply to office action in U.S. Appl. No. 11/316,795 notification date Mar. 27, 2009; 14 pages.
Notice of Allowance in U.S. Appl. No. 11/316,795 mailing date Jun. 22, 2009; 6 pages.
Interview Summary in U.S. Appl. No. 11/389,995 notification date Jun. 17, 2009; 4 pages.
Reply to office action in U.S. Appl. No. 11/389,995 notification date Sep. 15, 2009; 14 pages.
Express Withdrawal of Appeal in Reexam control No. 95000334; filed Oct. 29, 2009; 4 pages.
Patent Owner Petition in Reexam control No. 95/000334; filed Nov. 10, 2009; 8 pages.
Reply to Office Action in European Application serial No. 05855521.0, filed Jan. 8, 2010, pp. 15.
PCT/CA2010/000073 Written Opinion of International Searching Authority issued Mar. 11, 2010, 3 pages.

\* cited by examiner

| Bag size (ml) | Min (ml) | Max (ml) |
|---|---|---|
| 50 | 25 | 65 |
| 100 | 50 | 136 |
| 150 | 75 | 195 |
| 250 | 125 | 325 |
| 500 | 250 | 600 |
| 1000 | 500 | 1100 |

FIG. 3

| | | | |
|---|---|---|---|
| 802 | A | Syringe Type | 4 |
| 804 | B | Percentage of Syringe Nominal Volume | 0.1 |
| 806 | C | Error Tolerance for Fluid Adjust with Reweigh | 0.04 |
| 808 | D | Error Tolerance for Fluid Adjust without Reweigh | 0.08 |

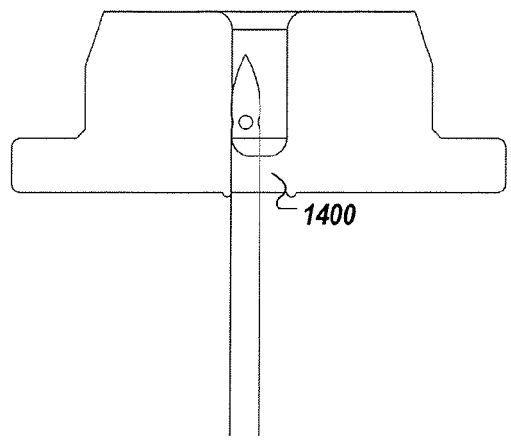
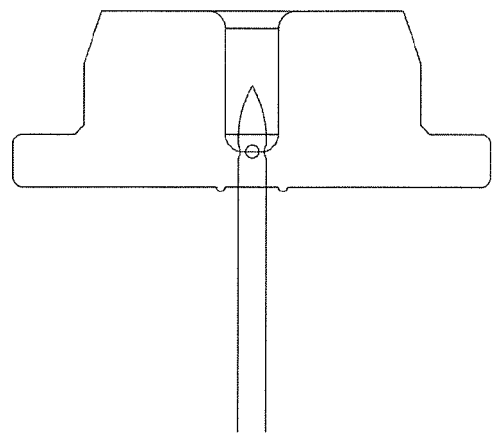
FIG. 14  FIG. 15
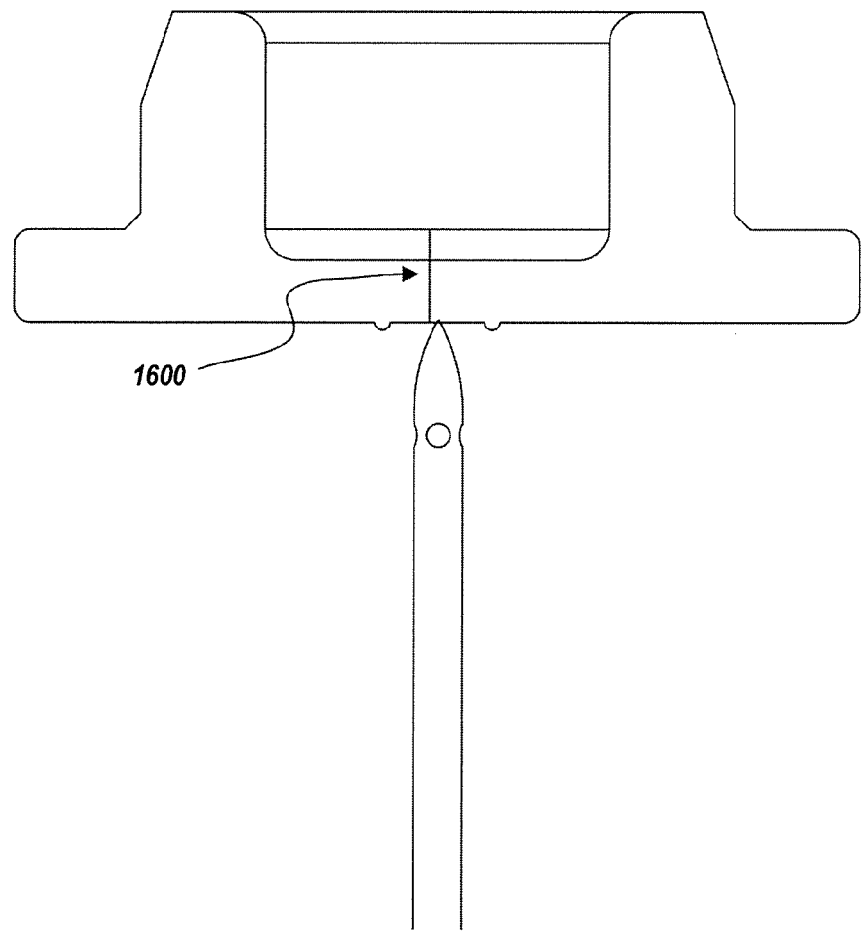
FIG. 16

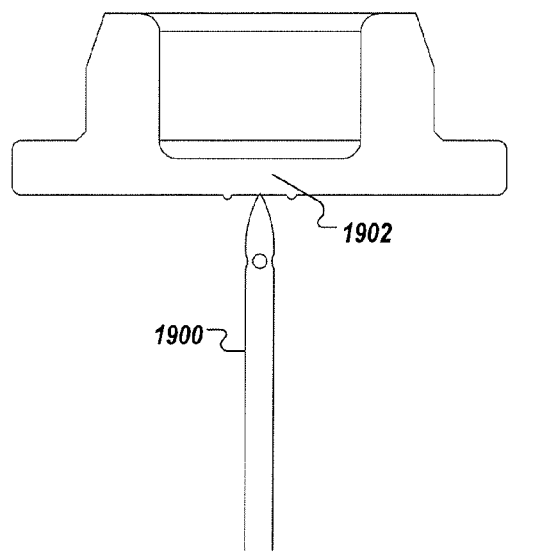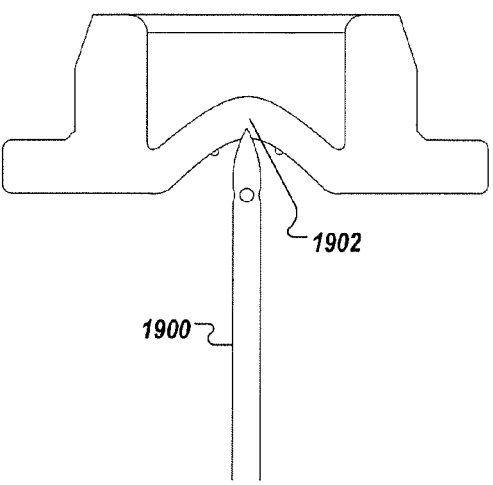
FIG. 19AFIG. 19B
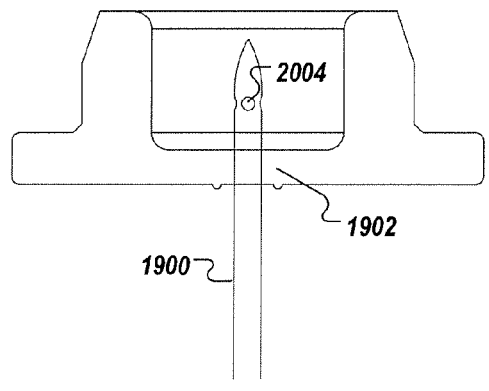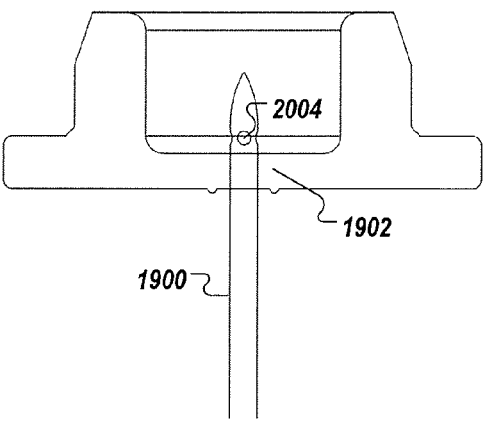
FIG. 20AFIG. 20B

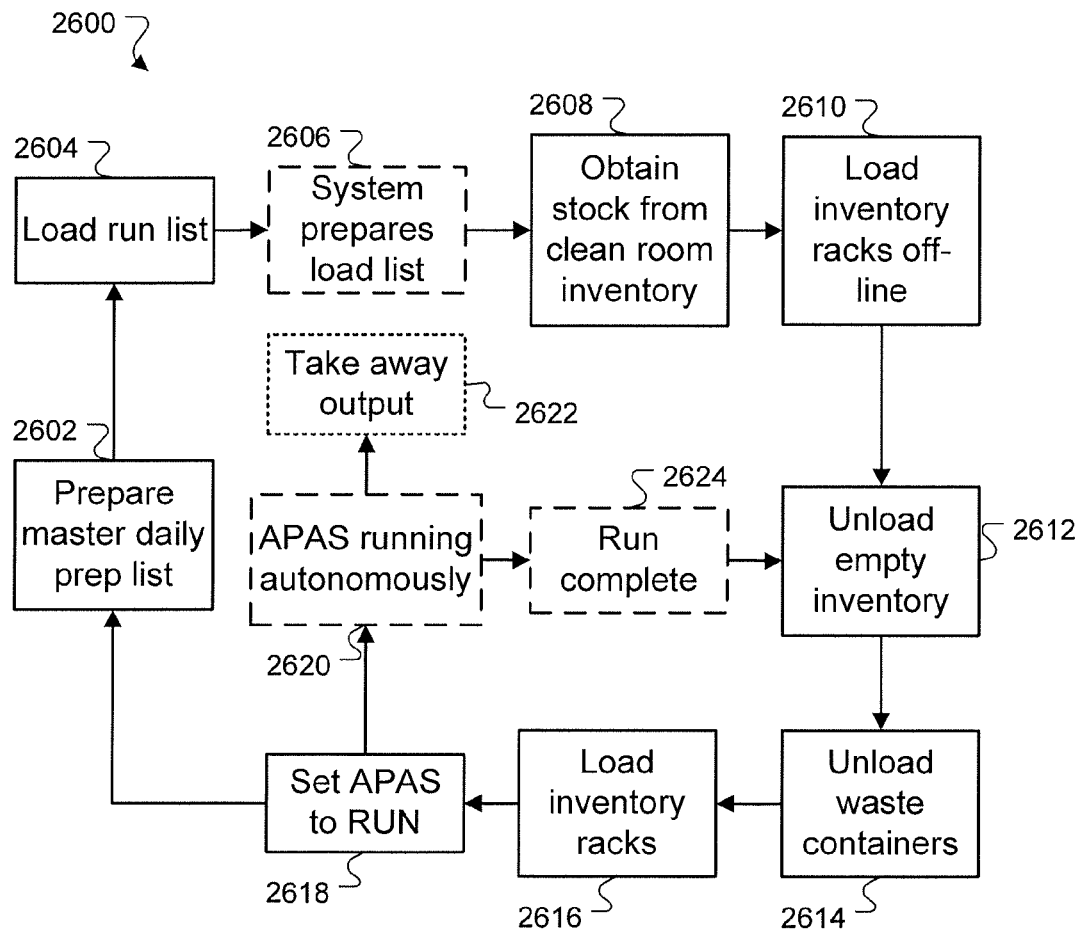
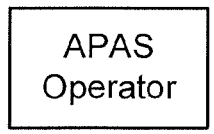 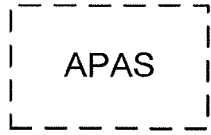 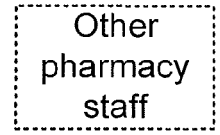
FIG. 26

AUTOMATED PHARMACY ADMIXTURE SYSTEM

CROSS REFERENCE TO RELATED APPLICATIONS

This application claims priority under 35 U.S.C. §119(e) to U.S. Provisional Patent Application Ser. No. 61/254,625, entitled "Method And Apparatus For Intermediate IV Bag Handling", and filed by Eliuk et al. on Oct. 23, 2009; and to U.S. Provisional Patent Application Ser. No. 61/161,381, entitled "Vial Seal Puncturing," and filed by Mlodzinski et al. on Mar. 18, 2009, the entire disclosures of which are incorporated herein by reference.

This application also claims the benefit of the currently pending U.S. patent application Ser. No. 12/271,828, entitled "Method And Apparatus For Automated Fluid Transfer Operations," and filed by Eliuk et al. on Nov. 14, 2008; U.S. patent application Ser. No. 12/209,097, entitled "Gripper Device," and filed by Eliuk et al. on Sep. 11, 2008; U.S. patent application Ser. No. 12/035,850, entitled "Ultraviolet Sanitization in Pharmacy Environments," and filed by Reinhardt et al. on Feb. 22, 2008; U.S. patent application Ser. No. 11/937,846, entitled "Control of Fluid Transfer Operations," and filed by Doherty et al. on Nov. 9, 2007; and U.S. patent application Ser. No. 11/389,995, entitled "Automated Pharmacy Admixture System," and filed by Eliuk et al. on Mar. 27, 2006, the entire disclosures of which are incorporated by reference.

This application also incorporates herein the entire disclosure by reference: U.S. Pat. No. 7,610,115, entitled "Automated Pharmacy Admixture System (APAS)," and filed by Rob et al. on Dec. 22, 2005.

The entire disclosure of each of the following documents is incorporated by reference herein: U.S. Provisional Patent Application Ser. No. 60/971,815, entitled "Gripper Device," and filed by Eliuk et al. on Sep. 12, 2007; U.S. Provisional Patent Application Ser. No. 60/891,433, entitled "Ultraviolet Disinfection in Pharmacy Environments," and filed by Mlodzinski et al. on Feb. 23, 2007; U.S. Provisional Patent Application Ser. No. 60/865,105, entitled "Control of Needles for Fluid Transfer," and filed by Doherty et al. on Nov. 9, 2006; U.S. Provisional Application Ser. No. 60/681,405, entitled "Device and Method for Cleaning and Needle/Cap Removal in Automated Pharmacy Admixture System," and filed by Rob et al. on May 16, 2005; U.S. Provisional Application Ser. No. 60/638,776, entitled "Automated Pharmacy Admixture System," and filed on Dec. 22, 2004; U.S. patent application Ser. No. 12/271,828, entitled "Method And Apparatus For Automated Fluid Transfer Operations," and filed by Eliuk et al. on Nov. 14, 2008; U.S. patent application Ser. No. 12/209,097, entitled "Gripper Device," and filed by Eliuk et al. on Sep. 11, 2008; U.S. patent application Ser. No. 12/035,850, entitled "Ultraviolet Sanitization in Pharmacy Environments," and filed by Reinhardt et al. on Feb. 22, 2008; U.S. patent application Ser. No. 11/937,846, entitled "Control of Fluid Transfer Operations," and filed by Doherty et al. on Nov. 9, 2007; U.S. patent application Ser. No. 11/389,995, entitled "Automated Pharmacy Admixture System," and filed by Eliuk et al. on Mar. 27, 2006; and U.S. patent application Ser. No. 11/316,795, entitled "Automated Pharmacy Admixture System," and filed by Rob et al. on Dec. 22, 2005.

BACKGROUND

Many medications can be delivered to a patient from an intravenous (IV) bag into which a quantity of a medication is introduced. Sometimes, the medication may be an admixture with a diluent. In some implementations, the IV bag contains the medication and diluent. In some implementations, the IV bag may also contain a carrier or other material to be infused into the patient simultaneously with the medication. Medication can also be delivered to a patient using a syringe.

Additionally, medication can be supplied in dry (e.g., powder) form in a medication container such as a vial. A diluent liquid in a separate or diluent container or vial may be supplied for reconstituting with the medication. The resulting medication may then be delivered to a patient according to the prescription.

One function of the pharmacist can be to prepare a dispensing container, such as an IV bag or a syringe, which contains a proper amount of diluent and medication according to the prescription for that patient. Some prescriptions (e.g., insulin) may be prepared to suit a large number of certain types of patients (e.g., diabetics). In some implementations, a number of similar IV bags containing similar medication can be prepared in a batch, although volumes of each dose may vary. Other prescriptions, such as those involving chemotherapy drugs, may call for very accurate and careful control of diluent and medication to satisfy a prescription that is tailored to the needs of an individual patient.

The preparation of a prescription in a syringe or an IV bag may involve, for example, transferring fluids, such as medication or diluent, among vials, syringes, and/or IV bags. IV bags can be flexible, and may readily change shape as the volume of fluid they contain changes. IV bags, vials, and syringes can be commercially available in a range of sizes, shapes, and designs.

SUMMARY OF SELECTED IMPLEMENTATIONS

In a preferred implementation, an automated pharmacy admixture system (APAS) prepares intermediary IV bags as drug sources for creating highly diluted patient doses in syringes. During the compounding process the APAS may align needles with a vial seal opening so as to ensure repeated entry through the same vial puncture site via precise control of needle position, needle bevel orientation, and needle entry speed. These techniques can in certain implementations substantially improve bung pressure sealing and reduced particulate generation. The APAS optionally creates drug order queues for incoming drug orders wherein the orders can be sorted by priority, drug type or patient location. A phantom queue can be combined with the incoming drug order queues to include frequently used medicaments to minimize operator loading of the APAS. The APAS can include an automated error recovery protocol that recovers from faults encountered during medicament preparation by reusing or discarding containers and doses, dependent on the error encountered, and by requeuing the medicament order for subsequent preparation. The APAS optionally sorts medical waste for disposal from the system into a plurality of medical waste bins for vials, syringes and unused liquids. In selected implementations, the APAS can include a plurality of output chutes that include one or more sensors to determine if the prepared dose has been successfully outputted from the APAS. The APAS robot may be configured to translate a syringe between substations in the APAS in such a way as to avoid dripping the contents of the syringe on any surfaces passed over during the movement in order to avoid cross-contamination. The robot may also be configured to follow specialized vial release protocols to counteract unintended adhesive or abrasive contacts with the labels. The APAS can be adapted to handle a plurality of different IV bag configurations with adapted kits that include clips and attachments placed on the IV bag to facilitate handling by the APAS gripper member. A printer platen for a label station in the APAS can include a compliant area to provide enhanced initial contact of a printed label with a syringe. A teaching system is also optionally included in the APAS to enable manual or autonomous teaching of interfaces in the APAS to the robot.

DESCRIPTION OF DRAWINGS

FIG. 3 shows an example table for minimum and maximum fill sizes for an intermediary bag.

FIG. 14 is an illustration of an example narrow fluid channel on the inside of a stopper.

FIG. 15 is an illustration of an example of a marginal needle height.

FIG. 16 is an illustration of an example misalignment of a needle with a previous puncture hole.

FIGS. 19A-19B show a needle puncture into a stopper on a vial prior to needle entry into the vial.

FIGS. 20A-20B show a needle puncture into a stopper on a vial after needle entry into the vial.

FIG. 26 is a flow chart of an illustrative batch mode of operation that can be used to fill drug orders provided to the APAS.

Like reference symbols in the various drawings indicate like elements.

DETAILED DESCRIPTION OF ILLUSTRATIVE EMBODIMENTS

In some implementations, an automated pharmacy admixture system (APAS) includes sub-systems for automated fluid transfer operations among medicinal containers such as syringes, vials, and IV bags. In various examples, the systems and techniques are used in an APAS during admixture or compounding and/or dispensing of drug doses. Examples of an APAS are described, for example, with reference to FIGS. 1 through 5 in U.S. Pat. No. 7,610,115, entitled "Automated Pharmacy Admixture System (APAS)," and filed by Rob et al. on Dec. 22, 2005, and with reference to FIGS. 1 through 5 in U.S. patent application Ser. No. 11/389,995, entitled "Automated Pharmacy Admixture System," and filed by Eliuk et al. on Mar. 27, 2006, the entire disclosure of each of which is incorporated herein by reference.

In some implementations, an APAS includes a manipulator that transports medical containers such as bags, vials, or syringes about a substantially aseptic admixing chamber. In some examples, the chamber includes a number of processing stations at which the medical containers are processed to perform reconstitution for prescription medication doses. In certain examples, such processing stations include apparatus to substantially sanitize, disinfect, and/or sterilize portions of the medical containers prior to performing a fluid transfer operation.

In an example implementation, a gripper assembly is configured to substantially universally grasp and retain syringes, IV bags, and vials of varying shapes and sizes. In an illustrative embodiment, a gripping device includes claws configured to grasp a plurality of different types of IV bags, each type having a different fill port configuration. Embodiments may include a controller adapted to actuate a transport assembly to place a fill port of the bag, vial or syringe into register with a filling port such as a cannula located at a filling station, or be equipped with carousel transport systems that are adapted to convey bags, vials, and syringes to the admixture system and deliver constituted medications in bags, vials or syringes to an egress area.

Figure 1:
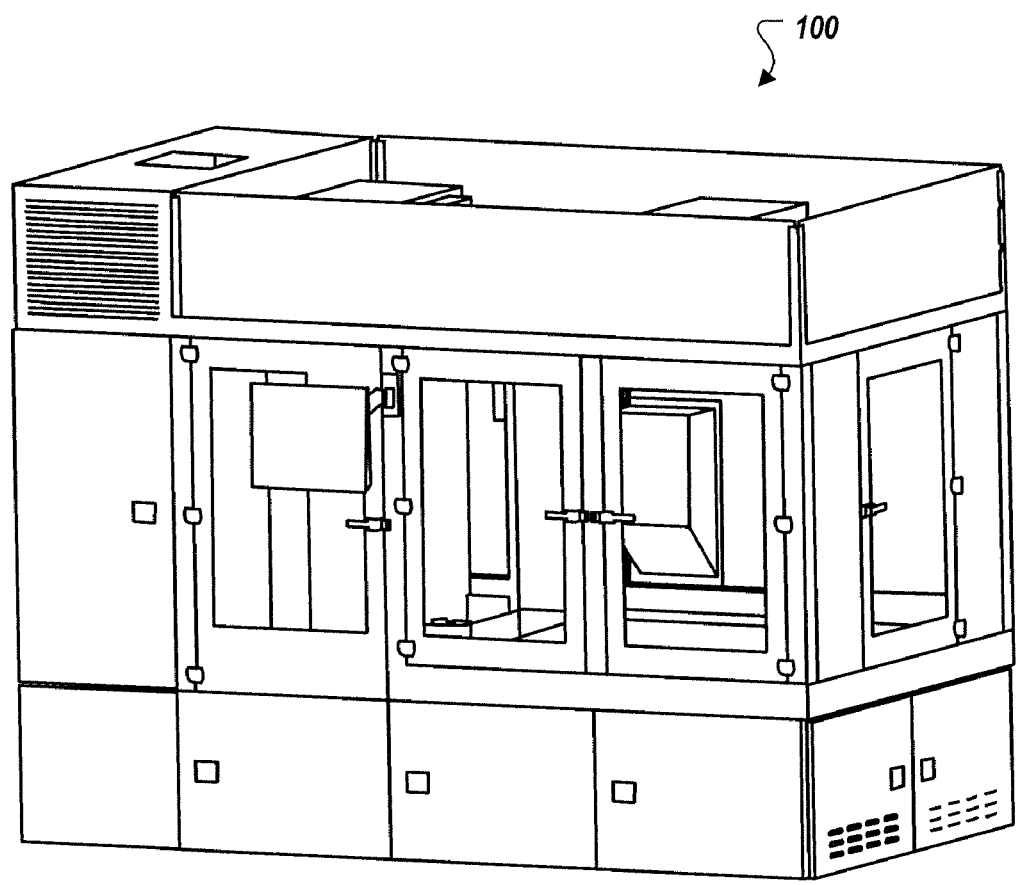
FIG. 1 shows an illustrative Automated Pharmacy Admixture System (APAS).

FIG. 1 shows an illustrative APAS 100 for use within a hospital pharmacy environment. The APAS 100 automatically admixes the contents of syringes and IV bags using automation technologies. For example, embodiments of the APAS 100 can perform one or more operations that might otherwise be performed by pharmacy staff within a laminar airflow hood. The APAS 100 includes a robotic cell that automates the compounding and dispensing of drug doses into IV bags and/or syringes, such as those that may be prepared in hospital pharmacies. The robotic cell can use a syringe-based fluid transfer process, and can employ a robotic manipulator (e.g., a multiple degree of freedom arm) for moving drug vials, syringes, and IV bags through the cell as the medications are processed.

Figure 2:
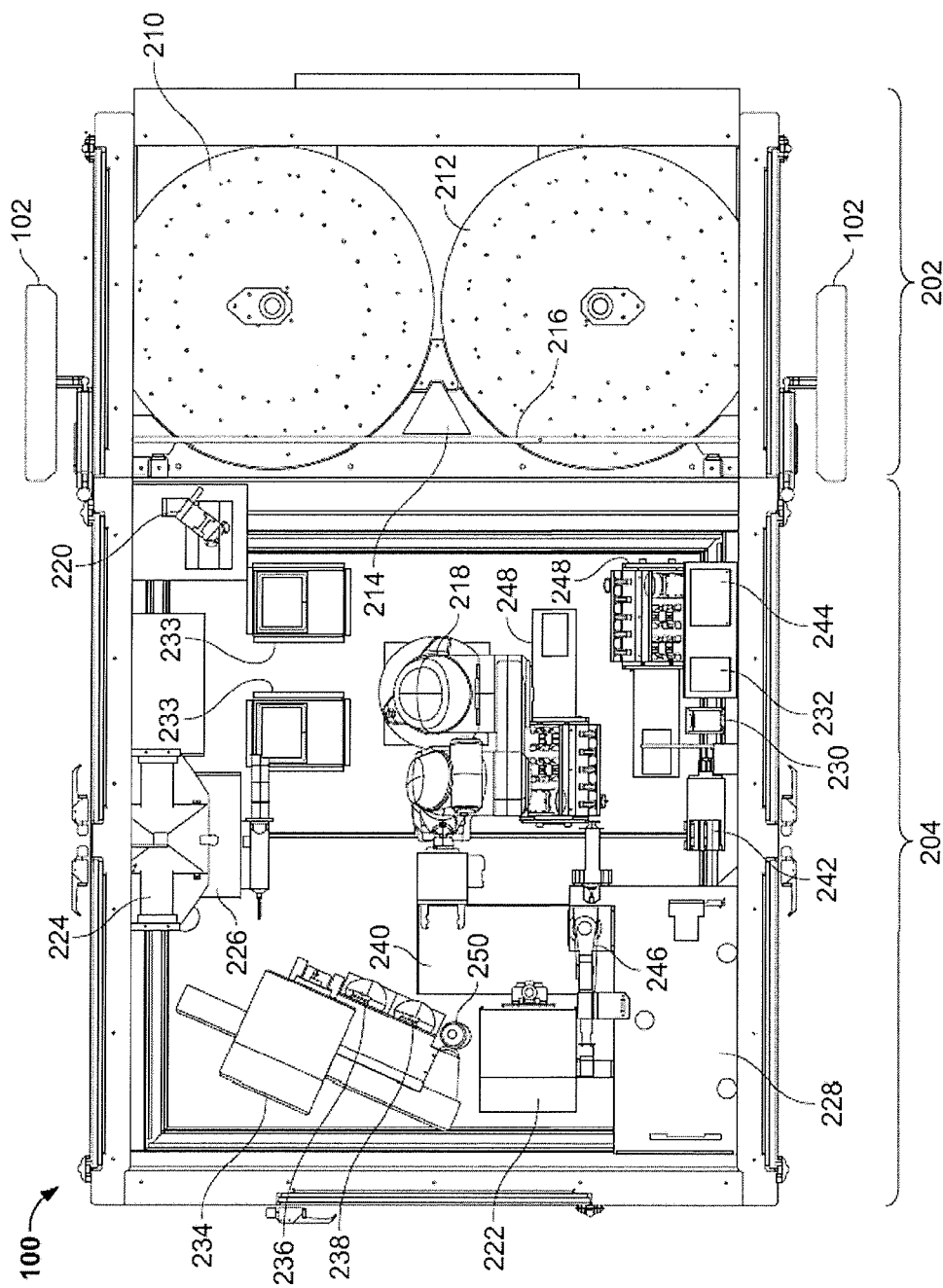
FIG. 2 shows a top cut-away view of the APAS of FIG. 1.

FIG. 2 shows an illustrative top cut-away view of the APAS of FIG. 1. The APAS 100 includes two chambers. An inventory chamber 202 is used as an inventory loading area, which can be accessed by an operator to load the APAS 100 through a loading door (not shown). In some embodiments, the inventory chamber 202 provides a substantially aseptic environment, which may be an ISO Class 5 environment that complies with clean room standards. A processing chamber 204 includes the compounding area in which the admixture and/or compounding processes may occur. In some embodiments, the processing chamber 204 provides a substantially aseptic environment, which may be an ISO Class 5 environment that complies with clean room standards. Mounted on the exterior of the APAS 100 are two of the monitors 102, which may serve as input/output devices.

The inventory chamber 202 includes two inventory rack carousels 210 and 212 and a temporary inventory rack 214. The temporary inventory rack 214 can be used to locate in-process drug vials that contain enough material to provide multiple doses. Each inventory rack carousel 210 or 212 supports multiple inventory racks (not shown). In some applications, an operator may remove one or more racks from the carousels 210, 212 and replace them with racks loaded with inventory. The racks may be loaded onto the carousels 210, 212 according to a load map, which may be generated by the operator for submission to the APAS 100, or generated by the APAS 100 and communicated to the operator. The chambers 202, 204 are substantially separated by a dividing wall 216.

The processing chamber 204 includes a multiple degree of freedom robotic arm 218, and the robotic arm 218 further includes a gripper that can be used, for example, to pick items from a pocket on a rack or to grasp items within the APAS 100 for manipulation. The robotic arm 218 can respond to command signals from a controller (not shown) to pick up, manipulate, or reposition inventory items within the processing chamber 204, and in or around the carousels 210, 212. The robotic arm 218 can manipulate inventory items, for example, by picking a vial, IV bag, or syringe from a rack of the carousels 210, 212 in the inventory chamber 202, and moving the item to a station in the processing chamber 204 for use in compound preparation. In some examples, the robotic arm 218 manipulates inventory items on the carousels 210, 212 through an access port (not shown) in the dividing wall 216. The dividing wall 216 may be substantially sealed so that a substantially aseptic environment may be maintained for compounding processes in the processing chamber 204.

According to an illustrative example, an incoming drug order from a remote user station (not shown) involves a batch production order for syringes to be charged with individual doses of a drug that is reconstituted from a drug provided in one or more vials. The operator, for example, preloads the drug into the APAS 100 during a loading process by loading the carousel 210 with inventory racks of the drug vials, and by interfacing with the APAS 100 using the input/output device 102 to initiate, monitor, and/or control the loading process. As the APAS 100 is processing a previous order, the operator may load the carousel 212 with inventory racks of syringes, drug vials, and IV bags for the next batch production order while the APAS 100 is operating the carousel 210. Once the loading process is complete, the operator may submit the batch production process, which may begin immediately, or after other processing is completed.

To execute the batch production, in this example, the robotic arm 218 picks a syringe from a pocket in a rack in carousel 210. The syringe in the carousel includes a needle and a needle cap. The needle cap is removed for processing in the APAS 100. The robotic arm 218 conveys the syringe to a decapper/deneedler station 220 where the needle cap is removed from the syringe/needle assembly to expose the needle. The robotic arm 218 moves the syringe to a scale station 226 where the syringe is weighed to determine its empty weight. The robotic arm 218 may transfer the syringe to a needle-up syringe manipulator 222 where a dose of the drug is drawn from a vial, which was previously placed there by the robotic arm 218 after one or more verification operations (e.g. weighing, bar code scanning, and/or machine vision recognition techniques). The robotic arm 218 moves the syringe to the decapper/deneedler station 220 where the needle is removed from the syringe and disposed of into a sharps container (not shown). The robotic arm 218 then moves the syringe to a syringe capper station 224, where the needleless syringe is capped. The robotic arm 218 moves the syringe to a scale station 226 where the syringe is weighed to confirm the predetermined dose programmed into the APAS. The robotic arm 218 then moves the syringe to a printer and labeling station 228 to receive a computer readable identification (ID) label that is printed and applied to the syringe. This label may have a bar code or other computer readable code printed on it, which may contain, for example, patient information, the name of the drug in the syringe, the amount of the dose, as well as date and/or lot code information for the inputs. For example, the information printed on the label can depend on the requirements of the hospital system for patient dose labeling. The robotic arm 218 then moves the syringe to an output scanner station 230 where the information on the ID label is read by the scanner to verify that the label is readable. The APAS 100 may report to the remote user station using a local communication network, for use in operations planning. For example, the APAS 100 may record the dispensing of the medicament for later reporting to the hospital system. The syringe is then taken by the robotic arm 218 and dropped into the syringe discharge chute 232 where it is available to the pharmacy technician, for example, to be placed in inventory within the hospital pharmacy. As the process continues, there may be times during the drug order process where the robotic arm 218 removes an empty vial from the needle-up syringe manipulator 222 and places it into a waste chute 233. For example, while processing a drug order, the APAS 100 can use more than one vial to process a single order. Therefore, the robotic arm 218 can dispose of the empty vial prior to replacement of a new vial in the needle-up syringe manipulator 222.

In another illustrative example, a syringe is used both as an input containing a fluid (e.g., diluent or known drug compound) to be admixed in a compounding process, and as an output containing a prepared dose suitable for delivery to a patient. Such a syringe is needed to fulfill a special reconstitution order programmed into the APAS 100 via the input/output capabilities of the monitor 102, for example. In another example, the order is a stat order, which is received from a hospital interface. In this example, the operator performs in situ loading by placing the syringes to be used for both reconstitution and dosing in pockets on a rack already located on the carousel 210. The operator enters the reconstitution order into the APAS 100. The robotic arm 218 picks the selected syringe from a pocket in the rack in the carousel 210 and moves it to the decapper/deneedler station 220, where the needle cap is removed from the syringe/needle combination, thereby exposing the needle. The syringe is then transferred by the robotic arm 218 to a needle-down syringe manipulator 234. At the station 234, diluent is drawn into the syringe from a diluent supply IV bag 236 previously placed there by the robotic arm 218. The diluent supply 236 is contained in an IV bag, which is hung on the needle-down syringe manipulator 234 by a clip (not shown). For example, an air extraction process is performed to prime the IV bag, if needed. The syringe then punctures the membrane of the diluent port 238 in a needle-down orientation. The syringe is actuated to remove, for example, a predetermined amount of the diluent from the IV bag. The needle-down syringe manipulator 234 then moves a reconstitution vial 250, placed there previously by the robotic arm 218, under the syringe. The diluent in the syringe is transferred to the vial for reconstitution with the vial contents. The robotic arm 218 then moves the vial to a mixer 248 for shaking according to a mixing profile. The robotic arm 218 then moves the vial to the needle-up syringe manipulator 222 where the appropriate amount of the reconstituted drug is drawn from the vial into an "output" syringe that was previously conveyed there by the robotic arm 218.

In another embodiment, the APAS 100 receives a production order to prepare compounds that involve IV bags as input inventory items or as outputs. In some examples, an IV bag is selected as a diluent source for reconstitution in a drug order to be output into another medical container. In other examples, the selected IV bag is used for output after preparation of the drug order is completed. For example, the IV bag is placed on the carousels 210, 212 and used as an input that may be at least partially filled with a diluent that may be used to reconstitute drugs. In some examples, the IV bag may be previously unused and completely filled with the diluent. The reconstituted drugs are output in the form of charged syringes or IV bags. The operator loads racks of syringes and IV bags into the carousel 210 for use in the production order. During the production order, the robotic arm 218 picks an IV bag from a rack on the carousel 210 and moves it to the scale and bag ID station 226. At this station, the IV bag is identified by bar code or pattern matching and its weight is recorded. For example, IV bag identification is performed as an error check, and/or to positively identify the type and/or volume of diluent being used for reconstitution. If the IV bag is selected as a diluent source, then the bag is weighed before use to confirm the presence of the diluent in the IV bag. If the IV bag is selected for output, it is weighed multiple times, such as before, during, and/or after each fluid transfer step, for example. As a post-transfer verification step, the weight is re-checked after fluid transfer operations have occurred to determine if the change in weight is within an expected range. Such checks detect, for example, leaks, spills, overfills, or material input errors. In this example, the robotic arm 218 moves the IV bag to a port cleaner station 240 where a ultraviolet (UV) light or other sanitizing process is used to substantially sterilize, disinfect or sanitize at least a portion of the IV bag port. The robotic arm 218 moves the IV bag to the needle-up syringe manipulator 222 where a pre-filled syringe has been loaded. The IV bag is inverted so that the fill port is oriented downwardly for the fill process. The contents of the syringe is injected into the IV bag. The robotic arm 218 then conveys the IV bag to the scale station 226 where the IV bag is weighed to confirm the predetermined dose programmed into the APAS 100. The robotic arm 218 then moves the IV bag to a bag labeler tray station 242 where a label printed by the printer and labeling station 228 is applied to the IV bag. The robotic arm 218 moves the IV bag to the output scanner station 230, where the information on the ID label is read by the scanner to verify that the label is readable. One or more further verification checks may be performed. For example, the output scanner station 230 can compare the scanned label information to the expected label information to verify that the correct medicament is being dispensed. The IV bag is then taken by the robotic arm 218 and dropped into the IV bag discharge chute 244 where it is available to the pharmacy technician, for example, to be placed in inventory within the hospital pharmacy.

In another embodiment, a vial (or other medical item or container) is prepared for reconstitution. During the performing of this process by the APAS 100, the vial is identified at a vial ID station where, for example, a bar coded label on the vial is read by a scanner and/or image hardware in combination with image processing software. The captured information is processed to identify the contents of the vial and correlate it to what is expected. In some implementations, as an alternative to or in combination with bar code scanning, the APAS 100 employs pattern matching on the vial using optical scanning techniques. In addition, in the reconstitution process, vial mixers 248 are used to mix the vial contents with the diluent before using it for dosing.

In some embodiments, the robotic manipulator includes apparatus for reading machine readable indicia in the APAS, including the compounding chamber and/or the storage chamber. For example, the manipulator includes an electronic camera for taking images that can be processed to compare to stored image information (e.g., bitmaps). In other examples, the images may be stored without any additional processing. In other examples, the reading apparatus includes optical scanning (e.g., bar code) or RFID (radio frequency identification). Some embodiments transmit image information wirelessly (e.g., using infrared or RF (radio frequency) transmissions) to a receiver coupled to the APAS. For example, the receiver is located inside or outside the chamber with the robotic manipulator. For example, the reader is used to read machine readable indicia at various locations in and around the compounding chamber, including through windows and on portions of the storage carousels that are exposed to the compounding chamber.

Intermediate IV Bag Handling

Intermediate bag functionality enables the APAS to use previously prepared IV bags (intermediary bags) as drug sources for creating patient doses in syringes. The APAS creates a dosed syringe at a lower concentration than that available when using the syringe to dilute the concentration of drugs.

The use of an intermediary bag to create a dosed syringe is a two-step process. In a first step, a user defines, trains, and creates a new drug source type. The APAS uses a front end form in a training wizard to train a new drug source by defining the diluent and drug source to be used and a final concentration and bag volume for the intermediary bag. When training for a new drug source introduced by an intermediary bag, a final volume is an absolute value with respect to the total volume of the intermediary bag. Alternatively, when training for the new drug source introduced by the intermediary bag, a final volume is the total volume of the intermediary bag that includes the new drug source.

A created intermediary bag is output from the APAS for possible later use in the APAS. The APAS creates the intermediary bag in a final volume bag by controlling the amount of fluid (diluent) and the amount of drug in the bag. In creating the intermediary bag, the APAS weighs a diluent bag, determines the amount of fluid in the bag, withdraws an amount of fluid required to reduce the amount of fluid in the bag to a specified amount, and adds a specific amount of drug to the bag. The APAS at a syringe manipulation station then removes an amount of diluent necessary to accurately make the intermediary bag at the absolute final volume entered by the user into the front end form in the training wizard.

For example, to produce a concentration of 20 ml of drug in a final volume of 200 ml of normal saline (NS) to create an intermediary bag, the APAS can use an existing 250 ml bag, weigh the bag to determine it contains 272 ml of NS, withdraw 92 ml of fluid from the bag, discard the withdrawn fluid, and add 20 ml of drug to the bag to create an intermediary bag that includes a diluted drug source with a final volume of 200 ml.

A user operating a workstation interfaced to the APAS can launch a drug order that will use the produced intermediary bag. The user launches the drug order using a hospital interface (patient specific). Alternatively, the user launches a drug order using a front end drug order form (non-patient specific).

In some implementations, the APAS creates intermediary bags at off peak use times for the APAS. The APAS outputs the intermediary bags with an appropriate label. Alternatively, the APAS outputs the intermediary bag without a label where the label is printed and applied external to the APAS (e.g., an operator takes a printed label and affixes it to the intermediary bag). For example, an intermediary bag can be characterized by it's drug name, concentration and final volume.

The APAS accepts a single or multiple entries of a single intermediary bag. When outputting multiple entries of a single intermediary bag, the size of the intermediary bag is selected to minimize waste of unused drug source. For example, the APAS creates four 250 ml intermediary bags compared to making a single one liter bag.

To create an intermediary bag with an accurate final volume, an initial or "empty bag" weight is determined for each size fluid diluent bag used to create an intermediary bag. The APAS controller uses the empty bag weight to determine a total volume amount that may include an overfill amount for the diluent bag. The APAS controller in a volume adjustment step determines how much of the total volume in the diluent bag can be removed to obtain the trained final volume for the intermediary bag. The user monitors any manufacturer changes in diluent bags used by the APAS and also insures that diluent bags introduced into the APAS are intact.

A user uses an intermediary bag training wizard to train the APAS to use an intermediary bag. The user uses a user interface included in the APAS and described with respect to, for example, FIG. 2 of previously incorporated by reference U.S. patent application Ser. No. 11/389,995, entitled "Automated Pharmacy Admixture System," and filed by Eliuk et al. on Mar. 27, 2006, to enter a drug type, a diluent type and a diluent bag volume (bag size and type) for training the intermediary bag on the APAS. While training the APAS, the user enters a final volume and concentration for the intermediary bag and a draw volume adjustment that specifies how much volume to remove from the intermediary bag (e.g., when drawing doses from the intermediary bag into a syringe).

The final volume of the intermediary bag can be greater than that for an original diluent bag and may be less than the volume specified by the APAS for a maximum allowable volume for the original diluent bag. An IV bag has an overfill value that is added to the total allowed volume for the IV bag. For example, an allowable volume for an IV bag type is set based on manufacturers' data.

The APAS controller assigns a newly trained intermediary bag a unique "type number." The type number can be unique for a trained intermediary bag type but may not be unique for each of the same type intermediary bags produced. For example, the APAS produces an intermediary bag that includes a concentration of 20 ml of a specific drug in a final volume of 200 ml of NS. This newly trained intermediary bag is assigned a unique type number 101. Additional intermediary bags produced by the APAS that include a concentration of 20 ml of the same drug in a final volume of 200 ml of NS are assigned the same type number 101 when trained in the APAS. The user uses the type number when reloading the intermediary bag into the APAS. The type number becomes the "name" for the specific intermediary bag type.

The user sets one or more expiry times (e.g., a time in minutes, days, hours, weeks, months, etc.) for an intermediary bag. The expiry time for the intermediary bag begins from the time of the first access of the intermediary bag (e.g., the first puncture of a port on the intermediary bag with a needle of a syringe). Alternatively, the expiry time for the intermediary bag begins from the time of the first puncture of any of the constituents to be used for the production of the intermediary bag. The expiry times are trained expiry times entered by the user when training the APAS to use the intermediary bag.

The APAS controller validates the expiry time for the intermediary bag. The expiry times for the products (e.g., drugs, diluent) used to produce the intermediary bag are taken into account when determining the expiry time for the intermediary bag. Additionally, any refrigeration or freezing times associated with products used to produce the intermediary bag can be taken into account when determining the expiry time for the intermediary bag. An expiry time is set to start at the moment the intermediary bag is output from the APAS. The expiry time is checked when the intermediary bag is loaded back into the APAS to insure that the bag is still within the expected expiry time. A second expiry time begins to track how long the intermediary bag is used to draw doses from within the APAS. For example, a first expiry time can be 9 days so that once the bag is made there can be a 9 day window to allow reentry of the bag into APAS. In another example, once loaded, a new expiry time of 24 hours, can insure that doses are not drawn from the bag after 24 hours. The first expiry time can reduce the second expiry time in the event the in the cell time is longer than the out of cell time remaining.

When training the APAS to use an intermediary bag, the puncture limit (e.g., the number of times a port can be accessed by a needle on a syringe) for the intermediary bag is the same as or less than the puncture limits for the original source fluid IV bag used to created the intermediary bag. The user sets the puncture limit for the intermediary bag.

FIG. 3 shows an example table 300 for minimum and maximum fill sizes for an intermediary bag. In some implementations, original source fluid bags that contain less than 25 ml are not used. In some implementations, the minimum drug dose that is put into any size of a source fluid bag is 1.8 ml. The minimum fill size limits are determined based on the accuracy of the scale in the APAS used to weigh the bags during processing. The minimum amount of fluid that remains in an intermediary bag during a volume adjustment step in the APAS is, for example, 20% of the nominal bag volume. For example, a 100 ml bag can be drawn down where 20 ml of fluid remains in the bag (e.g., 80 ml of fluid can be removed from the bag) before the desired amount of drug is added to the bag to produce the intermediary bag.

When training an APAS to use an intermediary bag, a draw volume adjustment specifies how much volume is removed from the intermediary bag when drawing doses from the bag. A negative draw volume adjustment indicates drawing a volume amount that is less than what is specified as the final volume of the intermediary bag. A positive draw volume adjustment indicates drawing a volume amount that is more than what is specified as the final volume of the intermediary bag. A positive draw volume amount may not be used as the final volume of the intermediary bag as it may not include an overfill adjustment value.

A user trains the APAS to use intermediary bags with a weigh after prime flag initially set to ON. Setting the weigh after prime flag to ON enables the APAS to gather statistical information on the amount of fluid removed during an IV bag priming process. This may decrease the number of potential overdraw failures that occur in the APAS when drawing doses from the intermediary bag. Reweighing a bag after the priming step allows a more accurate weight of the total bag to be recorded for later use in adjusting the amount of diluent in the bag.

The APAS can create and produce one or more intermediary bags one at a time or in a batch mode using front end non-patient specific drug order forms. This enables the batch production of a plurality of one bag type or multiple different bag types within the same batch order. A user enters values into a production queue table that enables the user to select a drug source, a diluent source, an intermediary bag concentration and a desired number of doses for the intermediary bag. After entering the values into the production queue table, the APAS controller creates a production queue that the APAS cell uses for making the intermediary bags where the sequence of process steps for loading and preparing the inventory needed for the intermediary bag production parallels that of a non-intermediary or standard queue for creating a drug order.

In an illustrative embodiment, when producing an intermediary bag, a robotic arm removes a diluent bag from inventory (e.g., remove a diluent bag from an inventory carousel), the APAS controller verifies, for example, the bag stem height, the robotic arm places the bag in the UV port sanitization system, the APAS controller verifies that the bag is that expected by checking, for example, the National Drug Code (NDC) barcode of the diluent bag at a bar code scanner and the initial weight of the diluent bag is checked at a scale. If the diluent bag passes the verification checks, the robotic arm moves the diluent bag to a syringe manipulator device where the diluent bag can be primed to remove air. The bag priming process is described in FIGS. 15A-15C of previously incorporated by reference U.S. patent application Ser. No. 11/389,995, entitled "Automated Pharmacy Admixture System," and filed by Eliuk et al. on Mar. 27, 2006. Additionally, the robotic arm removes vials from inventory (e.g., remove a vial from an inventory carousel) and verifies the vial identification information and height at an identification station. The robotic arm places the vial in the UV port sanitization system, the vial is weighed on a scale, the vial is reconstituted (when applicable) and then the robotic arm parks the vial once complete.

The empty weight of an IV bag is used in determining how much diluent to withdraw when making the intermediary bag. IV bags typically contain overfill from their nominal fill volume (eg, a 100 ml bag may contain 110 ml of diluent). Accounting for this overfill, which may change from bag to bag, is important to ensure that the correct amount of diluent is withdrawn. In addition, accuracy may further be enhanced by weighing the bag after the priming step. The total weight of the bag is the empty weight of the bag plus the weight of the fluid in the bag. As the fluid density of the diluent is trained into APAS, the volume of diluent is calculated by subtracting the empty weight of the bag from the total weight and converting diluent weight to volume using the diluent density. Once the volume of diluent in the bag is known, the appropriate amount is extracted to achieve the desired amount of diluent in the IV bag.

An empty IV bag is used to prepare an intermediary bag. For example, an empty 150 ml IV bag is used to make an intermediary bag that contains 100 ml of drug and 50 ml of diluent. In cases where the amount of diluent is small, starting with an empty bag may be efficient from a production time perspective.

The APAS adds additional diluent to an IV bag already containing diluent to achieve the desired amount of diluent in the bag. For example, 50 ml of diluent is added to a 500 ml bag, which actually contains 530 ml of fluid, to provide a total of 580 ml of diluent to dilute 10 ml of drug in. This is more efficient from a production time perspective than drawing 400 ml or more of diluent from a 1000 ml IV bag to achieve the same amount of diluent in the IV bag.

Figure 4:
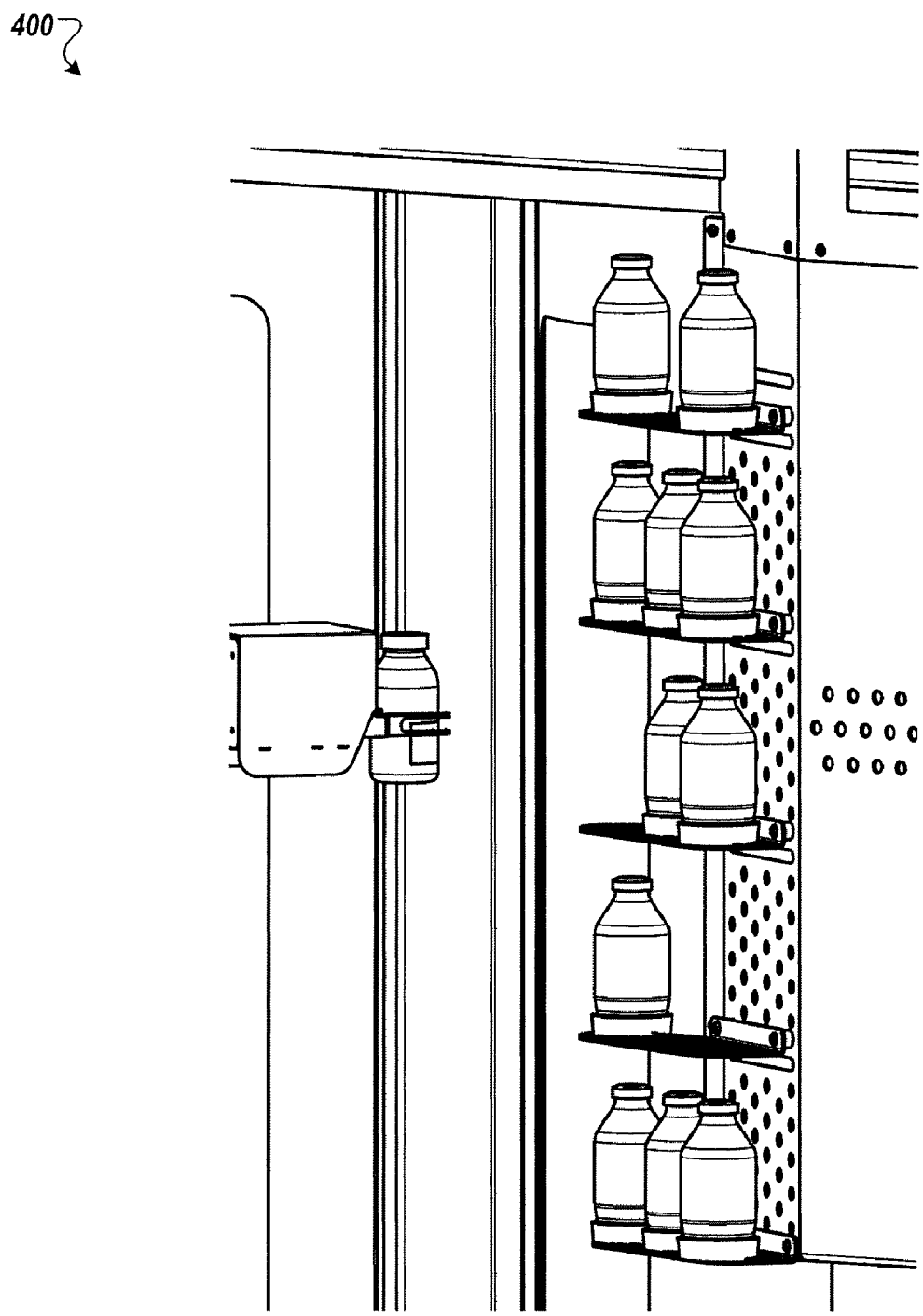
FIG. 4 shows an example vial parking.

FIG. 4 shows an example vial parking location 400 in an APAS. The APAS, in order to prevent software conflicts between preparing diluent bags on the syringe manipulator device and reconstituting vials on the syringe manipulator device, first reconstitutes the vials and then parks them (e.g., on vial parking shelves in vial parking location 400) before preparing the diluent bags. The APAS removes existing vials from the vial parking shelves and places them on a reject rack if additional parking positions are needed on the vial parking shelves to complete a production queue for the production of an intermediary bag.

Figure 5:
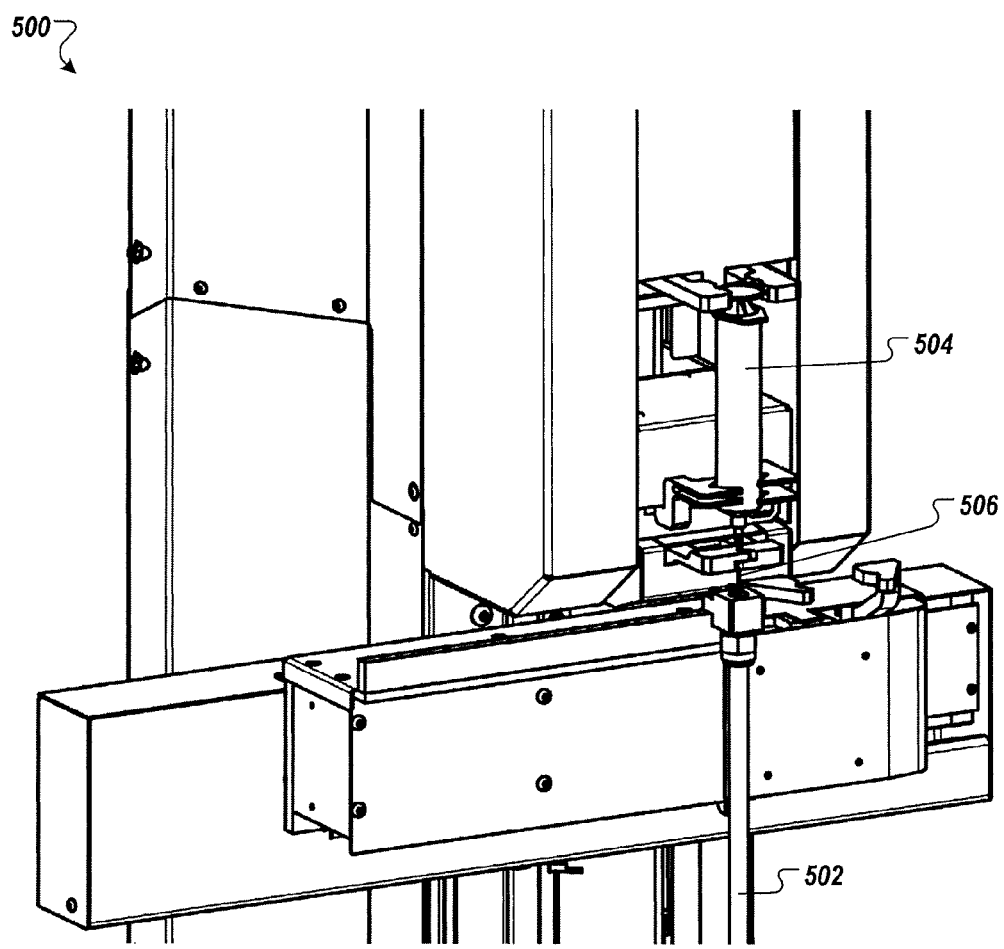
FIG. 5 shows an example syringe manipulation device that includes a liquid waste drain tube.
Figure 6:
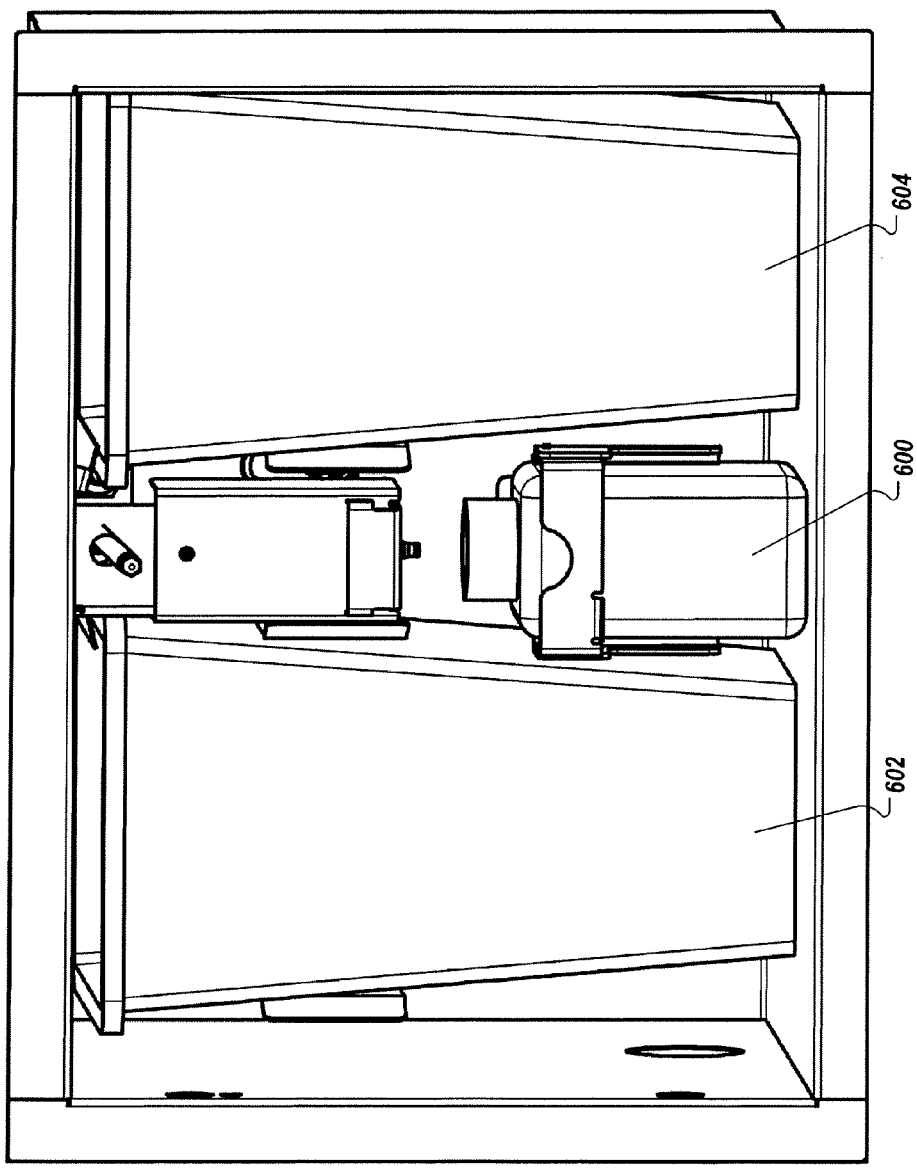
FIG. 6 shows an example liquid waste container.

FIG. 5 shows an example syringe manipulation device 500 that includes a liquid waste drain tube 502. FIG. 6 shows an example liquid waste container 600. The diluent bag is weighed on a scale after priming to ensure the accuracy of the diluent volume adjustment for the intermediary bag. The syringe manipulator station extracts the appropriate amount of diluent from the bag needed to create the trained final volume for the intermediary bag less the total drug volume that the APAS adds to the bag to create the intermediary bag. The APAS uses an extraction syringe and needle (e.g., syringe 504 and needle 506) to dispense the discarded liquid into a liquid waste drain tube (e.g., liquid waste drain tube 502) located on the syringe manipulator device (e.g., syringe manipulator device 500). The liquid waste drain tube 502 drains the discarded fluid into the liquid waste container 600 located in a waste bin area of the APAS. A user can regularly empty the liquid waste container 600 during APAS idle times.

Figures 7, 8:
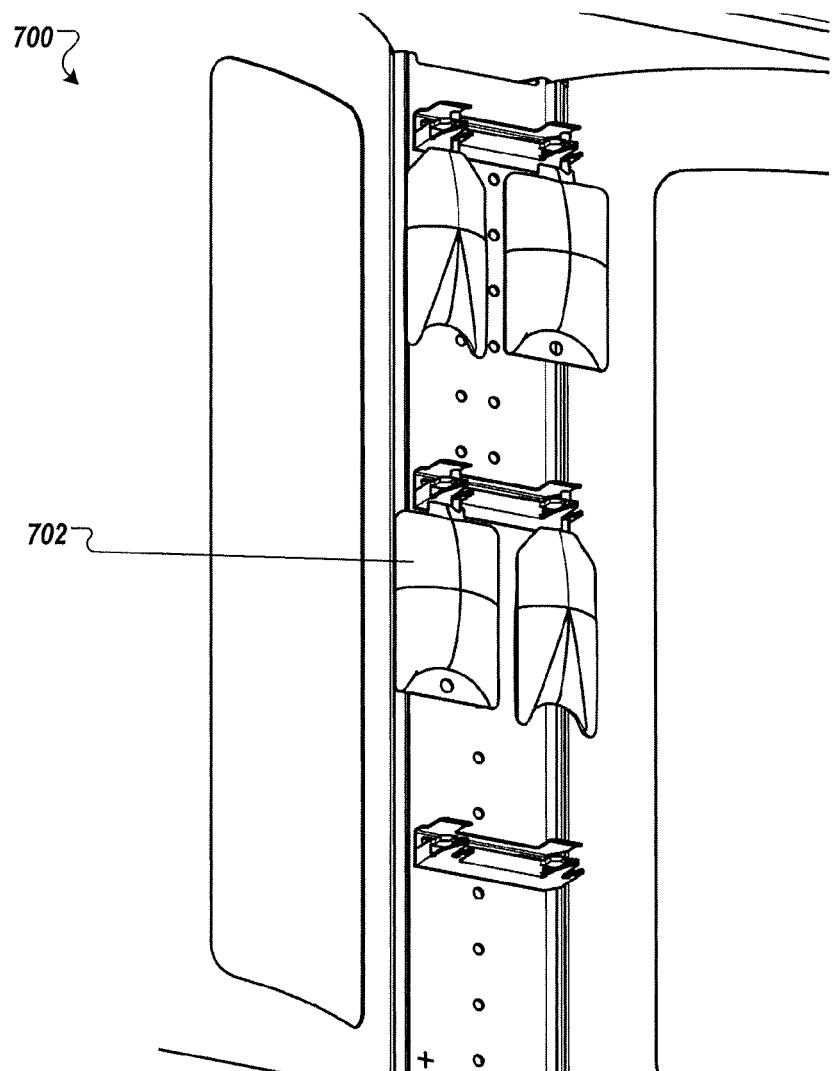
FIG. 7 shows an example IV bag parking.
FIG. 8 shows an example adjusted volume weight verification interpolation table.

FIG. 7 shows an example IV bag parking location 700 in an APAS. The robotic arm places a volume-adjusted diluent bag 702 in an IV bag parking location 700 in the APAS. The APAS commands the syringe manipulation device to draw a specific amount of a drug from an appropriate vial. One or more vials are used to obtain the specific amount of drug needed to produce the intermediary bag. The number of vials may be limited based on the number of available vial parking shelves to hold the vials needed to produce the intermediary bag.

For example, the APAS moves the diluent bag from its parked position back to the syringe manipulation device. The amount of drug drawn into the syringe at the syringe manipulation device is introduced (e.g., pushed) into the volume-adjusted diluent bag creating the intermediary bag. After adding the drug to the volume-adjusted diluent bag, the APAS checks the weight of the intermediary bag to verify accurate dosing.

The APAS labels the intermediary bag with a intermediary bag label. The intermediary bag label includes a type number that the APAS uses when reloading the intermediary bag back into the APAS. The APAS prints a bar code that includes the type number on the intermediary bag label. The APAS reads the bar code and uses the encoded information to identify and verify the intermediary bag when a user reloads the intermediary bag back into the APAS. For example, the intermediary bag label includes a line for an approval signature and a blank line to allow hand addition of any additional information. In another example, the label printer prints the intermediary bag expiry dates on the intermediary bag label. When loading an intermediary bag into the APAS, a user selects intermediary bags closer to their expiry date to load first into the APAS.

If the intermediary bag passes the verification checks, the robotic arm places the intermediary bag in the output chute for delivery to the user. If the intermediary bag fails one or more verification checks, the robotic arm places the intermediary bag on a reject. The APAS may apply a label to the rejected bag indicating the reason it failed verification (e.g. incorrect mass/volume of diluent or drug).

Diluent used to reconstitute a drug vial is obtained from an IV bag different from the source diluent bag for the intermediary bag. The APAS performs fluid cycling with the syringe at the syringe manipulation device after drug injection into the source diluent bag to move drug out of the neck of the bag and into the body of the bag. A user performs adequate mixing of the drug and diluent in the intermediary bag while handling the intermediary bag outside of the APAS.

The following describes, in some implementations, the use of an intermediary bag in the APAS to produce a drug order. Upon receiving one or more drug order(s) that require the use of one or more intermediary bag(s), the APAS requests the user to load specific type numbers of intermediary bags into the APAS. For example, the type number can be included on the intermediary bag label. The APAS reads the intermediary bag label (e.g., the bar code printed on the intermediary bag label using a barcode scanner). The APAS uses the data read from the intermediary bag label (e.g., bar code label data read by the bar code scanner) to determine if the user is loading the correct intermediary bag into the APAS. Additionally, the APAS determines the drug order identification (e.g., DrugOrderID) of the intermediary bag.

The APAS uses one or more intermediary bags to produce a single output ordered dose. If a first intermediary bag is emptied during dose preparation, a second intermediary bag is used to complete the dose preparation. The robotic arm parks or stores a partially used intermediary bag in IV bag parking for use in a later subsequent drug order process. If a parked intermediary bag needs to be removed for drug priority reasons, it is placed on the reject rack. A user ensures that an adequate number of the required intermediary bags are available before the user begins a drug order run on the APAS. If the APAS requires the use of another intermediary bag during the drug order run and the bag is not available, the user stops the drug order run.

When drawing a dose from an intermediary bag for the first time, the APAS primes the intermediary bag using the syringe selected for the preparation of the dose. The priming of the intermediary bag by the APAS removes any air in the intermediary bag that may have migrated from the additional port on the intermediary bag.

In some implementations, the APAS recovers from initial failures during the use of an intermediary bag in a drug order run. The APAS recovers from an initial bag weight failure. This failure occurs when the current weight of a bag compared to the previous weight of the bag when prepared do not agree. The APAS recovers from an error resulting from the attempted use of an expired bag. In order to recover from this error, additional bags of that type need to be available for use by the APAS. The APAS recovers from a height check failure and from a barcode verification check failure. The APAS recovers from an error that may occur while priming the diluent bag. Error handling and recovery in an APAS is described in further detail with reference to FIG. 31.

A user performs available volume training for vials and bags on an APAS. The available volume of a drug is the volume of the drug that can be physically drawn from a drug source container (e.g., a vial or bag). The available volume is a result of physical characteristics of the drug source container. The APAS may not be able to remove all of the available drug from the drug source container. A user of the APAS can specify a maximum available volume of a liquid to draw from the drug source container where the specified maximum available volume for the draw is different than the amount specified on the original source container drug label. The possible difference between the maximum available volume for draws and the amount specified on the drug source container occurs for intermediary bags as well as the additional drug source container. For example, a user specifies 9.8 milliliters (mls) of fluid be drawn from a 10 milliliter (ml) vial, leaving 0.2 mls of liquid in the vial as the APAS may not be able to remove all of the liquid from the vial.

A user specifies a different available volume in a drug source container than specified on the actual drug source container. A remote user station prompts the user for the actual drug source used. The APAS allows for compensation for overfill of a drug source container. The user specifies the available volume in a drug source container when training diluent sources on the APAS. When training intermediary bag sources on the APAS, the user also specifies the available volume in the intermediary bag source container, which may be different from the volume specified for the original diluent bag source container used to produce the intermediary bag. When training drug vial sources on the APAS, the user specifies the available volume in the drug vial.

The APAS database generates a drug report that indicates the original source diluent bag and vial that the APAS used to produce the intermediary bag. For example, a picture of the resultant intermediary bag is used in the drug report. The APAS database creates a report that indicates how many non-expired intermediary bags are expected to be stored outside the APAS. The report indicates what the APAS can expect to occur outside of the APAS.

The APAS controller performs diluent bag volume adjustment verification. Each diluent bag source has a prescribed minimum volume and maximum volume to which it is adjusted. The APAS controller uses average dry weight data for each diluent bag source part number or type to calculate an estimate of the fluid volume in the diluent bag. The APAS reweighs diluent bags after priming on a scale. Alternatively, if the APAS does not reweigh diluent bags after priming, the APAS controller uses an average priming volume to calculate the fluid adjustment volume for the diluent bag. The adjusted fluid volume is confirmed by weight, employing the density numbers for the applicable fluid.

FIG. 8 shows an example adjusted volume weight verification interpolation table 800 used to perform diluent bag volume adjustment verification. The limits for deviation from the expected fluid weight of a diluent bag are interpolated from table 800 based on the size of the dose or amount of fluid removed from the diluent bag by a syringe. The limits included in the table 800 may be smaller than the specified accuracy limits due to allowance for scale inaccuracy.

Column 802 includes information about the type of syringe used to remove the dose from the diluent bag. An APAS supports a plurality of syringe types. The APAS can associate each syringe type (e.g., seven syringe types) with a number (e.g., a number from one to seven, respectively). In the example in table 800, syringe type number four is used.

Column 804 includes information about the percentage of the syringe nominal volume that the expected fluid weight of the diluent bag can vary. In the example table 800, this percentage is 10%. The percentage of the syringe nominal volume can be a number from approximately 0.1 to 1.0 (10% to 100%)

Column 806 includes information about the percentage of error tolerance for a fluid adjustment when the diluent bag is reweighed after the bag is primed. In the example table 800, the error tolerance is plus or minus (±) 4.0%. The variation of ±4.0% is applied to the nominal weight or volume of the diluent bag remaining fluid to generate a maximum and a minimum weight limit.

Column 808 includes information about the percentage of error tolerance for a fluid adjustment when the diluent bag is not reweighed after a dose is removed from the bag. In the example table 800, the error tolerance is plus or minus (±) 8.0%. The variation of ±8.0% is applied to the nominal weight or volume of the diluent bag remaining fluid to generate a maximum and a minimum weight limit. The percentage of error tolerance for a fluid adjustment when the diluent bag is not reweighed after priming can be larger than the percentage of error tolerance for a fluid adjustment when the diluent bag is reweighed after priming to allow for the variation in an unknown priming volume. The priming volume is unknown when the diluent bag is not weighed after priming.

The APAS performs intermediary bag drug injection verification. A syringe can draw injected drug doses according to existing syringe manipulation device draw-from-vial parameters. The dose limits for volume (or weight) are verified against a table included in the database of the APAS based on the size of the dose and the size of the syringe used for the dose. The intermediary bag expected nominal delta weight is corrected for fluid lost to syringe dead space due to syringe cycling. The APAS applies error limits to the corrected volume where the error limits are derived from the expected fluid transfer prior to correction. The assumed density of the fluid is the weighted average of diluent and drug densities. The dead space volume is unique per syringe type. After neck-expunge cycling of the syringe, the syringe dead-space is filled with diluted drug. There may be a minimum dose volume for each unique diluent bag type. Software in the APAS confirms that the minimum dose requirement is satisfied using weight verification.

The APAS performs intermediary bag cell reentry verification. When the user loads an intermediary bag into the inventory chamber, the APAS controller verifies the intermediary bag weight using a measured final weight for that intermediary bag at the time of production of the intermediary bag. In some cases, condensation makes the intermediary bag heavier. In some cases, evaporation makes the intermediary bag lighter. Additionally, the weight of the intermediary bag on reentry to the APAS is corrected for the weight of the intermediary bag label, which is applied after the APAS performs a final weight measurement during production of the intermediary bag. The weight correction uses an average label weight stored in the database in the APAS. For example, a bag label weight is approximately 0.350 g. A reentry-weight tolerance is a number (e.g., in grams) for each trained intermediary bag type. The APAS controller performs an intermediary bag drawn syringe dose verification that uses an existing syringe manipulation device bag-source syringe-draw verification.

If an intermediary bag fails in the APAS for any reason after the bag identification verification, the intermediary bag is not reloaded into the APAS in a subsequent run and the intermediary bag is placed in the reject bin. If an intermediary bag fails the bag identification verification, it is reloaded into the APAS in a subsequent drug order run. This failure indicates that the user attempted to load an incorrect intermediary bag into the APAS. The integrity of the drug in the intermediary bag in the case of this error may not be in question allowing for reuse of the intermediary bag.

In some implementations, the intermediary bag is not produced in the same drug order run as it is used for. This enables the APAS to output the intermediary bag to the user for mixing and any other additional handling. The user queues up a subsequent drug order to use the produced intermediary bag. In some implementations, the APAS uses one or more intermediary bags to complete a drug dose order.

When a user has trained the APAS for a particular type of intermediary bag that has been entered into the APAS, the APAS may not allow subsequent changes to the definition of the intermediate bag by the user. Not allowing the user to redefine the intermediary bag after initial training prevents a previously made intermediary bag from re-entering the APAS with an incorrect concentration. For example, the APAS is trained for a particular intermediary bag at one concentration, a definition change changes it to a different concentration, an intermediary bag with original concentration is re-entered into the APAS as the same type, but the APAS now assumes the intermediary bag will have the second specified concentration.

The APAS eliminates the possibility of a user loading an intermediary bag into the APAS as a diluent bag allowing the intermediary bag to go through the initial bag identification checks. For example, the APAS ensures that produced intermediary bags do not have the same initial weights as diluent bags. In this example, the initial bag weight check fails an intermediary bag if it is erroneously loaded into the APAS as a diluent bag. Additionally, the user does not have access in the APAS to change diluent bag weights, ensuring these weights are not accidentally changed. For example, the weights are updated in the APAS based on data gathered from the APAS and bag manufacturer data. The bag empty weights can insure accurate bag volume estimations are preloaded on the APAS.

For example, a user obscures the bag manufacturer's National Drug Code (NDC) barcode on the printed side of the intermediary bag to ensure that it does not pass the bag identification bar code scan check. In this example, the user applies a blank label or some other type of masking device over the bag manufacture's NDC barcode after the production and delivery of the intermediary bag to the user to obscure the bag manufacture's NDC barcode from the bar code scanner in the APAS.

In some implementations, an intermediary bag is agitated (e.g., mixed) after the intermediary bag leaves the APAS for the first time and also before the intermediary bag is reloaded into the APAS or used externally from the APAS. The agitation ensures adequate mixing of the drug and diluent within the intermediary bag.

Vial Seal Puncturing

For purposes of illustration of example embodiments, references are made below to the APAS, which has been used in various experiments as described herein. The APAS accommodates a very large assortment of drug vials to perform aseptic compounding of IV medications. These drug vials can utilize rubber stoppers, or bungs, with a wide range of geometric features and rubber properties. Furthermore, properties of the bung rubber can vary batch to batch of drug vial.

Figure 9:
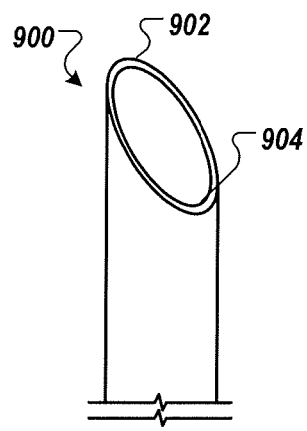
FIG. 9 is an illustration of an example of a 18 gauge blunt fill needle.

FIG. 9 is an illustration of an example of a Becton Dickson (BD) 18 gauge blunt fill needle 900 (Part Number 305180). The needle 900 includes a primary edge 902 and a secondary edge 904. A syringe uses the needle 900 to transfer fluids through vial and bag bungs. The needle 900 is used in pharmaceutical compounding.

A syringe manipulator device performs a process that includes repeated entry through the same vial puncture site with careful control of needle position, needle bevel orientation, and needle entry speed. The process yields beneficial results with respect to bung pressure sealing (with and without needle engagement) and with respect to the tendency to generate particulate. Particular vial bungs lack resilience. The bung properties may make them much more prone than other types of bungs to generate particulate under repeated puncture. The bungs may be more susceptible to cutting from the needle-bevel secondary edge (e.g., secondary edge 904).

Various experiments were performed to explore and develop various means to improve the performance of identified poorer performing bungs with respect to multiple needle punctures.

A first experiment involved the control of needle entry speed. Along with other associated measures, the reduction of needle engagement speed reduces secondary edge (e.g., secondary edge 904) cutting and generation of particulate. Needle engagement speeds below 30 millimeters/second (mm/sec) and even below 1 mm/sec preserve bung integrity. Typical practical needle engagement operating speeds are in the range of approximately 5 mm/sec to approximately 1 mm/sec Needle disengagement speeds may not be a major factor in bung performance. Needle disengagement speeds affect leakage during disengagement. The faster the disengagement speed the more likely leakage may occur.

Figure 10:
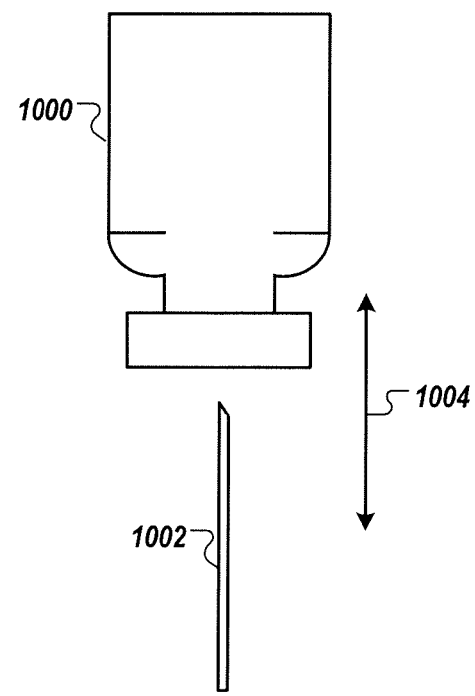
FIG. 10 is an illustration of a vial and a needle with a co-aligned axis.

FIG. 10 is an illustration of a vial 1000 and a needle 1002 with a co-aligned axis. A second experiment involved the control of needle to vial engagement angles and needle movement variations. In some implementations, the APAS operates with a co-aligned needle and vial axis with engagement movement being along the axis (e.g., direction of motion is shown by arrow 1004). Variations of the coaxial alignment improve bung puncture performance.

Figure 11:
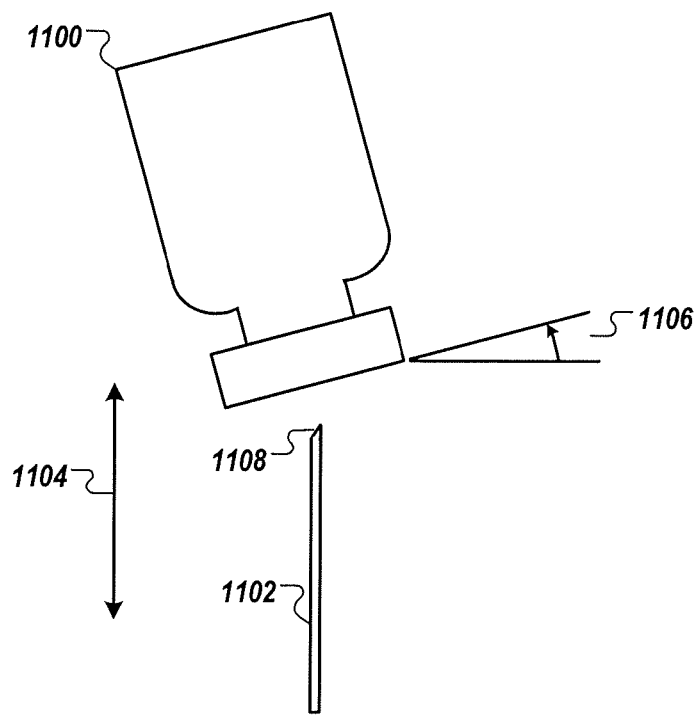
FIG. 11 is an illustration of a vial and a needle with the vial axis canted relative to the needle axis.

FIG. 11 is an illustration of a vial 1100 and a needle 1102 with the vial axis canted relative to the needle axis. The vial is canted (e.g., vial angle 1106) in the direction of a needle bevel 1108. Engagement movement of the needle 1102 into the vial 1100 is along the axis of the needle (e.g., arrow 1104 shows the direction of motion).

For example, the vial angle 1106 varies from zero degrees to 45 degrees. A vial angle 1106 of zero degrees constitutes a normal engagement case and a vial angle 1106 of 45 degrees approaches a practical upper limit. A vial angle 1106 of 50 degrees approaches the angle of the needle bevel 1108. An useful range of angles includes angles between 10 to 30 degrees. For example, a nominal vial angle is approximately 20 degrees. If the vial angle 1106 is too small, secondary edge cutting of the bung by the secondary edge of the needle (e.g., secondary edge 904 of needle 900 in FIG. 9) occurs. If the vial angle 1106 is too large, the primary edge of the needle (e.g., primary edge 902 of needle 900 in FIG. 9) slips before engagement, has difficulty engaging, and generates adverse needle sideways preload. For vial angles ranging from 15 degrees to 20 degrees, needle entry is optimized and evidence of secondary edge cutting of the bung is diminished below concern. For example, a vial angle of 20 degrees is a good compromise.

Additionally, samples of poor performing bungs were tested. Tests were performed with the vial angle set to 15 degrees and 20 degrees and the results were compared. A syringe manipulation unit included in an APAS (an example of which is shown with reference to FIG. 6 of previously incorporated by reference U.S. patent application Ser. No. 11/937,846, entitled "Control of Fluid Transfer Operations," and filed by Doherty et al. on Nov. 9, 2007) performed twenty punctures of a needle through a bung on a vial. For each test, a new needle with a syringe was loaded on the syringe manipulation unit and used for the entire test. The syringe manipulation unit repeatedly cycled the bung, mounted on the vial, onto the needle at a speed of 3 mm/sec for both engagement and disengagement. Test results for both a vial angle of 15 degrees and 20 degrees showed that bung integrity was maintained. Additionally, magnified imagery showed the bung punctured by the needle at a 20 degree angle exhibited less secondary edge scraping (e.g., scraping of the secondary edge 904 of needle 900) towards the entry point of the needle into the bung.

Vial bungs have surface features (indents) that identify puncture sites for the user. The surface features either locally increase or reduce the local entry angle of the needle into the bung. An increase in the vial angle (e.g., vial angle 1106) provides additional entry angle margin.

The techniques described for puncturing a vial with a beveled needle require accurate guidance of the needle tip into the same hole in the bung. The syringe manipulator device accomplishes accurate guidance of a needle tip into the same hole in a vial bung by using positive alignment of the needle with needle gripper fingers (e.g., example needle gripper fingers are shown with reference to previously incorporated by reference U.S. patent application Ser. No. 12/209,097, entitled "Gripper Device," and filed by Eliuk et al. on Sep. 11, 2008). The APAS accomplishes accurate guidance of a needle tip into the same hole in a vial bung by providing accurate registration of the vial top by gripping the vial directly at the top of the vial. Examples of vial gripper fingers are shown with reference to FIG. 6 of previously incorporated by reference U.S. patent application Ser. No. 11/937,846, entitled "Control of Fluid Transfer Operations," and filed by Doherty et al. on Nov. 9, 2007.

For example, a vial angle is negative (e.g., −20 degrees) and the vial is angled in a direction opposite the needle bevel. This configuration can exhibit beneficial particulate reduction. Other variations of vial angles are possible through variations of the axis of movement of the vial. Movement of the vial along the syringe axis can engage the vial without bending the needle.

Figure 12:
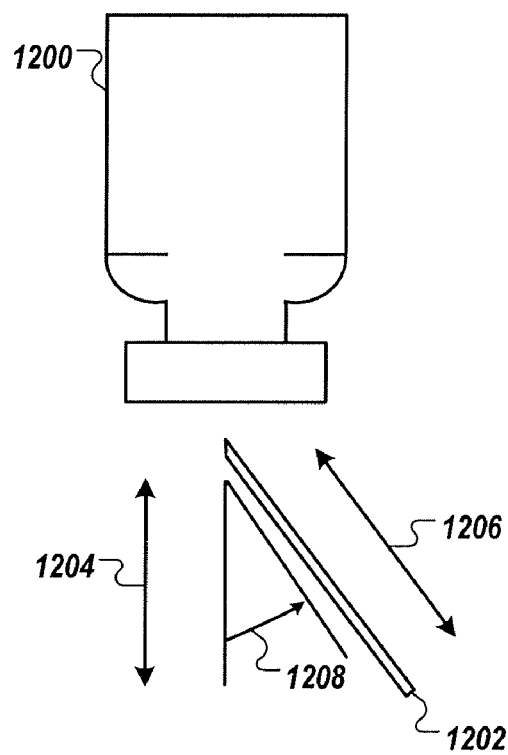
FIG. 12 is an illustration of a vial and a needle with the needle axis canted relative to the vial axis.

FIG. 12 is an illustration of a vial 1200 and a needle 1202 with the needle axis canted relative to the vial axis. The initial needle engagement motion into the vial occurs with a first movement direction (e.g., indicated by arrow 1204) of the vial parallel to the needle bevel direction. Once the needle penetrates the bung, the motion changes to a second movement direction along the needle axis (e.g., indicated by arrow 1206) to further penetrate the bung. The needle rotates through all or some portion of a needle bevel angle 1208 to align the needle and vial axes prior to a second movement.

Other example methods to improve vial puncture performance include automated control of puncture motion trajectories. A needle includes a closed distal end and a number of radially directed apertures along the needle shaft to facilitate fluid transfer through the needle.

The APAS includes an assortment of drug vials used to perform aseptic compounding of medications. The drug vials include rubber stoppers, or bungs, with a wide range of geometric features and rubber properties. The rubber properties may vary from batch to batch of drug vials.

In some experimental configurations described below, the APAS uses the needle 900 described in FIG. 9 to transfer fluids into drug vials through the vial bungs. For example, the APAS performs repeated entry of a needle through the same vial puncture site with careful control of needle position, needle bevel orientation, and needle entry speed. The APAS controls the repeated entry of a needle through the same vial puncture site by positive alignment of the needle with the needle gripper fingers, registration of the vial top by directly gripping the vial at the top of the vial and the use of a bevel orientation device. An example of a bevel orientation device is shown in FIGS. 4A-4D of the previously incorporated by reference U.S. patent application Ser. No. 11/937,846, entitled "Control of Fluid Transfer Operations," and filed by Doherty et al. on Nov. 9, 2007. Controlling the repeated entry of a needle through the same vial puncture site in this manner may yield improved bung pressure sealing (with and without needle engagement) and little or no particulate generation.

The syringe in an APAS uses one or more alternative needle designs. For example, the APAS performs one or more seal punctures of fluid ports of sealed pharmaceutical containers (e.g., IV bags, bottles, drug vials) using a needle with a closed distal end (referred to as "pencil point"). Analysis and experiments were performed that involved several tip shapes, side port geometries and point sharpness levels.

Figure 13:
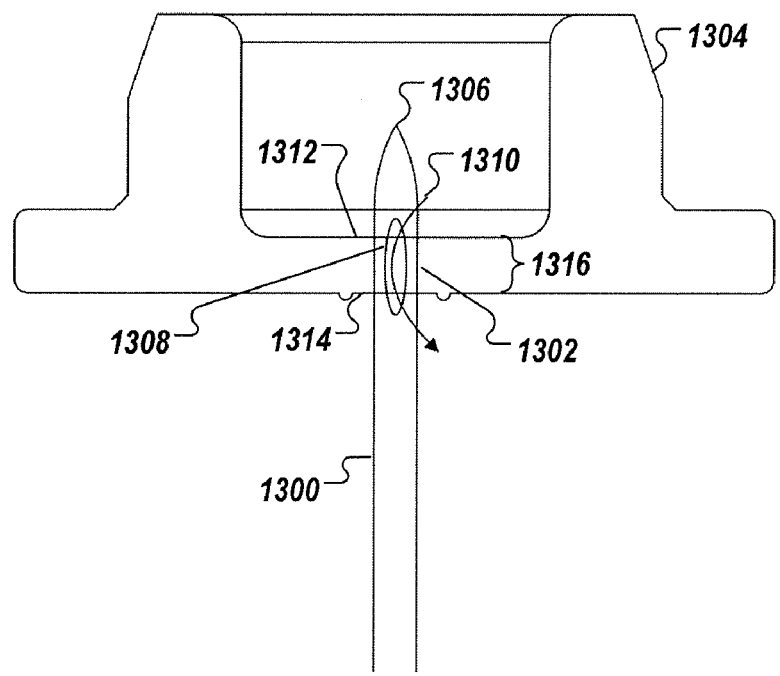
FIG. 13 is an illustration of an example pencil point needle inserted into a vial bung of a top of a vial.

FIG. 13 is an illustration of an example pencil point needle 1300 inserted into a vial bung 1302 of a top of a vial 1304. As used herein (unless otherwise indicated), a pencil point needle (e.g., pencil point needle 1300) includes a closed cone or parabolic shaped point 1306 at a distal end through which no fluid flows. The fluid path is through one or more apertures or side ports (e.g., side port 1308) located on the cylindrical portion of the pencil point needle 1300. The side ports are located as close to the point transition as possible. The vial bung 1302 acts as a stopper, preventing fluid flow from the vial but allowing needle entry into the vial.

The APAS performs one or more seal punctures of fluid ports of sealed pharmaceutical containers that involve a puncture motion trajectory using a pencil point needle. The APAS includes the capability to puncture a vial many times without causing substantial particulate, coring and/or leaks. By allowing higher puncture counts, some implementations of the APAS are able to increase the size of a container used to compound a drug. For example, the use of larger containers by the APAS simultaneously reduces the number of containers and other time and consumables required to prepare a given number of doses of a drug the APAS. The reduced operations and consumables may substantially reduce operating cost, save energy, and yield higher throughput for the APAS. The throughput gains achieved by the use of larger containers may reduce handling and may reduce the number of vial identification and disinfection processes. Furthermore, reducing degradation of the seals over repeated fluid transfer operations allows for an increase in needle size (e.g., diameter), which yields improved fluid transfer rates and may further enhance throughput.

In various embodiments, a suitable pencil point needle may not have a bevel on the distal tip of the needle (e.g., pencil point needle 1300). Therefore, the APAS may not require a bevel orientation device, which results in further improvements to throughput and reduced system cost.

The example in FIG. 13 shows a potential partial leak problem that occurs when the side port 1308 of the pencil point needle 1300 is positioned and extended to provide fluid communication (e.g., shown by arrow 1310) from an interior seal surface 1312 of the vial bung 1302 to the exterior seal surface 1314 of the vial bung 1302. Various pencil point needles can be selected with side port configurations that do not allow a fluid path when partially inserted into a vial bung. A partial leak situation occurs during a slow insertion and/or removal of the pencil point needle from the vial bung. The partial insertion leak is further compounded when coupled with a positive pressure vial with respect to ambient pressure.

The one or more side ports (e.g., side port 1308) are located the same distance from the point (e.g., point 1306) at a distal end of the pencil point needle (e.g., needle 1300). The side ports are located on the cylindrical part of the needle as close to the tangent of the distal end (e.g., the point 1306) as possible.

The location and size of the side ports are selected to prevent partial leaks. The side port of a selected pencil point needle is located and/or sized of dimensions down the length of the needle so as not to exceed the thinnest vial bung thickness. The selection of the location and/or size of the side port further includes a margin of minimum distance. The margin of minimum distance is the distance where the minimum vial bung thickness (e.g., at the point of penetration) exceeds the axial length of an individual side port (or a set of side ports) by at least a predetermined margin.

Fluid transfer rates can be increased by penetrating a needle to a depth within the pharmaceutical fluid container where more than one set of apertures is in fluid communication with the interior of the pharmaceutical fluid container (e.g., vial, IV bag). A puncture motion trajectory inserts up to four sets of four apertures into fluid communication with an interior of a vial. If the vial contains sufficient fluid, then fluid is transferred from the vial to a syringe through 16 apertures.

The APAS controller is programmed to monitor the volume of fluid remaining in the vial (e.g., by determining the initial fluid volume in the vial and the fluid volume added or withdrawn from the vial). In response to determining the volume of fluid remaining in the vial, the controller causes the APAS to perform operations to control the insertion depth of a pencil point needle. The APAS controls the penetration depth for fluid transfer operations so that all of the sets of side ports that penetrate into the interior of the vial are immersed in the fluid contained in the vial while the fluid is being withdrawn from the vial. The penetration depth of the needle within the vial is adjusted during a fluid transfer operation such that selected sets of side ports remain immersed in the fluid within the vial as the fluid level within the vial changes.

Hole chamfering and or electro polishing prevents particulate generation by the side ports. Experimental testing included three hole and four hole side port designs. For example, the tested three hole design had the holes spaced 120 degrees apart and the four hole design had the holes spaced 90 degrees apart. Side ports are fabricated using drilling, laser, electrical discharge machining (EDM), grinding and/or water jet fabrication methods.

Experimental test results were obtained for the flow rate of a typical open-ended hypodermic needle. Testing showed that the average flow rate of a typical 18 gauge needle is 3.55 cubic centimeters/second (cc/sec). By comparison, testing showed that the average flow rate of a typical 16 gauge needle is 7.72 cc/sec. Therefore, the flow rate difference between the 18 gauge needle and the 16 gauge needle is 217%. The increased flow rate is attributed to the increased inside diameter of the 16 gauge needle. Table 1 shows the nominal outer diameter (OD) dimensions, nominal inner diameter (ID) dimensions and the nominal wall dimensions for a 16 gauge and an 18 gauge needle.

TABLE 1

| Gauge | Nominal OD | Nominal ID | Nominal wall |
|---|---|---|---|
| 16 | 1.651 mm (0.0650 in.) | 1.194 mm (0.0470 in.) | 0.229 mm (0.0090 in.) |
| 18 | 1.270 mm (0.0500 in.) | 0.838 mm (0.0330 in.) | 0.203 mm (0.0080 in.) |

Experimental test results were also obtained for the flow rate of pencil point needles with side ports that included three hole and four hole side port pencil point needle designs. For example, each side port had a diameter of 0.81 millimeters (mm) (0.032 inches). The four hole side port needle design allowed a draw rate of 6.75 cc/sec of water and the three hole side port needle design allowed a draw rate of 6.00 cc/sec of water. These draw rates are compared to the flow rates of the typical 18 gauge and 16 gauge needles, which are 3.55 cc/sec. and 7.72 cc/sec., respectively. In some implementations, a 90 degree direction change of the fluid flow and/or port restriction accounts for the slightly lower overall flow rates compared to a typical 16 gauge needle.

In some implementations, a four hole side port needle is operated at the three hole side port flow rate to allow for margin. The margin may be beneficial in some applications that have the potential for partial blockages of one or more of the side ports. This allows for partial blockage of side ports without reducing the fluid flow rate.

FIG. 14 is an illustration of an example narrow fluid channel on the inside of a stopper 1400. FIG. 15 is an illustration of an example of a marginal needle height. Partial blockages result from the deformation of the stopper. The deformation of the stopper (vial bung) results from the negative vial pressure causing stopper concavity.

For example, a point at the distal tip of a pencil point needle is shaped to have a small radius (a dull point) rather than being ground to a sharp point. A pencil point needle that includes a dull point is beneficial when taking into account the tolerance of the needle and the positioning of a vial with respect to the needle.

FIG. 16 is an illustration of an example misalignment of a needle with a previous puncture hole 1600. If the needle and vial are not substantially precisely aligned and there has already been a puncture (e.g., previous puncture hole 1600) into the stopper (e.g., a rubber stopper or vial bung) of the vial from a previous operation, then the dull point of the needle will push up on the stopper slightly in a subsequent puncture into the stopper. The push up of the dull point of the needle on the stopper deforms the rubber and makes the previous puncture hole available to the needle. Therefore, the same puncture hole is found and reused with substantially no cutting of the stopper or particulate generation. In comparison to a needle with a sharp point, a needle with a dull point generally requires a higher insertion force on the previous puncture hole in order to reuse the previous puncture hole.

The degree of dullness of the point of the needle is a measure of the radius of the point. For example, typical point radii are 0.00254 mm to 0.254 mm (0.0001 inches to 0.01 inches) but could extend to a hemispherical point. Additionally, there is a practical limit to the dullness of the point. At a certain measured dullness the point of the needle may not cut a path through the stopper on a first puncture. The point of the needle may instead push a plug or core through the stopper creating undesirable particulate and a large leak pathway. For example, suitable point radii for a 16 gauge needle includes radii in the range from 0.0254 mm to 0.381 mm (0.001 inches to 0.015 inches).

A needle with a sharp point achieves a low insertion force, which substantially reduces or eliminates any need for lubrication. The points of some needles are sufficiently sharp and tend to create a new puncture hole in a stopper if the point of the needle is not substantially precisely aligned with a previous puncture hole. The generation of additional new puncture holes in the stopper results in the increased likelihood of coring, particle generation and leaks.

In addition to the shape of the point of the needle, the penetration or plunge velocity on the needle into the stopper plays a role in allowing an offset or slightly misaligned needle to go through a previous puncture path and hole. If the plunge velocity of the needle is too high and the needle is misaligned with respect to the stopper, the needle creates a new puncture hole in the stopper. Creating new puncture holes in close proximity to previous puncture holes elevates the chances of particle generation.

Reduction of the needle engagement speed reduces point cutting of the stopper and generation of particulate. Experiments using engagement speeds in the range of 300 mm/sec to 30 mm/sec indicate that engagement speeds below 30 mm/sec, down to 1 mm/sec and below, can preserve vial bung integrity. Slower engagement speeds allow the point of the needle time to locate a previous puncture hole. In order to achieve this alignment, suitable practical operating engagement speeds are in the range of 5 mm/sec to 1 mm/sec. Disengagement speeds may affect leakage during disengagement but are not a major factor in determining bung integrity.

The shape of the point of the needle contributes to the success of the pencil point needle finding a previous puncture hole. Experiments suggest that, in general, the blunter the cone (the point of the needle), the more likely the needle will be able to find a previous puncture hole. However, a needle that has a long, tapered point performs a first puncture through a vial bung using lower insertion forces than a needle with a blunter cone.

Figure 17:
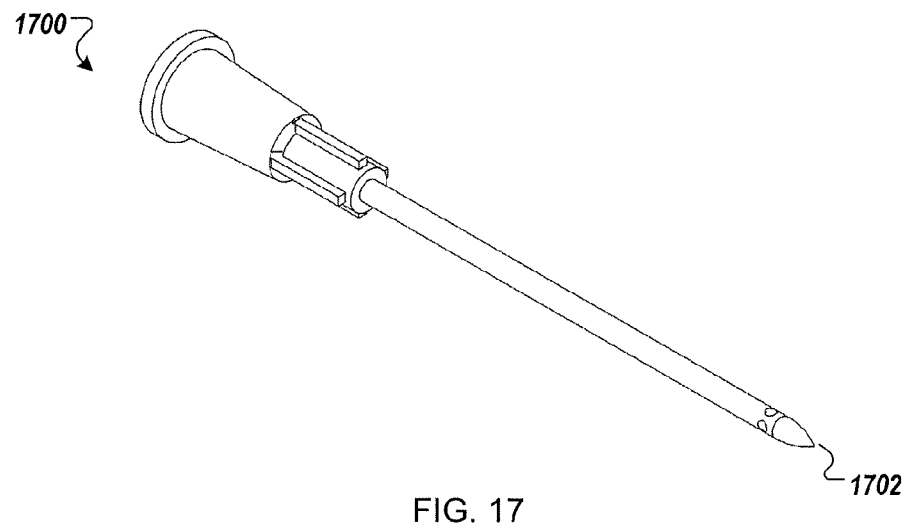
FIG. 17 is an illustration of an example needle with a long point.

FIG. 17 is an illustration of an example needle 1700 with a long point 1702. The length of the tip of the needle is a factor when engaging medical containers such as IV bags. If the tip of the needle is too long, side punctures of the container occur depending on how the container is held during the engagement of the needle into the container.

Figure 18:
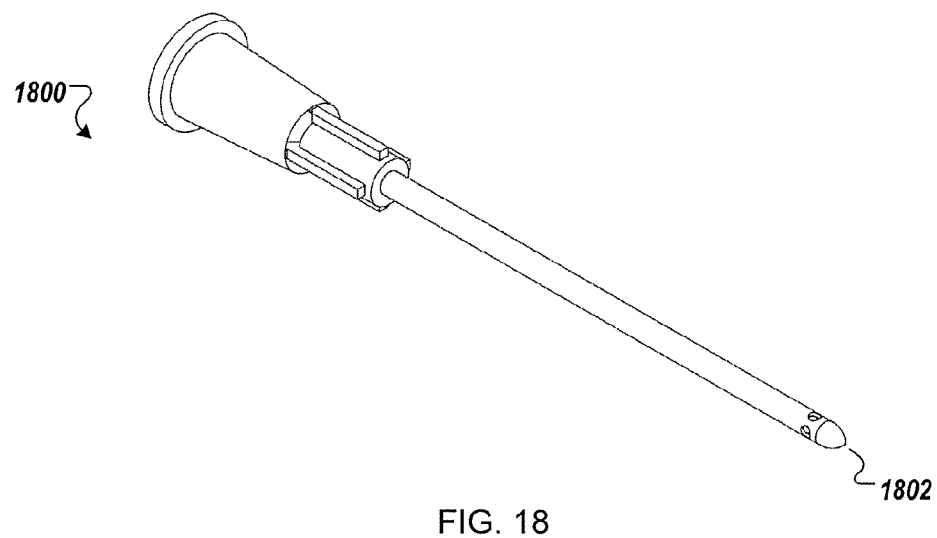
FIG. 18 is an illustration of an example needle with a short point.

FIG. 18 is an illustration of an example needle 1800 with a short point 1802. For example, needle diameter to needle point length ratios of 3:1 to 1:3 occur. Typical examples of needle diameter to needle point length ratios are a 0.1651 mm (0.065 inch) diameter to 0.3048 mm (0.120 inch) tip length or a 0.1651 mm (0.065 inch) diameter to 0.1778 mm (0.070 inch) tip length.

Lubrication is an additional factor that enables the needle to follow a previous puncture path to engage in a previous puncture hole. Lubrication reduces the friction between the needle point and the seal member (the stopper or vial bung) material (e.g., rubber) making the previous puncture path easier to follow. The composition of the lubricant used is consistent with the composition of the lubricant used on typical sterile needle. Lubrication and the selection of the shape of the point of the needle enables the user the option to increase the gauge of the needle used in the APAS without incurring any damage to the stopper of a vial.

The repeated precise placement of the needles of multiple syringes into the bungs of multiple vials can be problematic, especially when a vial is placed in storage between fluid transfer operations. Tolerances associated with the items (e.g., containers, vials, syringes) and the equipment handling those items (e.g., syringe manipulators, robotic manipulators) impedes absolute precision. Some misalignment (which may be referred to herein as "wander") occurs between the needle and the existing puncture hole in a stopper. To minimize needle wander, a syringe manipulator device includes positive alignment of the needle with needle gripper fingers. The syringe manipulator device includes substantially precise registration of the vial top by directly gripping the vial at the top of the vial. Additionally, the APAS includes a bevel orientation device to index the needle bevel.

In an experiment, a needle wander width of 0.25 mm (0.01 inches) was measured using an 18 gauge blunt fill needle made by BD. Using the 18 gauge blunt fill needle made by BD that exhibited a needle wander width of 0.25 mm (0.01 inches), additional experiments showed that some stoppers produced particulate, backside coring, and leaks within eight to nine punctures.

For comparison, an experiment was performed using a 16 gauge pencil point needle. In the experiment, the APAS performed positive alignment of the needle with the needle gripper fingers. The APAS also performed precise registration of the vial top by directly gripping the vial at the top of the vial. However, the APAS did not use the bevel orientation device. In the experiment, 50 hole punctures were performed through the stopper. Observation of the stopper indicated the appearance of a single puncture hole.

Continuing with the experiment, the same stopper was reset and shimmed to induce a total needle wander width of 0.45 mm (0.18 inches). The APAS performed 40 additional hole punctures, ten in each quadrant of the stopper. After a total of 90 punctures into a worst case stopper both the outer and inner puncture holes appeared as a single puncture hole. Additionally, the stopper exhibited little or no evidence of particulate or cutting. This experiment demonstrated that the pencil point needle followed the original puncture hole each time a puncture was performed, despite the induced offset to simulate wander.

In accordance with the above-described apparatus and related methods, an example process for providing a needle puncture of a medical container in a robotic cell includes repeatable alignment and positioning of a pencil point needle, and may further include controlled penetration speeds and depths based on seal thickness.

FIGS. 19A-19B show a needle puncture into a stopper on a vial prior to needle entry into the vial. FIGS. 20A-20B show a needle puncture into a stopper on a vial after needle entry into the vial. FIG. 19A shows a 16 gauge needle 1900 ready for injection (ready to puncture a hole in stopper 2002). FIG. 19B shows the shape of the typical deformation of the stopper 1902 during the first puncture of the needle 1900 into the stopper 1902. FIG. 20A shows the shape of the stopper 1902 after the needle 1900 breaks through the stopper (creates a puncture hole through the stopper 1902). As shown in FIG. 20A, the stopper "snaps" back into its original shape (the position of the stopper 1902 in FIG. 19A). The fast action of the stopper snapping back to its original shape allows for the quick passing of the one or more side ports (e.g., side port 2004) though the rubber minimizing the opportunity for leaks. FIG. 20B shows the needle 1900 retracted in order to draw fluid from the vial. However, due to the increased plunge depth required to ensure needle penetration, the needle is retracted to bring the one or more side ports (e.g., side port 2004) in substantially close proximity to the inside surface of the stopper in order to draw all of the fluid from the vial.

Figure 21A:
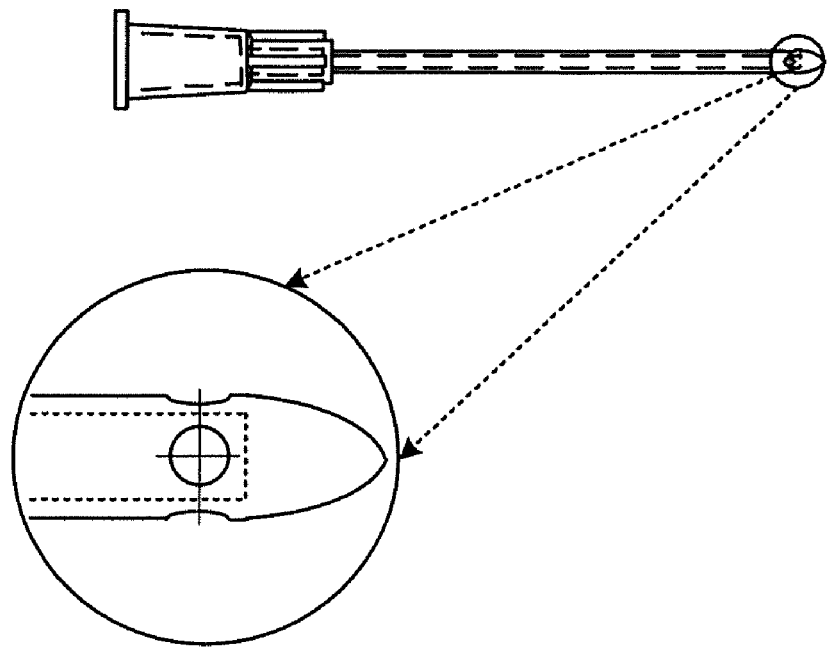
FIGS. 21A-21L are illustrations of example pencil point needles that can be used in an APAS.
Figure 21B:
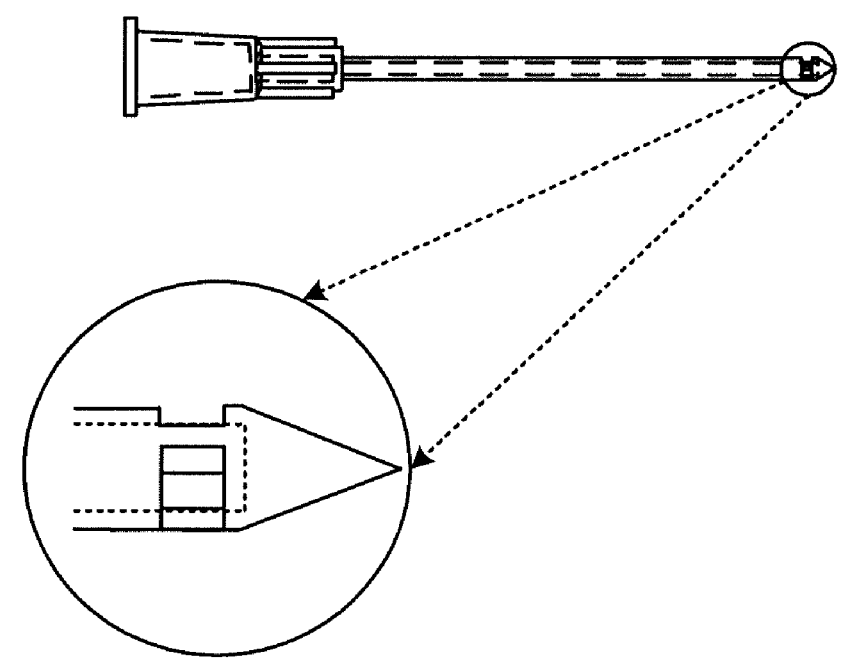
Figure 21C:
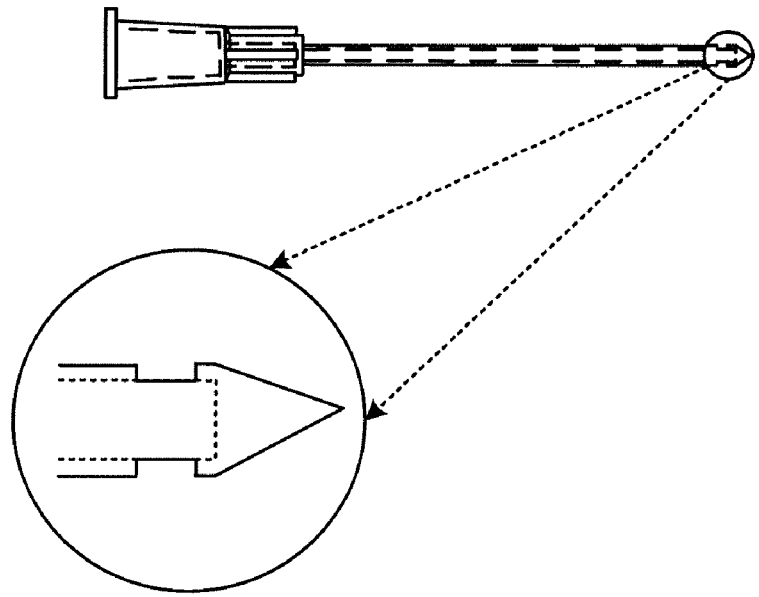
Figure 21D:
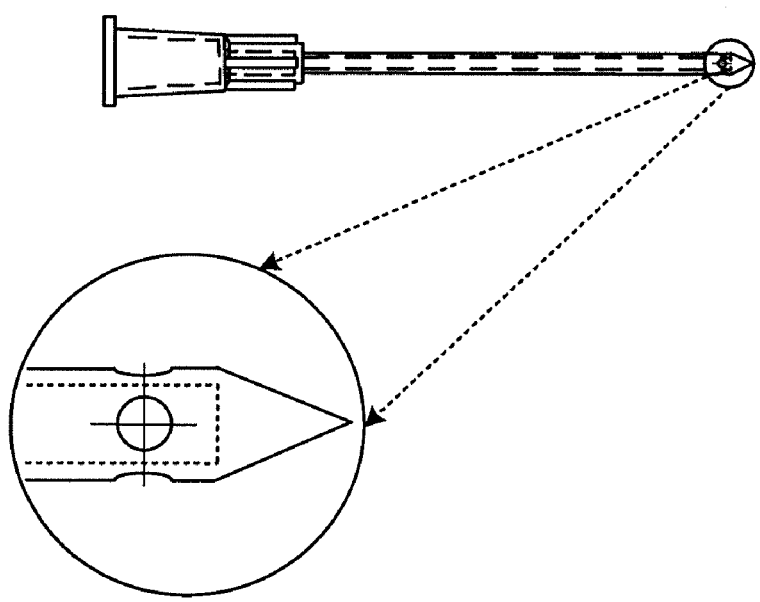
Figure 21E:
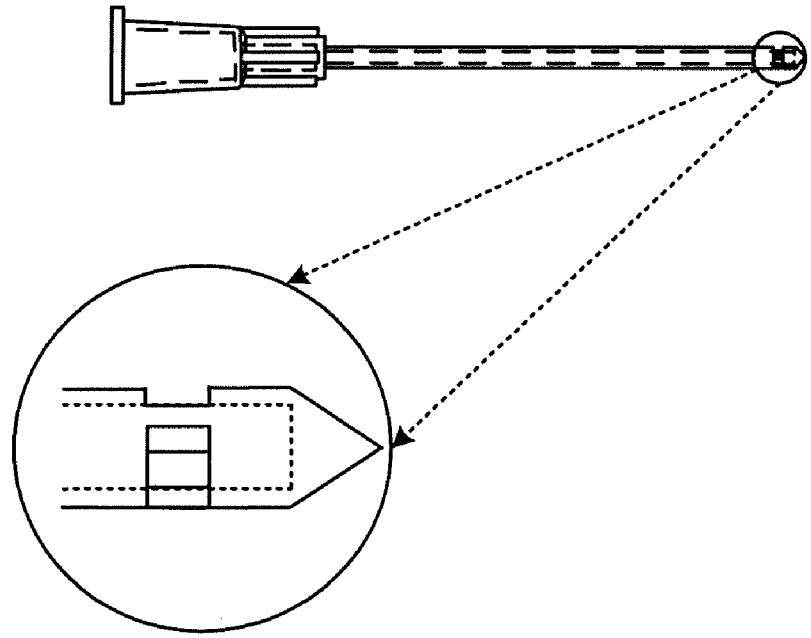
Figure 21F:
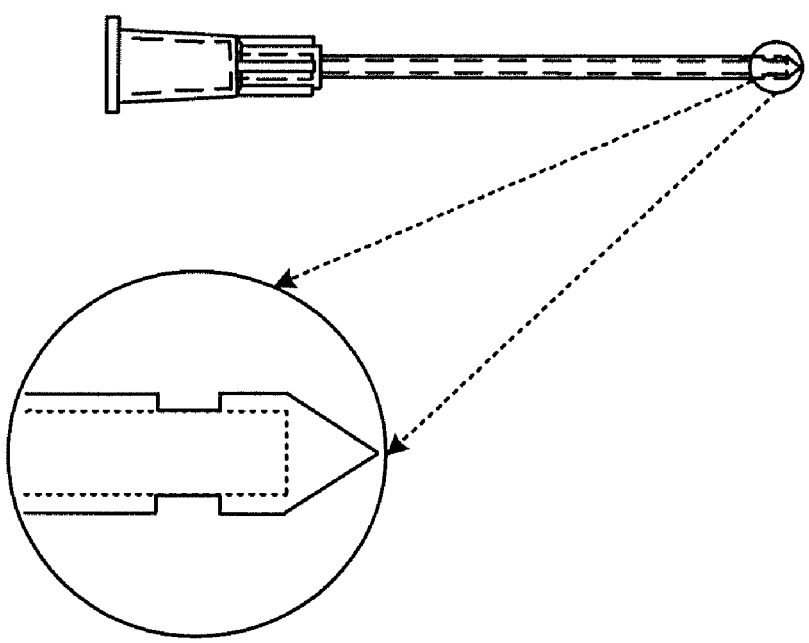
Figure 21G:
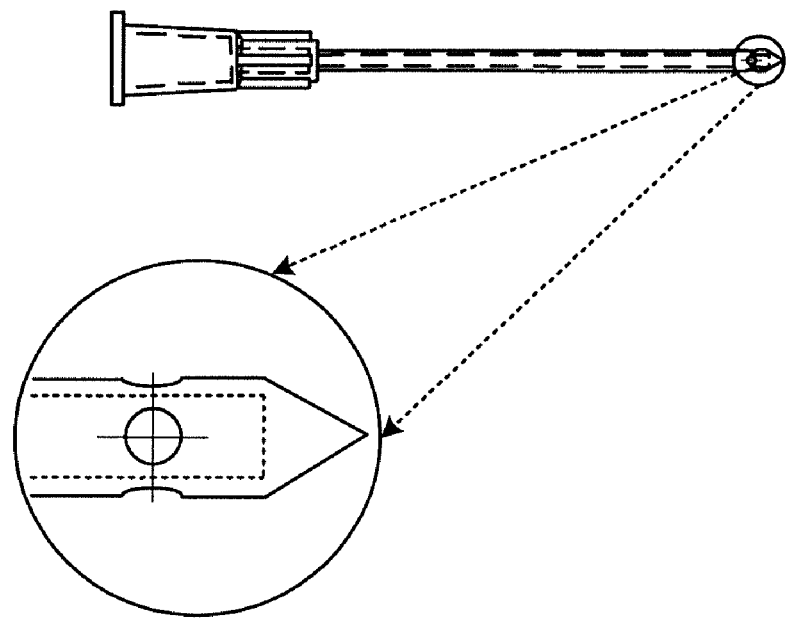
Figure 21H:
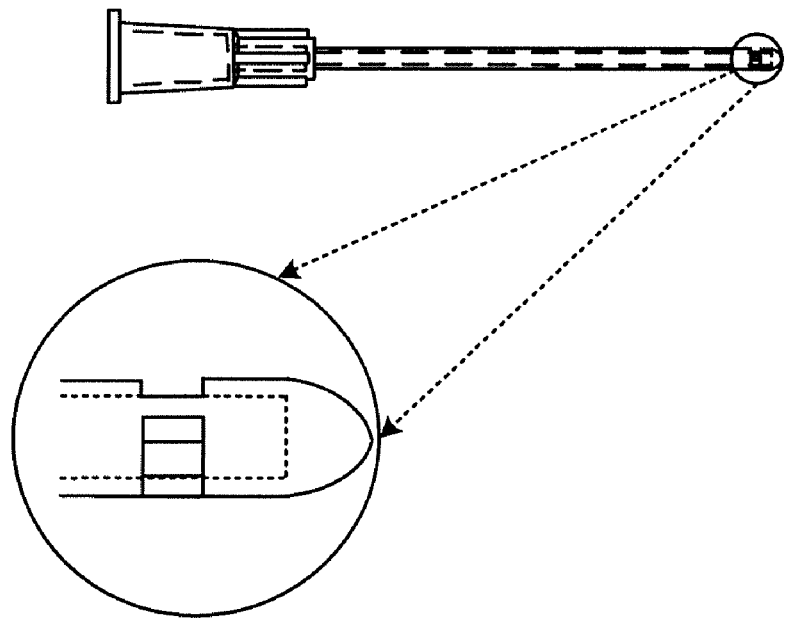
Figure 21I:
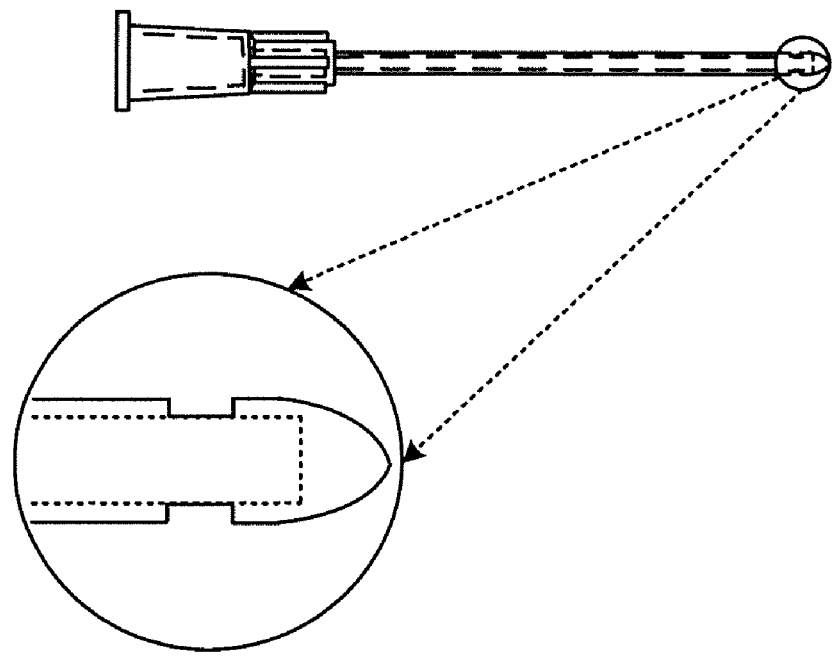
Figure 21J:
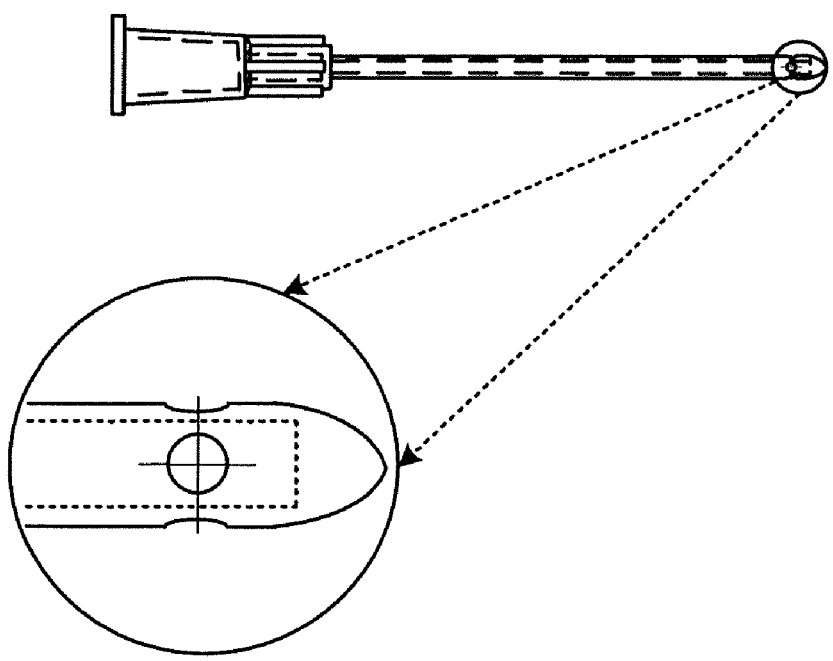
Figure 21K:
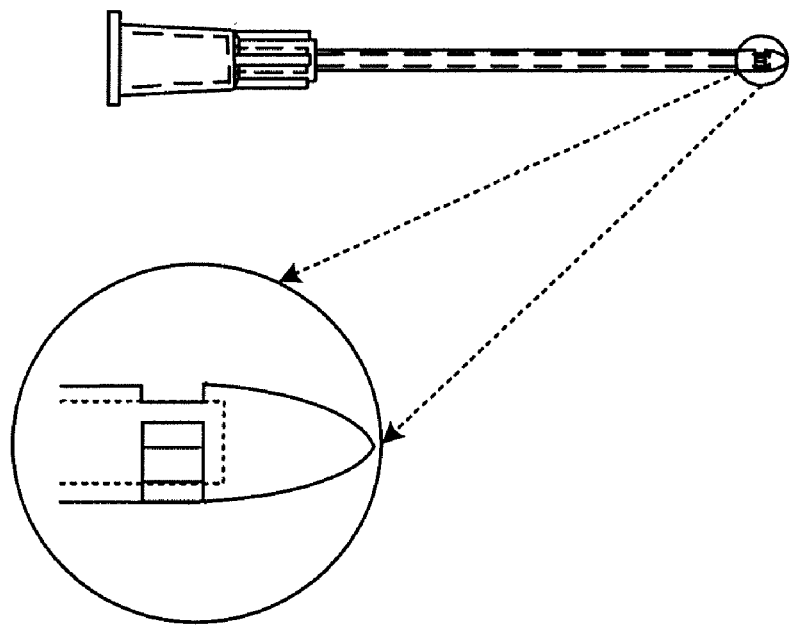
Figure 21L:
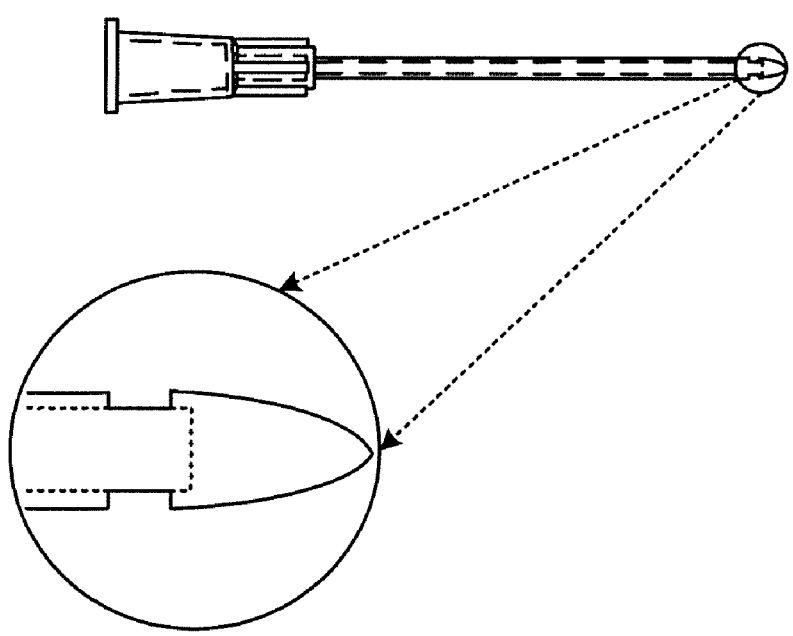
Figure 22:
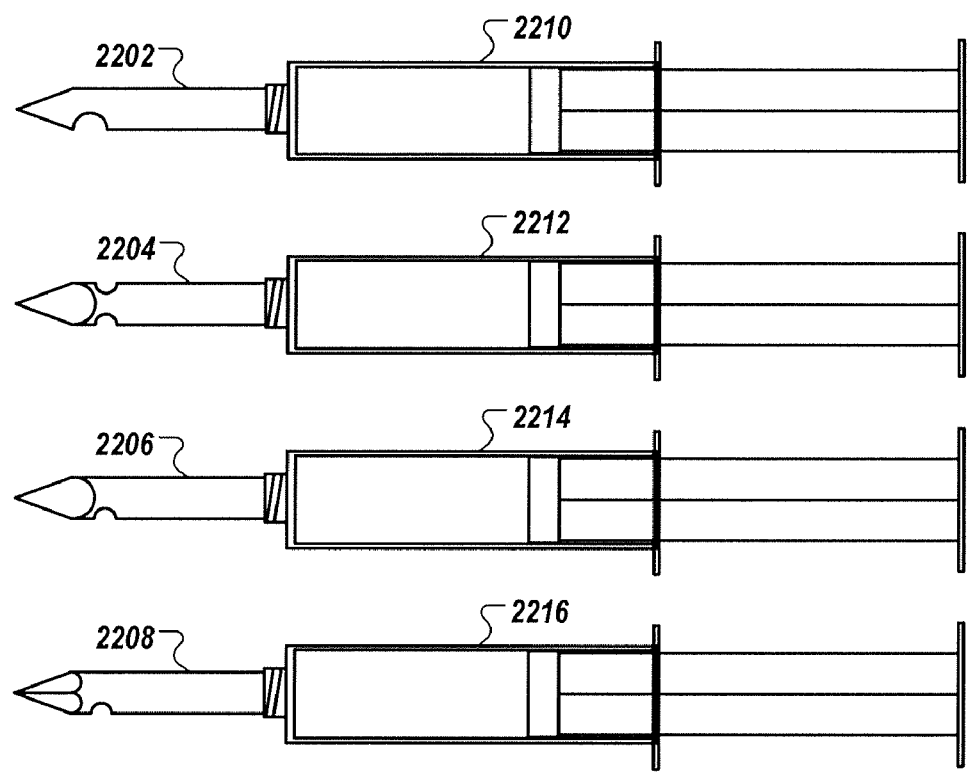
FIG. 22 is an illustration showing example pencil point needles with side ports.

FIGS. 21A-21L are illustrations of example pencil point needles that are used in an APAS. FIG. 21A is an illustration of a proto-type 1, 16 gauge needle. FIG. 21B is an illustration of a proto-type 12, 16 gauge needle. FIG. 21C is an illustration of a proto-type 11, 16 gauge needle. FIG. 21D is an illustration of a proto-type 10, 16 gauge needle. FIG. 21E is an illustration of a proto-type 9, 16 gauge needle. FIG. 21F is an illustration of a proto-type 8, 16 gauge needle. FIG. 21G is an illustration of a proto-type 7, 16 gauge needle. FIG. 21H is an illustration of a proto-type 6, 16 gauge needle. FIG. 21I is an illustration of a proto-type 5, 16 gauge needle. FIG. 21J is an illustration of a proto-type 4, 16 gauge needle. FIG. 21K is an illustration of a proto-type 3, 16 gauge needle. FIG. 21L is an illustration of a proto-type 2, 16 gauge needle. FIG. 22 is an illustration showing example pencil point needles 2202, 2204, 2206, 2208 attached to syringe barrels 2210, 2212, 2214, 2216, respectively, where the pencil point needles 2202, 2204, 2206, 2208 include side ports.

Figure 23A:
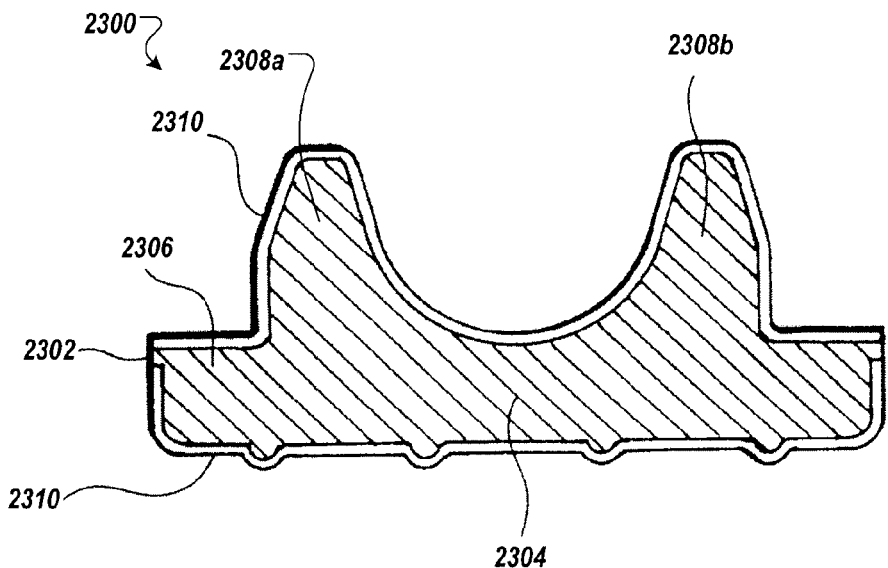
FIG. 23A is an illustration of an example vial bung (stopper) that can be used in implementations and embodiments described herein.

FIG. 23A is an illustration of an example vial bung 2300 (stopper) that is used in implementations and embodiments described herein. The vial bung 2300 includes a rubber stopper body 2302, a top part 2304, a flange part 2306, legs 2308*a*, 2308*b* and laminated layer 2310.

Figure 23B:
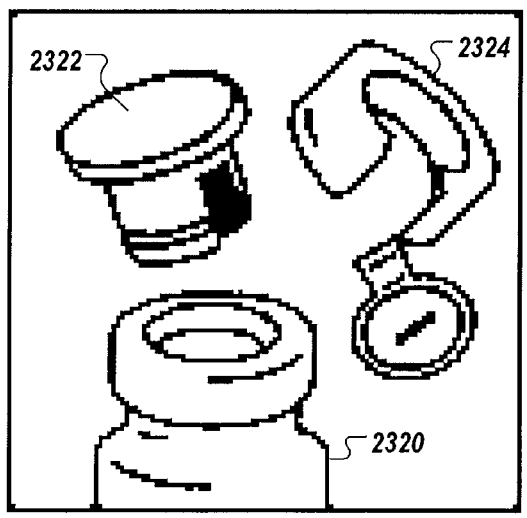
FIG. 23B is an illustration of an example vial with a bung and a vial seal.

FIG. 23B is an illustration of an example vial 2320 with a bung 2322 and a vial seal 2324. The vial seal 2324 maintains the bung 2322 in place in the vial 2320.

Figure 23C:
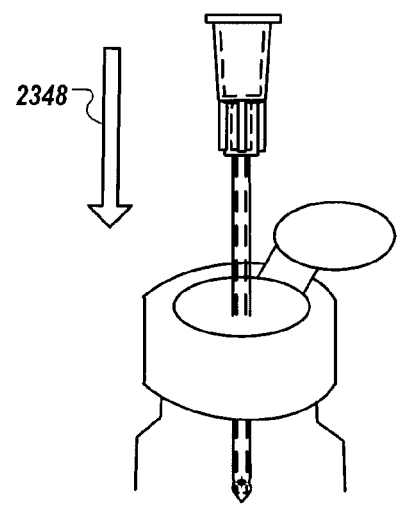
FIG. 23C is an illustration of an example vial with a bung sealed to a vial with a vial seal.

FIG. 23C is an illustration of an example vial 2340 with a bung 2342 sealed to the vial 2340 with a vial seal 2344. FIG. 23C also shows an example needle 2346 that has punctured the bung 2342 where the vial 2340 and the needle 2346 are co-aligned. The engagement movement for the needle 2346 into the vial 2340 is along the co-aligned axis (e.g., direction of motion is shown by arrow 2348).

Figure 24:
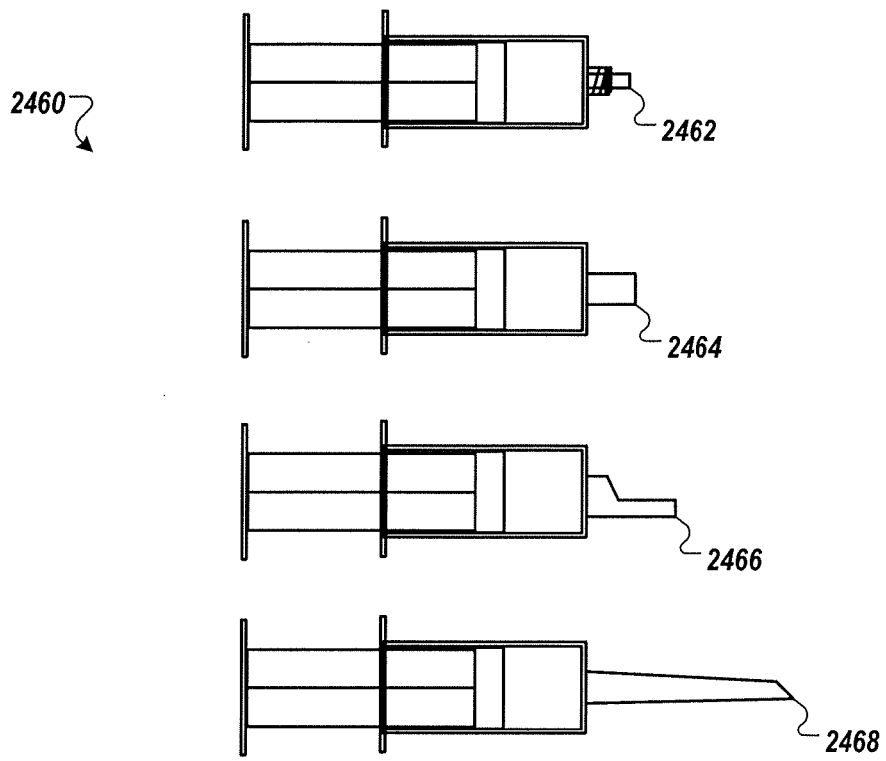
FIG. 24 is an illustration of example syringe barrels.

FIG. 24 is an illustration of example syringe barrels 2460. A syringe barrel includes a syringe tip. The syringe tip is secured to the barrel of the syringe. Syringe tips can include, but are not limited to, a luer lock tip 2462, a slip tip 2464, an eccentric tip 2466 and a catheter tip 2468.

Figure 25A:
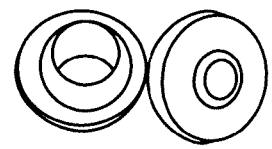
FIGS. 25A-C are illustrations of example vial bungs.
Figure 25C:
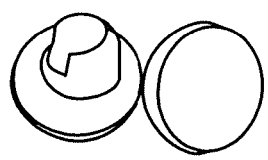
Figure 25B:
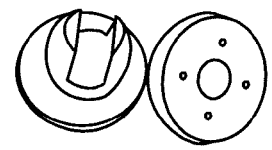

FIGS. 25A-C are illustrations of example vial bungs. The vial bungs are rubber stoppers with a wide range of rubber properties. As shown in FIGS. 25A-C, the vial bungs include a wide range of geometric features. The vial bungs are available in a wide range of geometric shapes and sizes dependent, for example, on the size and shape of the vial opening it will be placed into.

Vial bungs may have surface features (indents) that identify puncture sites for the user. In some cases, the surface features either locally increase or reduce the local entry angle of the needle into the bung. An increase in the vial angle (e.g., vial angle 1106) may provide additional entry angle margin.

The needle-syringe interface comprises a luer lock or other suitable connection. For example, the needle-syringe interface includes a slip tip onto which the needle slides without engaging threads. To facilitate automated robotic handling, including needle cap removal, the shape of the luer is configured such that an opposed gripper clamps onto the luer and rotates to unscrew and remove the needle. The needle cap is made so the needle is protected and the cap is rigid enough for an opposed gripper to grip it without squeezing it onto the enclosed needle.

In some implementations, an example system (e.g., an APAS) performs a number of draws from a container such as a vial by using a pattern of insertions distributed among various aperture locations. In some example modes, a pattern includes controlling some needle insertions to use previously created apertures. The example mode is further controlled so that any one of a set of apertures receives no more than one more insertion than any other aperture in the set of apertures. In some other modes, the pattern includes creating up to a predetermined number, density, or arrangement of substantially separated apertures without using any previously created apertures. In one example application, an example system makes a first sequence of cannula and/or needle insertions into a fluid transfer port using a first mode in which each aperture is substantially spaced apart from previously created apertures, and then makes a subsequent sequence of cannula and/or needle insertions using a second mode in which insertions are substantially evenly distributed among existing apertures.

In some examples, more than one size, shape, or type of needle or cannula is inserted into a particular fluid port. In an example system (e.g., an APAS), information about each needle or cannula is tracked and associated with the orientation, location, and/or angle of insertion into the fluid port. Such an example system selects a most suitable pre-existing aperture for a proposed needle or cannula to re-use.

In one example application, a system (e.g., an APAS) tracks and controls the location, orientation, and type of apertures created and the number of insertions in each aperture. The system obtains fluid port characteristics, such as the usable area of the fluid port, by recalling stored characteristic information from a database, reading the characteristic information from a label, or, for example, optical scanning (e.g., infrared, optical recognition) to identify suitable regions for insertion. The system further determines whether particular locations within the determined suitable regions are suitable for inserting a particular needle or cannula. The system further manages the location, orientation, and number of insertions of each needle or cannula type, shape, or size in each aperture.

The example system rejects a particular insertion for any of a number of reasons. The system determines that a particular aperture has been used a predetermined maximum number of times. The system determines that a particular insertion would cause the corresponding aperture to come too close (e.g., within a predetermined keep-out region) of another planned or pre-existing aperture. In some cases, the system determines the needle or cannula to be of a different shape (e.g., radius of curvature, bevel length), or size (e.g., diameter, thickness), which expands the aperture more than a desired amount. If no suitable aperture is determined to be available for the proposed needle, the system rejects the requested needle insertion.

For example, the system (e.g., an APAS) determines that the fluid port has apertures that have less than a specified maximum number of insertions in at least one aperture, and/or the fluid port has room available for receiving at least one more new aperture. Upon determining that a suitable needle or cannula type is available, the system automatically process the requested insertion using the needle or cannula type determined to be suitable. In a particular example, the system identifies a suitable inventory item, retrieves the identified item, and orients the item to achieve the desired aperture location and orientation upon insertion into the fluid port. In some examples, the orientation is based on the stored location, type, and orientation information about a pre-existing or planned aperture in the fluid port.

If no suitable needle or cannula type is available, then the system generates an appropriate electronic error message, which it then saves in an electronic data store, and/or sends the message to notify an operator. The system may further remove the container with the exhausted fluid port from process inventory.

Queue Priority

An example of a batch mode of operation for an APAS is described with reference to FIG. 18 of previously incorporated by reference U.S. Pat. No. 7,610,115, entitled "Automated Pharmacy Admixture System (APAS)," and filed by Rob et al. on Dec. 22, 2005.

FIG. 26 is a flow chart of an illustrative batch mode 2600 of operation that is used to fill drug orders provided to the APAS. The batch mode 2600 involves the loading of the inventory chamber with a plurality items that include, but are limited to, input drugs, diluents, syringes and IV bags for output doses to produce a pre-defined set of drug orders. In an illustrative example, a pre-defined set of drug orders are for a specific day. An operator prepares a master daily prep list in step 2602, which is a list of all the drug orders that the APAS needs to for the specific day. The master daily prep list includes one or more prescriptions of a particular type or one or more prescriptions of a variety of types. The operator loads the master daily prep list, in whole or in part (e.g., dependent on the size of the list), into the APAS as the run list in step 2604

The APAS controller uses the run list to prepare the drug orders. Software in the APAS screens the drug orders in the run list to ensure that the APAS is trained to fill them. The APAS controller identifies the inventory required to fill the drug orders and the inventory rack configurations for the inventory from those available. The APAS controller prepares a load list in step 2606 to guide the operator through the loading of the inventory into the inventory racks. The load list displays a list of racks into which the inventory can be loaded, as well as a schematic diagram of each rack. The inventory includes the drugs and diluents needed to prepare the orders. For example, the inventory (the drugs and diluents) is contained in vials, syringes, or IV bags. Additionally, the inventory includes syringes (e.g., with needles fitted) required for processing the orders and the output containers for the drug doses. The output containers for the drug orders include syringes or IV bags. For the case in which the inventory required to fill a drug order is already on the inventory racks, the identified inventory required is reduced or removed, and the APAS utilizes the previously loaded inventory to prepare the drug orders. For cases in which all the inventory required to fill all drug orders is in the APAS, the steps 2608 and 2610 are skipped. From the load list, the operator obtains stock from clean room inventory in step 2606, and loads the inventory racks offline in step 2610 with the stock in the positions on the inventory racks as indicated by the load list.

The operator delivers the inventory racks to the inventory chamber. The operator follows an inventory loading process as described in FIG. 4, of previously incorporated by reference U.S. Pat. No. 7,610,115, entitled "Automated Pharmacy Admixture System (APAS)," and filed by Rob et al. on Dec. 22, 2005. The operator unloads empty inventory (or unused inventory) in step 2612 that may be in inventory racks in the inventory carousels from a prior drug order run. The operator unloads waste containers in step 2614. The operator empties the waste containers in preparation for the upcoming drug order run. The waste containers are contained below the waste chutes 333, described in FIG. 3 of previously incorporated by reference U.S. Pat. No. 7,610,115, entitled "Automated Pharmacy Admixture System (APAS)," and filed by Rob et al. on Dec. 22, 2005. The waste containers hold one or more empty containers (e.g., used or empty syringes, bags, or vials) used by the APAS.

Next, in the inventory loading process as described in FIG. 4 of previously incorporated by reference U.S. Pat. No. 7,610,115, entitled "Automated Pharmacy Admixture System (APAS)," and filed by Rob et al. on Dec. 22, 2005, the operator loads the inventory racks in step 2616 onto the inventory carousels. The operator begins the batch process by setting the APAS to RUN in step 2618. The operator selects the RUN button on a touch screen flat panel monitor 202 in FIG. 2 of previously incorporated by reference U.S. Pat. No. 7,610, 115, entitled "Automated Pharmacy Admixture System (APAS)," and filed by Rob et al. on Dec. 22, 2005). The APAS runs autonomously in step 2620, generating the output orders, which depending on the drug container, are dropped into the syringe discharge chute 332 or the IV bag discharge chute 344, which are described with reference to FIG. 3 of previously incorporated by reference U.S. Pat. No. 7,610,115, entitled "Automated Pharmacy Admixture System (APAS)," and filed by Rob et al. on Dec. 22, 2005. A receptacle disposed beneath each chute collects the output containers. A pharmacy staff member takes the output away in step 2622 to be placed in inventory, for example, in a hospital ward.

The APAS continues to run and prepare the batch drug orders until the batch order run is complete in step 2624. The APAS generates a signal to inform the operator of the completion of the batch order run. The APAS informs the operator by displaying a message on a flat panel monitor serving as the input/output device 306, which is described with reference to FIG. 3 of previously incorporated by reference U.S. Pat. No. 7,610,115, entitled "Automated Pharmacy Admixture System (APAS)," and filed by Rob et al. on Dec. 22, 2005. In some implementations, compounding operations cease if all pending orders are complete, or if the inputs required to complete any pending orders are not available on the inventory racks. In other implementations, the APAS operates autonomously in a "lights out" mode, substantially without operator intervention, to process orders using available inventory.

Referring again to step 2604, the operator loads the master daily prep list, in whole or in part (e.g., dependent on the size of the list), into the APAS as the run list. For example, a user creates a queue of orders via a graphical user interface displayed on a touch screen flat panel monitor (e.g., monitor 202 in FIG. 2 of previously incorporated by reference U.S. Pat. No. 7,610,115, entitled "Automated Pharmacy Admixture System (APAS)," and filed by Rob et al. on Dec. 22, 2005) or via a remote user station (e.g. RUS 206 in FIG. 2 of previously incorporated by reference U.S. Pat. No. 7,610,115, entitled "Automated Pharmacy Admixture System (APAS)," and filed by Rob et al. on Dec. 22, 2005). The user adds a drug order, multiple identical drug orders, or an intermediate bag order as described in FIGS. 3-9. Drug orders are entered by specifying a drug, a dose quantity, a dispensing item type (e.g., syringe or bag), a drug concentration, a quantity and further dilution diluent. Intermediate bag orders are entered by specifying a drug, a diluent, a bag type and a quantity.

The APAS controller arranges multiple drug orders into a queue. In some implementations, the user assigns the priority of the drug orders in the queue. In other implementations, the priority of the drug orders are determined by the APAS controller for optimization purposes. The queue may be saved for future reuse, and identified by its name.

Alternatively, to load a master daily prep list in the step 2604, a user creates one or more patient specific drug orders on a file transfer protocol (FTP) server. A user commands the APAS controller to poll the FTP server for the drug order files. The APAS controller organizes the orders into production queues, and the user reviews and edits the queues, including moving orders from one queue to another.

An example of an on-demand mode of operation for an APAS is described with reference to FIG. 19 of previously incorporated by reference U.S. Pat. No. 7,610,115, entitled "Automated Pharmacy Admixture System (APAS)," and filed by Rob et al. on Dec. 22, 2005.

Figure 27:
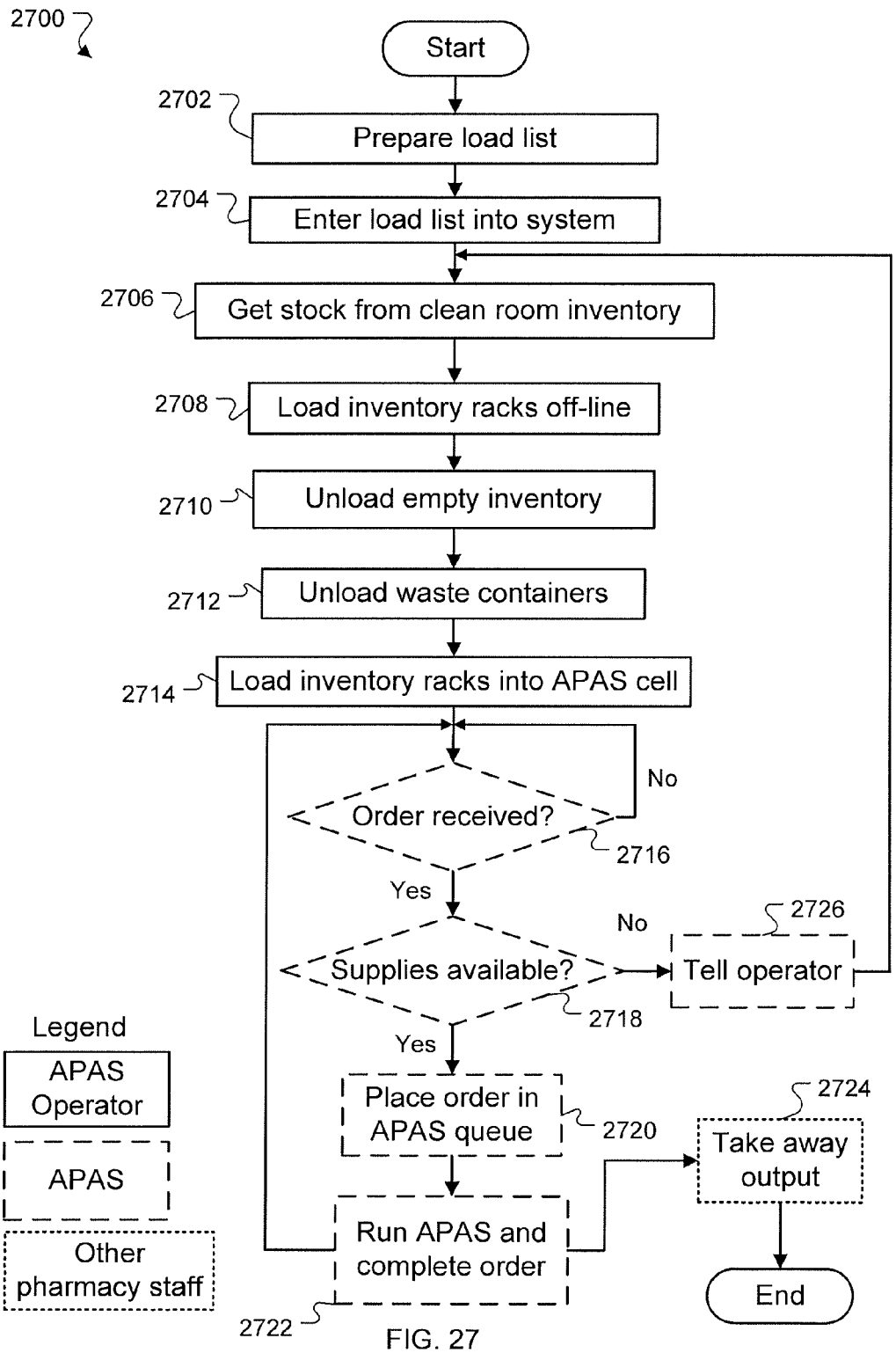
FIG. 27 is a flow chart of an on-demand mode of operation that may be used to fill orders provided to the APAS.

FIG. 27 is a flow chart of an on-demand mode 2700 of operation that is used to fill orders provided to the APAS. The on-demand mode 2700 involves loading the inventory racks with a plurality items that include, but are limited to, input drugs, diluents, syringes and IV bags for output doses to produce drug orders that constitute the most common drugs used on a given day. The APAS controller prepares a load list in step 2702 to guide an operator through the loading of the inventory into the inventory racks. A total set of drug orders to be filled is captured from an order entry system or manually entered by the operator. By analyzing the total set of drug orders to be filled, the APAS controller determines an aggregate number of drugs, syringes, vials and IV bags required to fill the total set of drug orders. The remote user station provides an aggregate list to the operator. The operator selects the drugs, syringes, vials and IV bags required from current inventory to meet the APAS load requirements for the total set of drug orders. The inventory needed includes a complement of drugs and diluents, which are contained in vials, syringes, or IV bags. Additionally, the inventory needed includes an output container for the drug dose (e.g., a syringe or IV bag). The operator enters the load list into the APAS in step 2704 using, for example, the flat panel monitor 202 as described in FIG. 2 of previously incorporated by reference U.S. Pat. No. 7,610,115, entitled "Automated Pharmacy Admixture System (APAS)," and filed by Rob et al. on Dec. 22, 2005. From the load list, the operator gets stock from clean room inventory in step 2706. The operator loads the inventory racks offline in step 2708 with the stock in the positions on the inventory racks as indicated by the load list.

The operator delivers the inventory racks to the APAS. The operator then follows an inventory loading process as described in FIG. 4 of previously incorporated by reference U.S. Pat. No. 7,610,115, entitled "Automated Pharmacy Admixture System (APAS)," and filed by Rob et al. on Dec. 22, 2005. The inventory process involves first unloading empty inventory (or unused inventory) in step 2710 that are included on the inventory carousels from the prior day's operations. The operator unloads waste containers in step 2712 and empties the waste containers in preparation for the day's orders. The waste containers are below the waste chutes 333, described in FIG. 3 of previously incorporated by reference U.S. Pat. No. 7,610,115, entitled "Automated Pharmacy Admixture System (APAS)," and filed by Rob et al. on Dec. 22, 2005. The waste containers hold empty containers used by the APAS. Next, in the inventory loading process as described in FIG. 4 previously incorporated by reference U.S. Pat. No.

7,610,115, entitled "Automated Pharmacy Admixture System (APAS)," and filed by Rob et al. on Dec. 22, 2005, the operator loads the inventory racks in step 2714 onto the inventory carousels.

The APAS waits to receive drug orders, in step 2716. The APAS receives drug orders from the hospital pharmacy by way of the hospital network, as was described in FIG. 2 of previously incorporated by reference U.S. Pat. No. 7,610,115, entitled "Automated Pharmacy Admixture System (APAS)," and filed by Rob et al. on Dec. 22, 2005. When the hospital pharmacy receives a drug order, the hospital pharmacy enters the drug order into the APAS. The APAS checks to make sure the supplies are in place to fill the drug order in step 2718. If the supplies are available in step 2718, the APAS places the order in its queue in step 2720. The APAS runs and completes the orders in step 2722. The output order, dependent on the drug container, is dropped into the syringe discharge chute 332 or the IV bag discharge chute 344, as described in FIG. 3 of previously incorporated by reference U.S. Pat. No. 7,610,115, entitled "Automated Pharmacy Admixture System (APAS)," and filed by Rob et al. on Dec. 22, 2005. A receptacle placed beneath each chute collects the output container. A pharmacy staff member takes the output away in step 2724 to be used that day, for example, in a hospital ward.

If, when an order is received, the APAS determines, in step 2718, that the supplies needed to fill the order are not in place, the remote user station notifies the operator in step 2726. The operator then proceeds to get stock from inventory in step 2706 and begin reloading the APAS.

The APAS runs in either a batch mode or an on-demand mode dependent on user needs. For example, the APAS runs in the on-demand mode during the day shifts in a hospital, responding to demand from the hospital as it arises. During the hospital evening and night shifts, the APAS runs in the batch mode producing batches of drugs that can be carried in bulk in the hospital pharmacy to maintain inventory.

Table 2 below shows three example queues sorted according to priority and sequence. In this example, the Floor 1 queue has the highest priority, "Stat", and Floor 3 has the lowest priority, "Low". Within each queue, orders are assigned a letter based on the order that they are entered into an APAS, so OrderA is entered first, OrderB second, etc. Each order is given a sequence number as determined by the APAS controller. The orders are sorted within each queue according to sequence number. In this example, if all three queues were executed, OrderA would be executed first, followed by OrderB, OrderC, OrderF, OrderD, etc.

TABLE 2

| Floor 1: Stat | | Floor 2: Medium | | Floor 3: Low | |
| --- | --- | --- | --- | --- | --- |
| Name | Sequence | Name | Sequence | Name | Sequence |
| OrderA | 1 | OrderF | 3 | OrderH | 12 |
| OrderB | 2 | OrderD | 4 | OrderI | 33 |
| OrderC | 3 | OrderE | 7 | OrderJ | 21 |

Sorting of Drug Orders

An example of methods for drug order intake in an APAS are described with reference to FIGS. 42, 43A and 43B of previously incorporated by reference U.S. patent application Ser. No. 11/389,995, entitled "Automated Pharmacy Admixture System," and filed by Eliuk et al. on Mar. 27, 2006.

Figure 28:
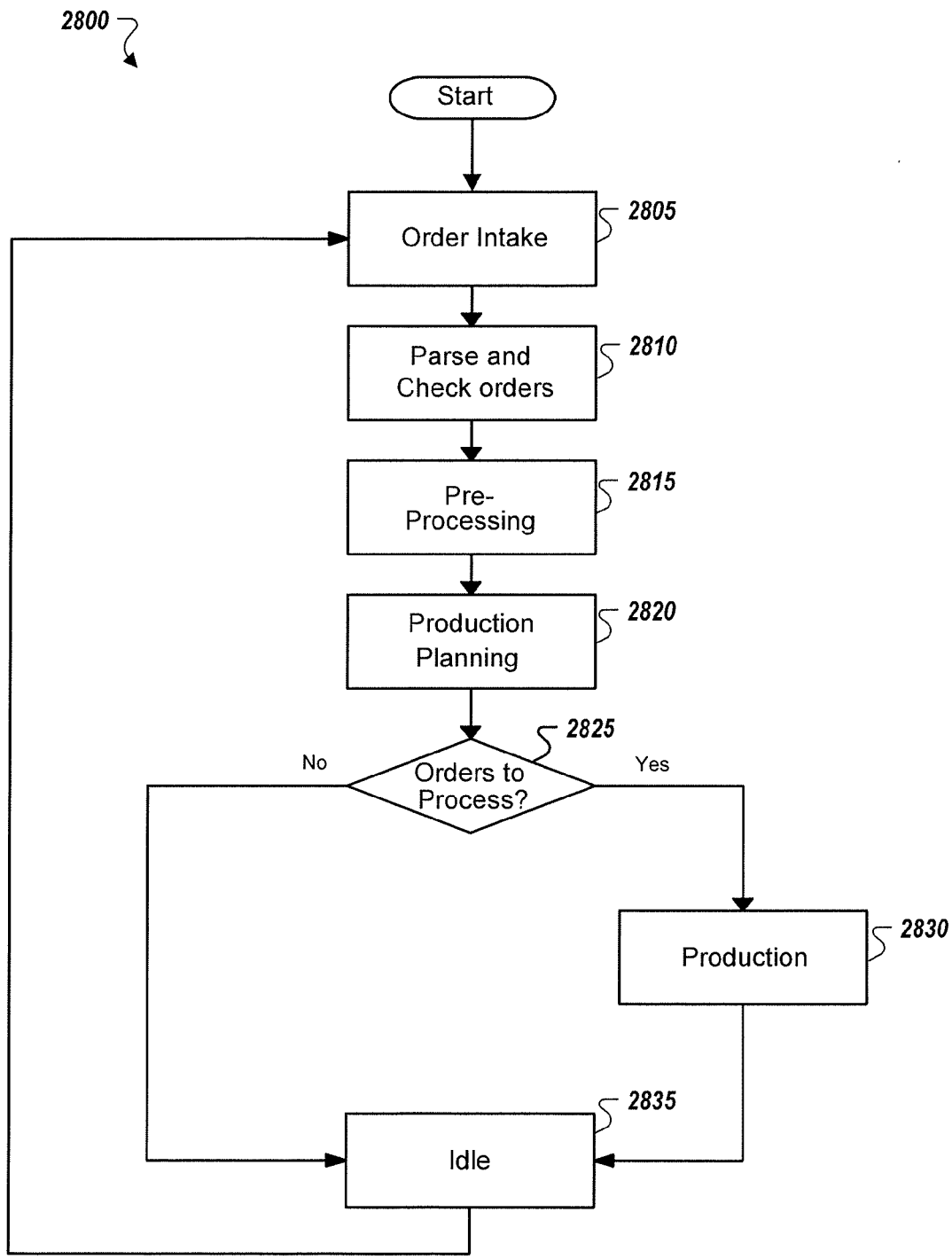
FIG. 28 is a flow chart of an illustrative drug order processing method for an APAS.

FIG. 28 is a flow chart of an illustrative drug order processing method 2800 for an APAS. The method 2800 begins with intake of a drug order by the APAS in step 2805 from a hospital system. Various methods for obtaining drug orders from the hospital system are described with reference to FIGS. 42, 43A and 43B of previously incorporated by reference U.S. patent application Ser. No. 11/389,995, entitled "Automated Pharmacy Admixture System," and filed by Eliuk et al. on Mar. 27, 2006.

After completing the order intake in step 2805, the method 2800 parses and checks received drug orders in step 2810. When individual drug orders are verified, the method 2800 adds the drug orders to a production queue in step 2820. The addition of the drug orders to the production queue are automatic or manual. An APAS includes a plurality of queues. A user enters a series of drug orders as a first queue, via a remote user station. Additionally, a user commands the APAS to poll a FTP server for the drug order files to create a second queue.

The drug orders are organized into queues according to the use of the drug. For example, a queue is created for each prescribing doctor or administering professional, or queues are grouped by floor or medical wing of the patient to receive the drug. An operator controls which queue a drug order is allocated to and may move drug orders between queues. The production queue represents an aggregate of orders to be released to the APAS for production. For example, a first queue contains drugs to be administered to patients on the ground floor of a hospital, and a second queue contains drugs to be administered to patients on the second floor of the hospital. If a patient is moved from the first floor to the second floor, drug orders associated with that patient are moved from the first queue to the second queue.

Each queue is pre-processed to determine the total aggregate of drugs and consumables required to fill the drug orders in the queue. The pre-determined total aggregate of drugs and consumables required to fill the drug orders in the queue becomes the list of inventory items for an operator to load into an APAS.

Whether the drug orders are to be released to the production cell is determined in step 2825. If the drug orders are to be released to the production cell, then the APAS performs the production of the drug order in step 2830. If no drug orders are to be released, then the method 2800 continues to an idle state in step 2835, after which step 2805 is repeated.

The drug orders in each queue are sorted according to a priority and sequence number. The drugs are sorted primarily according to priority number, and sorted according to sequence number within the priority number. In some implementations, priority numbers of 1-4 are used to represent priorities of Low, Medium, High, and Stat. Within each priority number, sequence numbers used are the identification number used by the APAS for the drug in the order, drug concentration, and/or dose quantity. The user edits the priority number of an order. Alternatively, the APAS controls the priority number.

The APAS determines which queue to place a drug order in dependent on the drugs and diluents needed to fill the drug order. For example, the APAS places orders that use the same drug for reconstitution in the same queue. This sorting of orders results in increased performance as the APAS can reuse the same vial for multiple drug orders.

Use of Planning Software and a Phantom Queue

Figure 29:
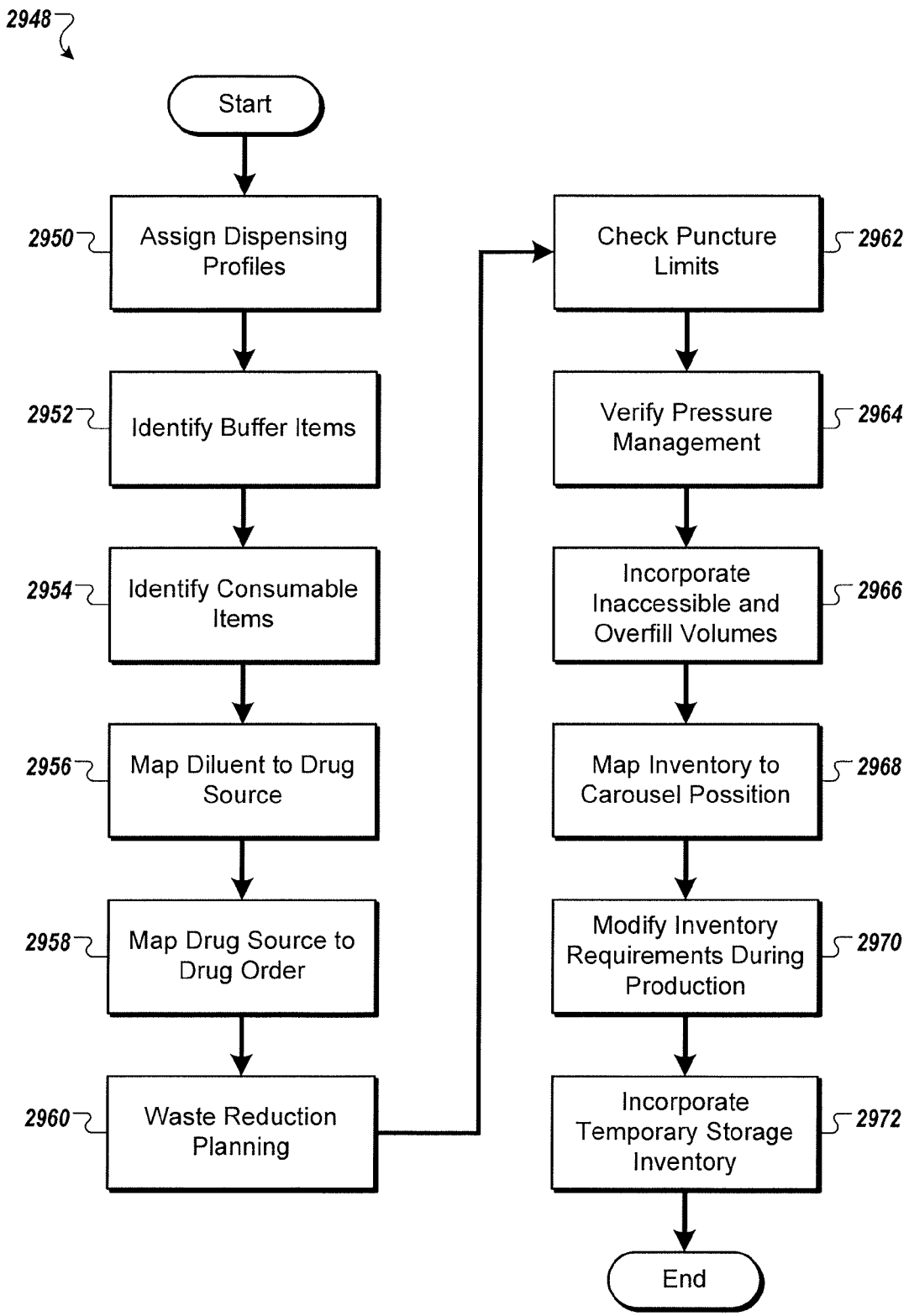
FIG. 29 is an illustrative flow chart showing example operations for preprocessing a queue of drug orders.

FIG. 29 is an illustrative flow chart showing example operations 2948 for preprocessing a queue of drug orders. For example, the process 2948 is performed after a queue of drug orders has been received, and in preparation of procedures to fill the drug orders.

The process 2948 begins with assigning dispensing items based on dispensing profiles in step 2950. Dispensed syringes have dispensing profiles, which specify the dose range (drug volume or quantity) for a particular syringe size, fluid, and concentration. In step 2952, buffer items are identified. An extra syringe of each syringe type assigned in step 2952 are identified. The extra syringe is used, for example, in the case where a syringe is found to be defective or unusable.

Consumable items are identified in the step 2954. Syringes that are used for intermediary transfers are identified. Diluents are mapped to drug sources in step 2956, and drug sources are mapped to drug orders in step 2958. With the steps 2956 and 2958, each drug order has associated with it diluents and drug sources as needed.

Waste reduction planning is processed in step 2960. Techniques that reduce waste or increase efficiency, such as safe reuse or serial use of disposable items, are identified. Puncture limits of vials and bags and other safety measurements are verified in the step 2962. Minimum and maximum values for each item are compared to the associated planned values to ensure that each item is used within the item's appropriate parameters. Pressure management is verified in step 2964. The syringes requested for priming and the order of draws are arranged from the same drug source from largest to smallest volume. In step 2966, inaccessible and overfill volumes are incorporated. Adjustments to the nominal value fluid sources are applied to adjust for overfill or fluid that cannot be reliably accessed.

Inventory is mapped to carousel positions in step 2968. The carousel mapping is used by the APAS during processing to locate inventory and is used by an operator loading the inventory before processing. In step 2970, the APAS monitors inventory usage during processing. Inventory needs can be modified during a failed process or when an anomalous inventory item is discovered. When available, inventory in the temporary storage is utilized in step 2972. For example, if a particular vial is ruined during processing, a duplicate of the vial in temporary storage can be used to continue processing.

Figure 30:
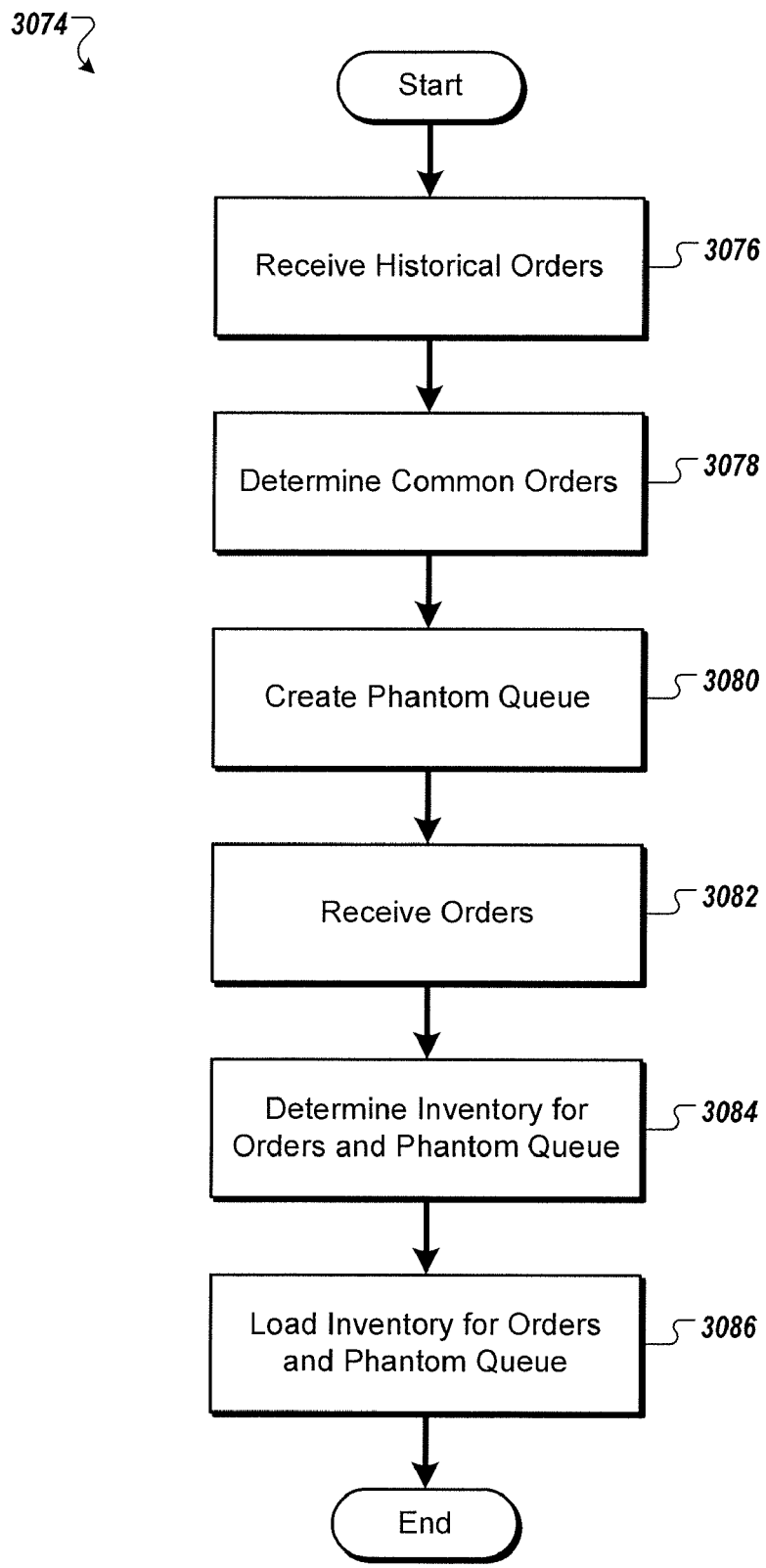
FIG. 30 is an illustrative flow chart showing example operations for inventory management and predictions.

FIG. 30 is an illustrative flow chart showing example operations 3074 for inventory management and predictions. A phantom queue is created to represent expected orders, and the phantom queue is added to one or more real order queues to determine inventory to be loaded into the APAS. The operations 3074 can be performed by a processor that executes instructions stored in a computer-readable medium. For example, a computer device operated by and included in the APAS can perform the operations 3074.

The process 3074 begins with receiving historical orders in step 3076. The APAS controller accesses drug orders that have been processed by the APAS, for example, in the previous month or week. Orders, collections of orders, and/or queues that are regularly processed in the historical orders are identified in step 3078. For example, if a particular drug is ordered every day for the last seven days, that drug order is identified. A phantom queue is created in step 3080. The phantom queue contains the common orders determined in the 3078. Additionally, an operator enters additional orders to the phantom queue, for example, if the operator expects an order in the near future.

In step 3082, orders are received. The received orders are combined, and the inventory required to fill both the received orders and the phantom orders is determined in step 3084. For example, if the phantom queue consists of orders for two intermediary bags and the received orders consist of orders for three intermediary bags of the same drug, inventory requirements are for five bags. The APAS outputs the inventory requirements. An operator loads the inventory for both the received orders and the phantom queue in step 3086. After loading, the APAS processes the received orders that contain the inventory for the phantom queue. Later, for example, if an order comes in that matches the orders of the phantom queue, the later orders are processed without additional loading of the APAS.

In one example, a particular patient staying at a hospital can require the same dose of a particular drug administered every day after dinner. The order for this drug is not received by the APAS until noon, which is later than all other drug orders. In this example, the APAS identifies the regular and late order, and prepares a phantom queue before determining inventory requirements for the day. After processing all morning orders, the APAS is still loaded with the inventory to fill the noon regular and late order.

Error Recovery and Exception Handling

Figure 31:
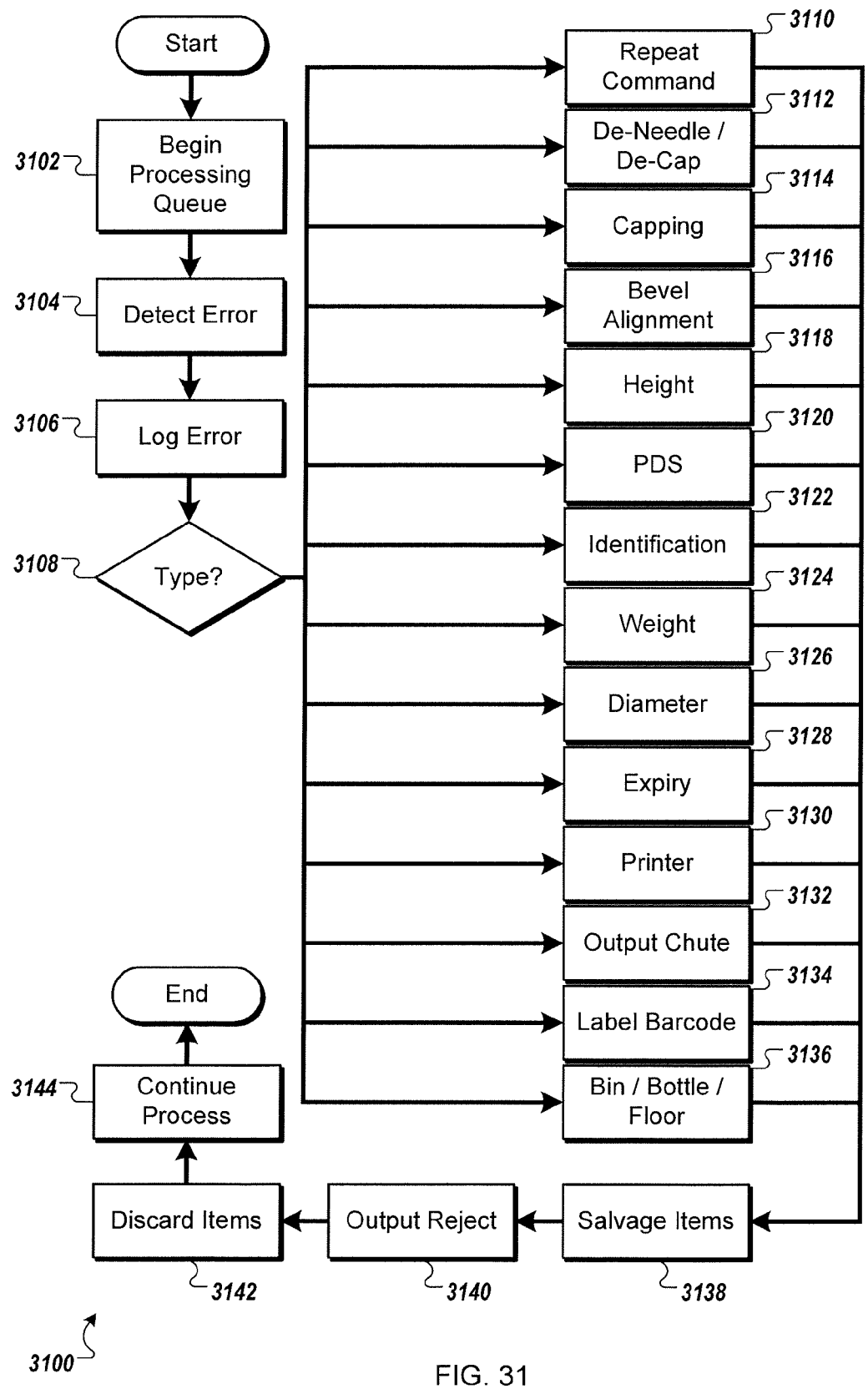
FIG. 31 is an illustrative flow chart showing example operations for detecting and recovering from errors that may occur while processing drug orders.

FIG. 31 is an illustrative flow chart showing example operations 3100 for detecting and recovering from errors that may occur while processing drug orders. The operations 3100 begin with the processing of a queue of drug orders. While processing drug orders, a number of possible errors are detected in step 3104 generating an error event. The errors are logged in step 3106 based on the type of error identified in steps 3110-3136. The log of errors is used, for example, to detect a broken part in the APAS, to schedule maintenance, and/or to determine calibration changes. In step 3110, errors are identified that are corrected by repeating a failed command. The APAS detects a plurality of errors that can include, but is not limited to, the errors identified by the operations 3100.

In step 3112, deneedle and/or decapping errors are identified. A syringe needle cap that is intended to be removed may not be removed, or it may be detected that the syringe did not have a cap, leading to the generation of an error event.

In step 3114, needle capping errors are identified. A camera monitoring a needle cap can provide an image of the needle cap try (e.g., using image processing techniques). The APAS, using the provided image, detects that the intended cap to be used to cap a syringe was not removed from the capping tray. The APAS determines that needle capping did not occur, leading to the generation of an error event.

In step 3116, needle bevel alignment errors are identified. The APAS determines that the needle has an anomalous geometry indicative of the wrong needle type or of particulate contamination of the needle, leading to the generation of an error event. Alternatively, the APAS determines that the syringe is not rotating as intended during the bevel alignment process, leading to the generation of an error event. Alternatively, the APAS determines that the needle is not properly positioned or fully located within a field of view of a camera on a bevel orientation device, leading to the generation of an error event. FIGS. 4A-4C in previously incorporated by reference U.S. patent application Ser. No. 11/937,846, entitled "Control of Fluid Transfer Operations," and filed by Doherty et al. on Nov. 9, 2007 shows an example of a bevel orientation device.

In step 3118, height errors are identified. The APAS determines that the relative height of a vial drug source, an IV bag drug source or diluent source, as held by the robot gripper fingers, is not correct for handoff to the next subsystem, leading to the generation of an error event.

In step 3120, port sanitization system (PSS) errors are identified. Previously incorporated by reference U.S. patent application Ser. No. 12/035,850, entitled "Ultraviolet Sanitization in Pharmacy Environments," and filed by Reinhardt et al. on Feb. 22, 2008 shows an example of a PSS. The APAS determines that a vial to be sanitized is not fully engaged in the PSS interface, and thereby does not draw an adequate vacuum to enable the PSS system, leading to the generation of an error event. Alternatively, the APAS determines that the PSS Ultraviolet (UV) source activation was not operating continuously during the sanitization process, leading to the generation of an error event. Alternatively, the APAS determines that the current flowing to the PSS UV source is outside of nominal limits and is not of the required intensity, leading to the generation of an error event.

In step 3122, identification errors are identified. Identification refers to identification of a source vial or IV bag as being the correct item type. The APAS determines that the source vial or IV bag barcode does not indicate the correct item type, leading to the generation of an error event. Alternatively, the APAS determines that the source item barcode cannot be read, leading to the generation of an error event. Alternatively, the APAS determines that the expected identifying pattern features for the source item cannot be found, leading to the generation of an error event.

In step 3124, weight errors are identified. The APAS determines that the weight of a source vial or IV bag is not within the expected limits for that item, leading to the generation of an error event.

In step 3126, diameter errors are identified. The APAS determines that either the diameter of a source vial or the diameter of an IV bag injection port is outside of the allowed nominal range, leading to the generation of an error event.

In step 3128, expiry errors are identified. The APAS determines that the pharmacy-trained expiry time for a punctured drug vial in the APAS is exceeded, leading to the drug not being used and to the generation of an error event. The expiry time is tracked from the time of first puncture of a bung on a drug vial or IV bag port of a diluent source.

In step 3130, printer errors are identified. The APAS determines that a printed label is not properly dispensed onto a printer platen, leading to the generation of an error event. Alternatively, the APAS determines that a label failed to be picked up by the item for labeling (e.g., a syringe or IV bag) during a labeling operation, leading to the generation of an error event.

In step 3132, output chute errors are identified. The APAS determines that a product has failed to drop out of the output chute and into the output bins, leading to the generation of an error event. The APAS prompts the operator to clear the output chute. Alternatively, the APAS determines that an output chute door (e.g., exterior door 3420, interior door 3415 as shown in FIG. 34) fails to open or close, leading to the generation of an error event.

In step 3134, label barcode errors are identified. The APAS determines that the barcode on an output product cannot be scanned, leading to the generator of an error event.

In step 3136, bin, bottle, and floor errors are identified. The APAS determines that a waste bin sensor indicates "full", leading to the generation of an error condition. Alternatively, the APAS determines that a waste bin sensor indicates that a waste bin is not installed, leading to the generation of an error event. Waste bins are further described with reference to FIG. 33A-33B.

In steps 3138-3142, the process 3100 recovers from errors. Items that have been completed correctly are salvaged in step 3138. Completed drug vials are output, and/or unused syringes are returned to available inventory or temporary inventory stock. Failed, contaminated, corrupt, or otherwise unsalvageable items are output as rejects in step 3140. A vial that has not been processed is output from the APAS as a reject to be disposed of or reclaimed. Active items are discarded in step 3142. For example, an IV bag, which ruptures during processing in the APAS, is disposed of. Additionally, the APAS can re-queue the one or more drug orders that may be affected by the errors.

In one example, an APAS can process drug orders. The APAS attempts to cap a syringe and fails. A capping error is detected and the error is logged in a log file. The syringe is discarded, and the order that required the capped syringe is repeated.

Inaccessible Volume Draw and Actual Volume Calculations

Figure 32:
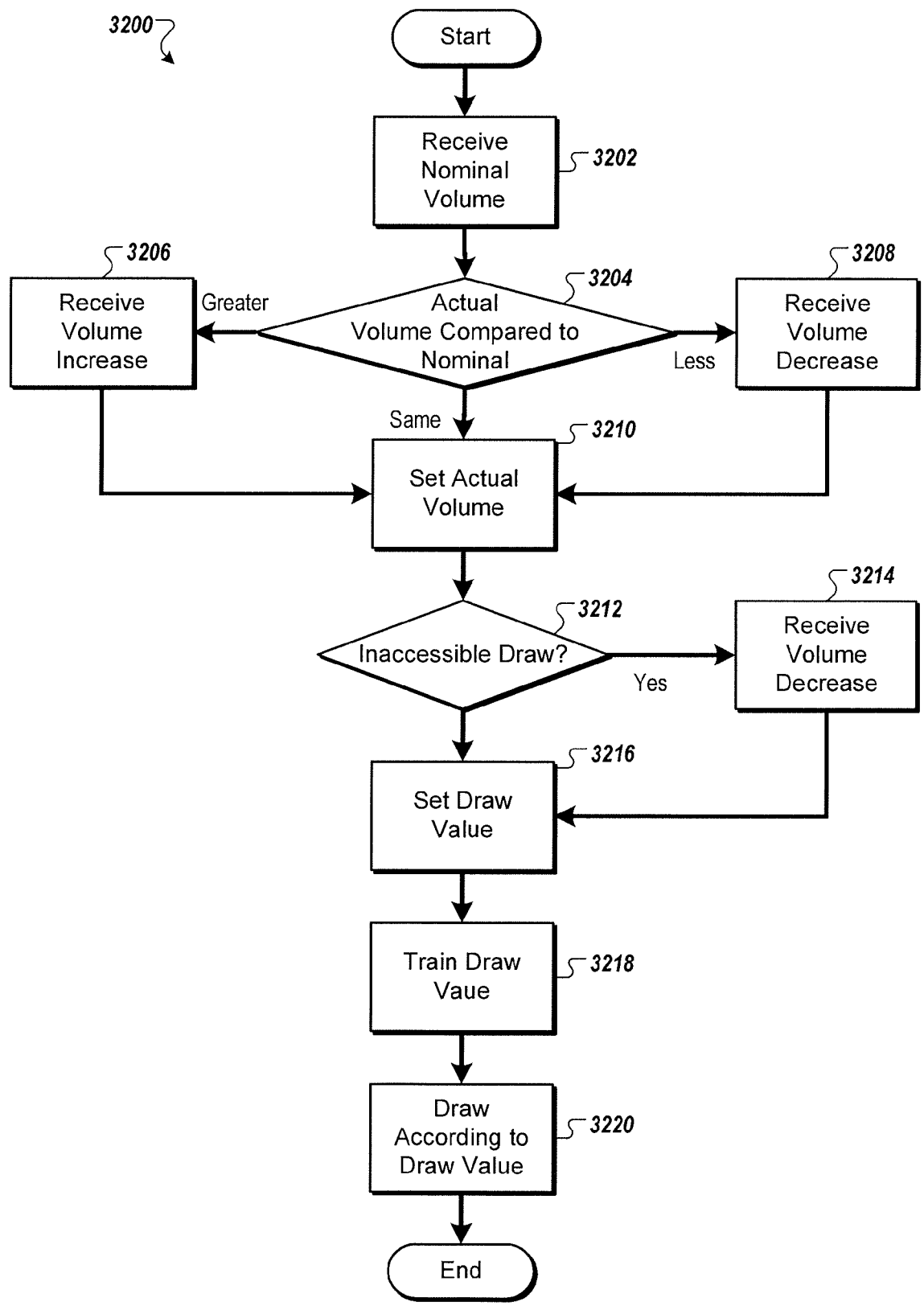
FIG. 32 is an illustrative flow chart showing example operations for drawing a volume of fluid from a fluid source, such as a reconstituted or non-reconstituted drug vial, diluent bag, and/or an intermediary bag.

FIG. 32 is an illustrative flow chart showing example operations 3200 for drawing a volume of fluid from a fluid source, such as a reconstituted or non-reconstituted drug vial, diluent bag, and/or an intermediary bag. In some implementations, fluid sources handled by the APAS have a nominal volume measurement assigned. The nominal volume measurement is a large round number, such as 100 milliliters (mL). However, the actual volume of fluid is, in some cases, greater than or lesser than the nominal value, such as 103 mL or 97 mL of fluid in a nominal 100 mL vial.

For some fluid sources, attempts by the APAS to draw the entire nominal or actual volume of fluid results in inconsistent draws. For example, in some fluid bags, creases form and entrapped air is drawn. In another example, for some vials, fluid wicks to the upper lip of a vial bung. Some techniques, such as slurping while withdrawing the needle from a vial, help to eliminate some of the inconsistencies. Adjusting the draw value of each fluid source allows for an increase in the available volume for some containers, and for reliable draws from some containers.

The process 3200 executes to adjust the draw associated with each fluid source. A nominal volume for a fluid source is entered into the APAS in step 3202. When a drug vial is used for the first time, or when an intermediary bag is planned, a nominal volume can be given. The actual volume of the fluid source is compared to the nominal volume in step 3204. Some fluid sources have an actual value published by the manufacturer to ensure that, at a minimum, the nominal volume is met in every order. Alternatively, an APAS operator may discover that a fluid source runs out before the entire nominal volume is drawn and the operator may estimate or calculate the actual volume. If the actual volume is greater than the nominal volume, a volume increase is received in step 3206. Similarly, if the actual volume is less than the nominal volume, a volume decrease is received in step 3208. The actual volume of the fluid source is set in the APAS in step 3210 by adding the volume increase or subtracting the volume decrease from the nominal value. This actual value is stored and associated with every fluid source of the same type processed by the APAS.

Through trial and error, experience with similar fluid sources, or based on the design of the fluid source, the APAS operator determines in step 3212 that some of the fluid in the fluid source cannot be drawn reliably. The APAS operator enters an inaccessible volume decrease in step 3214. The inaccessible volume decrease is subtracted, by the APAS controller, from the actual volume in the fluid source to determine a draw value in step 3216. The draw value is the maximum volume that the APAS will draw from the fluid source under normal operations. For example, the draw value is the volume of liquid that can be reliably drawn from the fluid source.

The APAS trains the draw value for the fluid source in step 3218. When processing the fluid source after training, the APAS draws up to the draw value of fluid from the fluid source in step 3220.

For example, a reconstituted vial is given a nominal volume of 100 mL. It is found that, when properly reconstituted, the vial contains 103 mL of fluid. Furthermore, it is found that 101 mL of the 103 mL can be reliably drawn by the APAS. In this case, a nominal volume adjustment of +one mL is trained into the APAS, for a final available volume of 101 mL.

In another example, it is found that a vial of non-reconstituted drug has a nominal volume of 100 mL and an actual volume of 101 mL. It is determined that 98 mL is considered accessible by the APAS. In this case, a total volume adjustment of −two mL can be trained for that vial.

Multiple Separate Waste Bins

An example of a waste bin area included in an APAS is described with reference to FIGS. 39A and 39B of previously incorporated by reference U.S. patent application Ser. No. 11/389,995, entitled "Automated Pharmacy Admixture System," and filed by Eliuk et al. on Mar. 27, 2006.

Figure 33A:
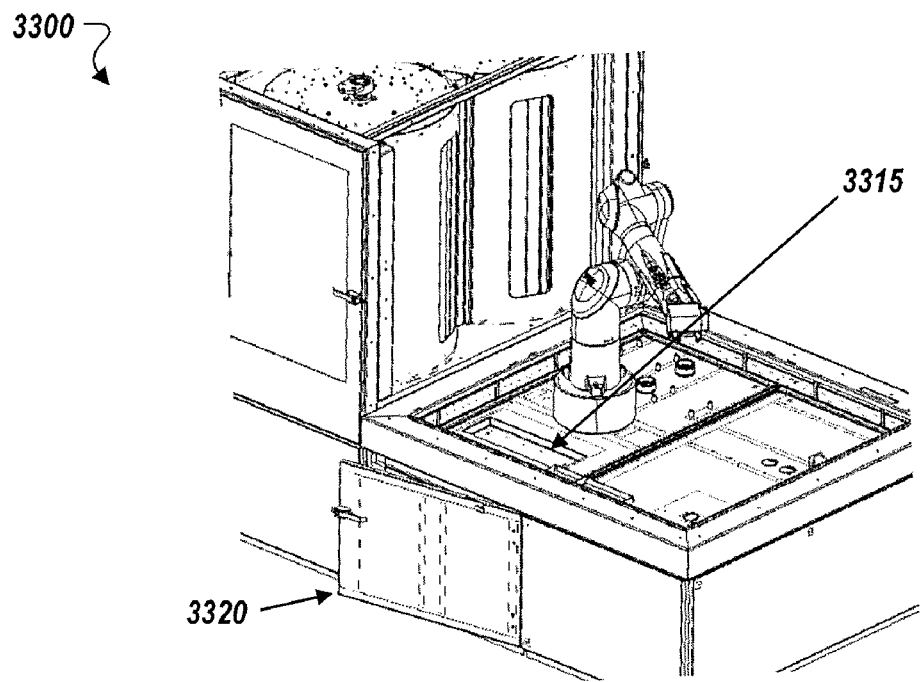
FIGS. 33A and 33B show an illustrative waste bin area of an APAS.
Figure 33B:
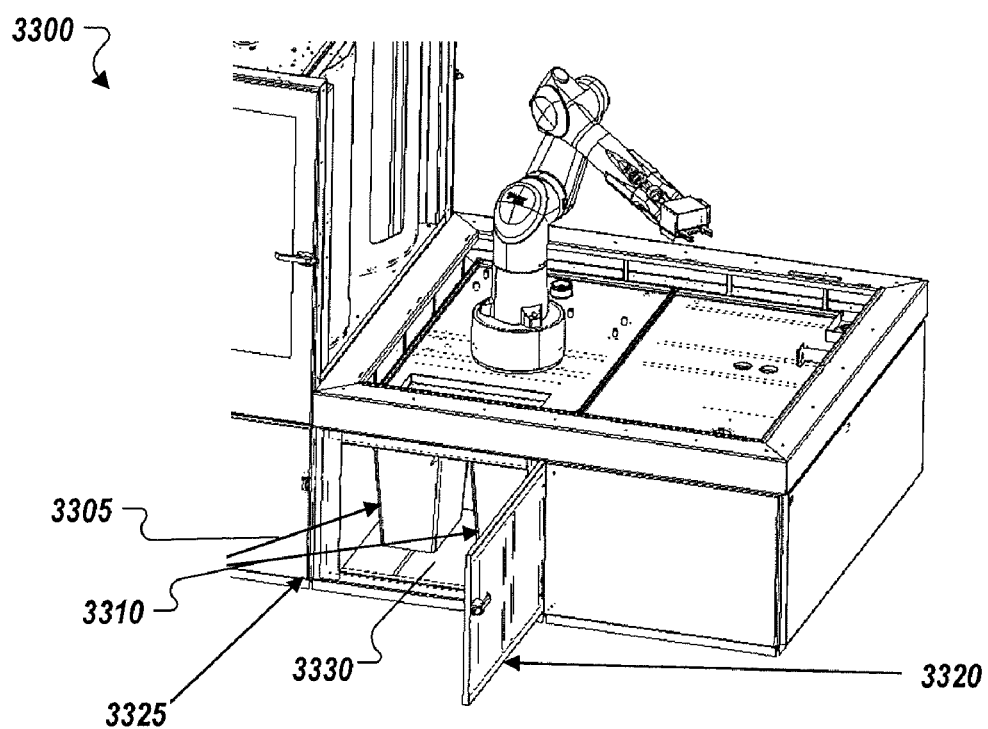
Figure 34A:
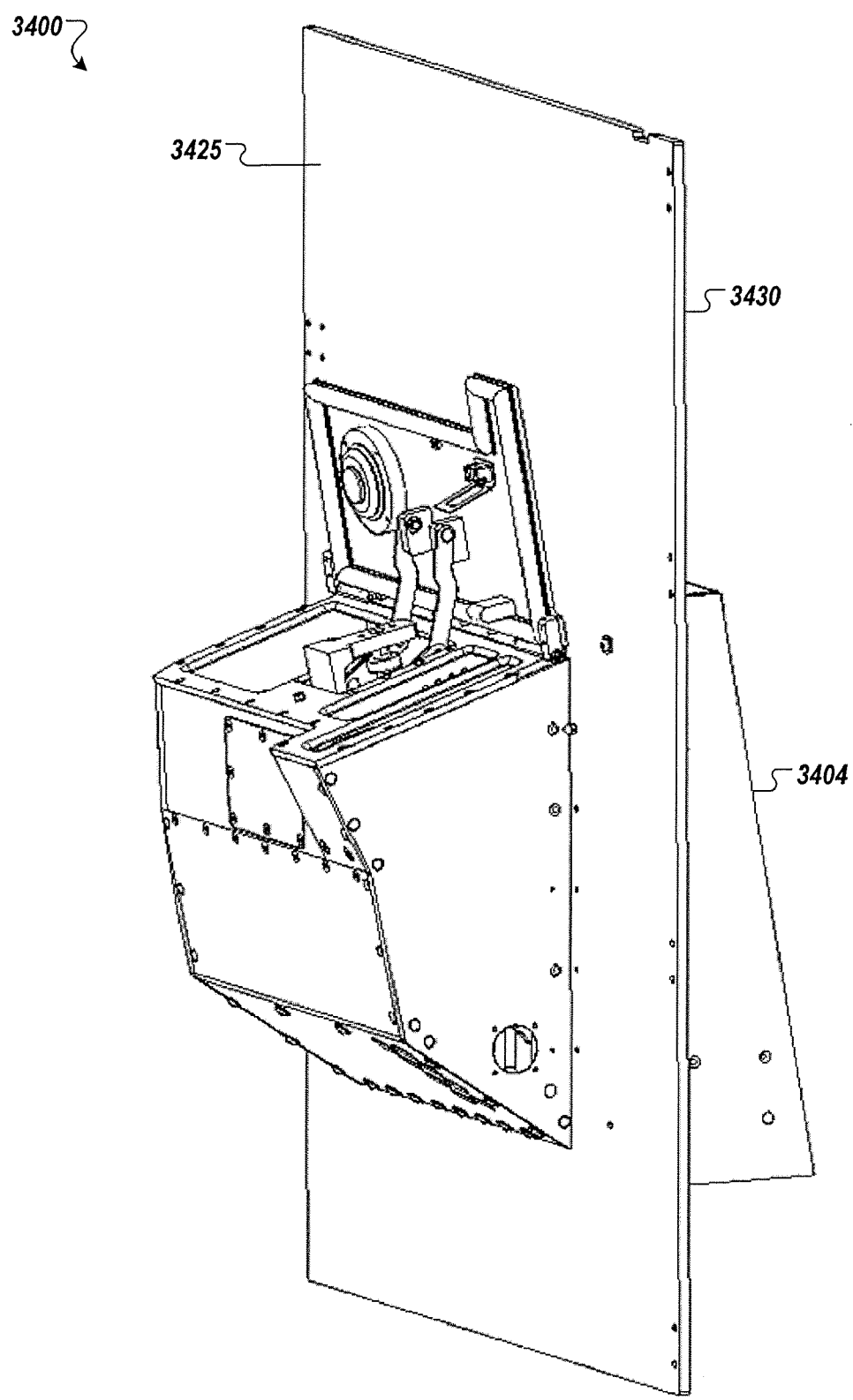
FIGS. 34A-34E show example views of a product output chute in an APAS.
Figure 34B:
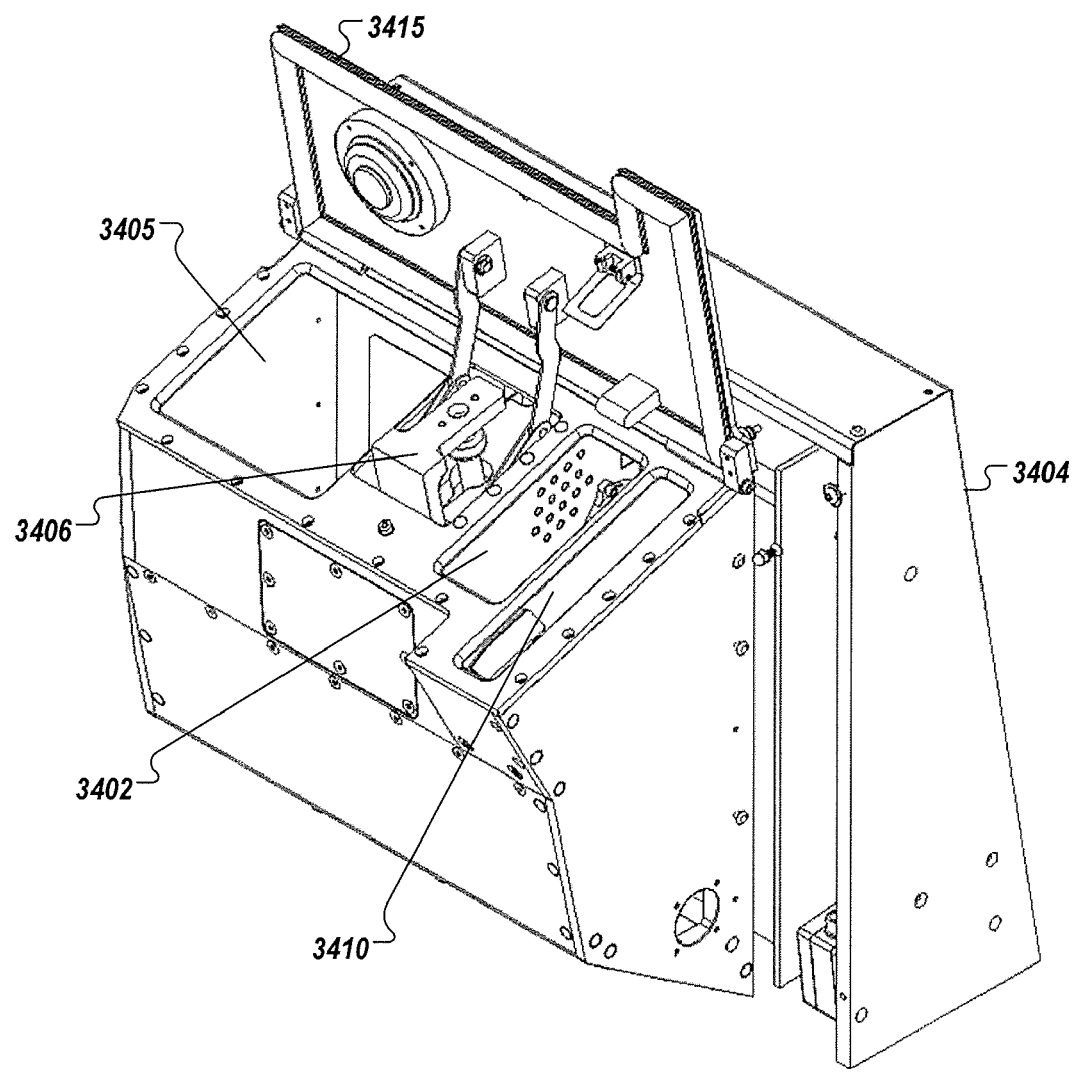
Figure 34C:
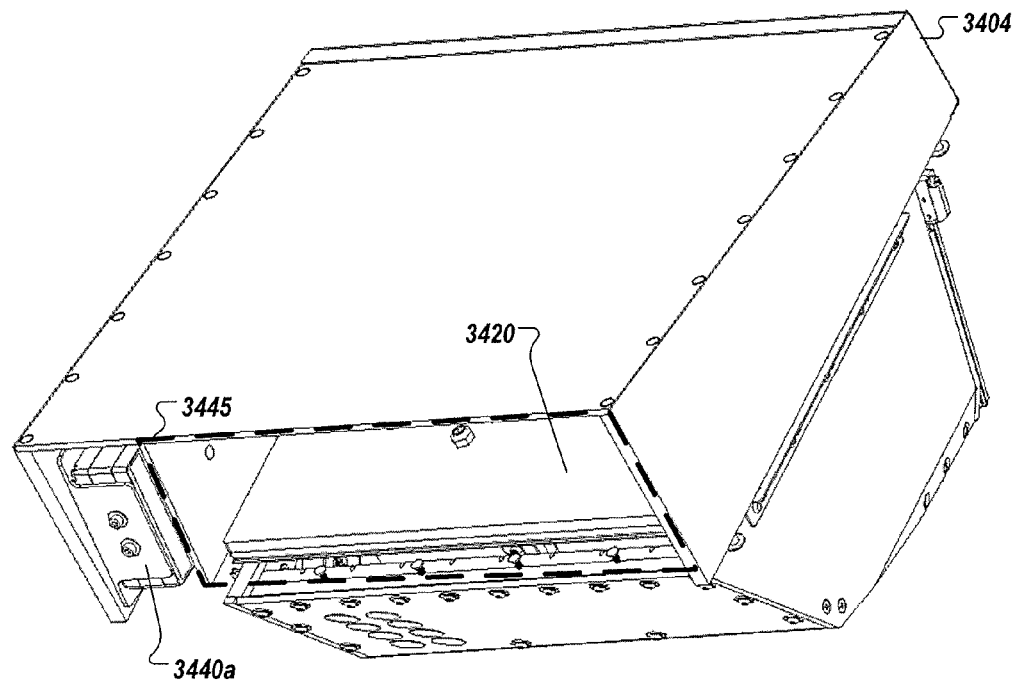
Figure 34D:
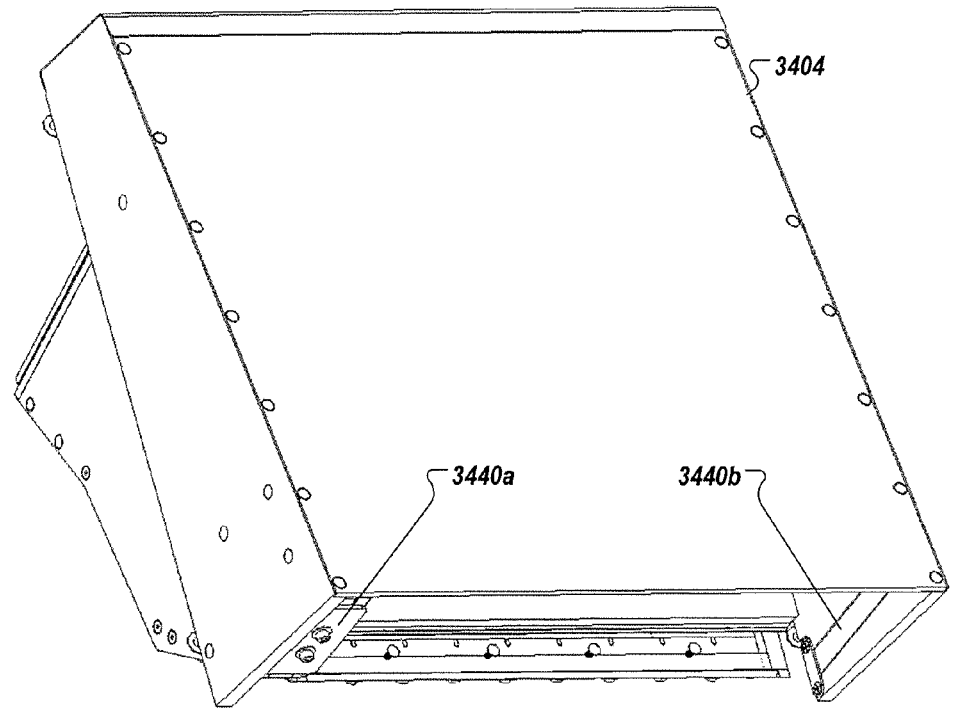
Figure 34E:
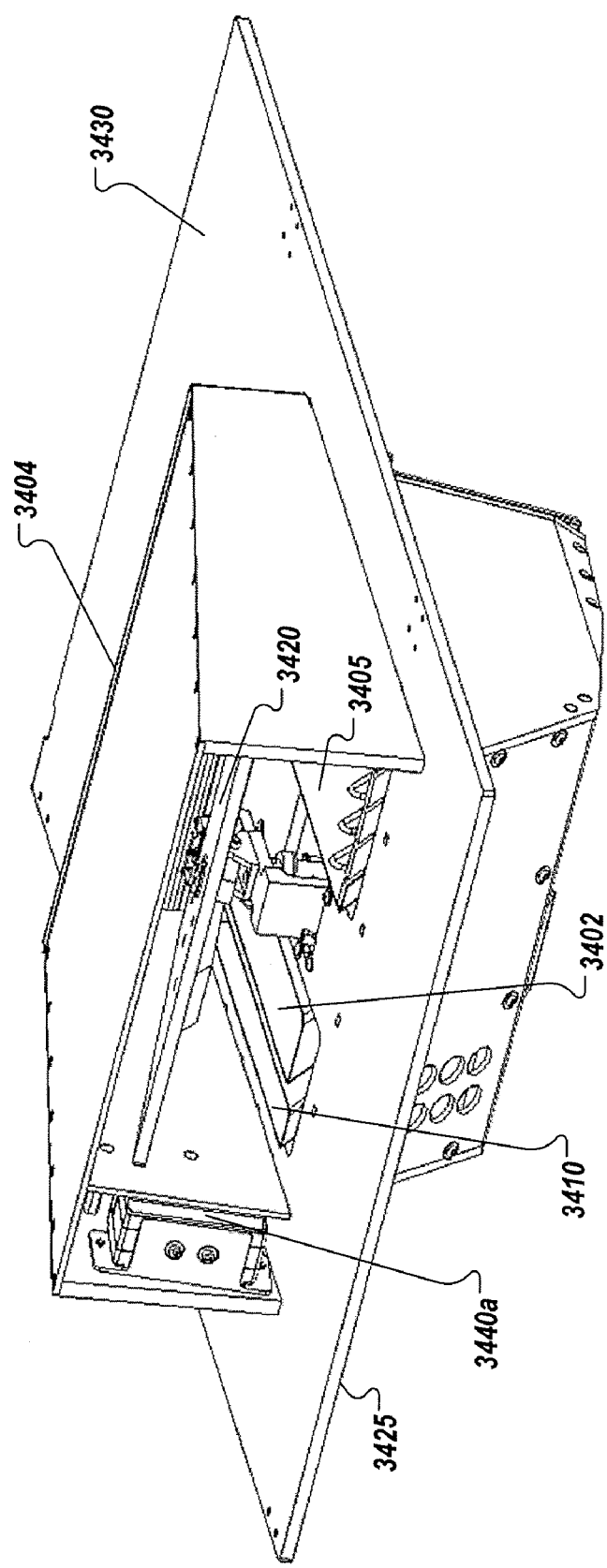

FIGS. 33A and 33B show an illustrative waste bin area 3300 of an APAS. The waste bin area includes one or more waste bins (e.g., waste bins 3305 and 3310), an interior door 3315, an exterior door 3320 and a waste bin area enclosure liner 3325. The waste bin area 3300 is coupled to the compounding area 3305 via a pass-through so that the waste bins 3305, 3310 can be emptied without interrupting cell processing.

The waste bin area 3300 includes a stainless enclosure 3330 that is sealed from the ambient environment. The stainless enclosure includes an enclosure liner 3325. The waste bin area 3300 is fitted with the interior door 3315 that, when closed, isolates the waste bin area 3300 from the compounding area 3305. The waste bin area 3300 is also fitted with the external door 3320. For example, an operator accesses the waste bin area 3300 from the exterior for removal of the waste bins 3305, 3310.

The interior door 3315 and the exterior door 3320 are interlocked so that as the exterior door 3320 is opened a few degrees, the interior door 3315 closes completely. As described with reference to FIGS. 31A and 31B of previously incorporated by reference U.S. patent application Ser. No. 11/389,995, entitled "Automated Pharmacy Admixture System," and filed by Eliuk et al. on Mar. 27, 2006, a waste bin has a connection to the peripheral duct 3150 around the base of the APAS that causes air to be pulled from the APAS into the waste bin area as long as the internal door 3315 is open, and draws air from the exterior when the internal door 3315 is closed and the external door 3320 is open. For example, this may substantially prevent aerosolized drug from the waste bin area 3300 from returning to the APAS area or escaping from the APAS. The APAS performs the interlocking function with the use of a mechanical linkage. Alternatively, the APAS performs the interlocking function with the use of an electromechanical actuator on the internal door 3315, that includes sensing or operator switches on the external door 3320 to initiate the actuator.

The APAS confirms the presence of waste bins 3305, 3310. The APAS includes sensors located in the enclosure 3330 that detect the presence of waste bins 3305, 3310. The remote user station warns an operator if one or more of the waste bins 3305, 3310 are missing prior to the start of a compounding operation.

Waste bins 3305, 3310 each include a waste-level sensor. The waste-level sensor detects the level of waste in the waste bin (e.g., waste bins 3305, 3310). The remote user station warns an operator when the waste level in the bin is approaching the full level. The operator halts the operation of the APAS during a compounding operation, at a convenient time, to empty the waste bin. Additionally, the waste-level sensor causes the APAS to halt a compounding operation if the waste bin has reached the full level and the waste bin needs immediate emptying.

The waste bins 3305, 3310 are a combination of standard medical waste disposal containers. The waste bins 3305, 3310 are standard sharps containers. Alternatively, the waste bins 3305, 3310 are medical waste disposal containers specifically designed for the disposal of cytotoxic waste.

Solid waste includes, but is not limited to: empty, partially used or time expired diluent bags; empty, partially used or time expired vials; used syringes with and without attached needles; failed dose syringes that include attached, uncapped needles where the APAS was unable to remove the needle, cap the needle, or label the syringe for later reclamation by an operator by way of a reject rack; and syringe cap trays which may be empty or which may include unused syringe caps.

Additionally, the APAS includes a waste container inside the compounding area for the disposal of needle caps and needles removed from syringes during compounding. An example of the waste container is waste receptacle 2335 as shown in FIG. 23 of previously incorporated by reference U.S. patent application Ser. No. 11/389,995, entitled "Automated Pharmacy Admixture System," and filed by Eliuk et al. on Mar. 27, 2006.

An operator removes the waste bins 3305, 3310 from the APAS in order to empty the waste bins. The operator empties the contents of each of the waste bins into one or more larger waste containers that accept the waste included in the bin. The larger waste containers are located outside of the APAS. The operator reloads the waste bins 3305, 3310 into the APAS for subsequent reuse.

In some implementations, a waste bin (e.g., waste bins 3305, 3310) is designed to accept a sealing lid. An operator can store the sealing lid inside the waste bin area 3300. The operator has immediate access to the lid in order to apply the lid to the waste bin before removal of the waste bin from the waste bin area. The operator can empty the contents of the close-lidded waste bin into a larger waste container outside of the APAS. Once emptied, the operator removes the lid from the waste bin and places both the lid and the waste bin back into the waste bin area 100 for subsequent reuse. The close-lidded waste bin remains outside of the APAS for later disposal. The operator loads the waste container area 3300 with a different lid and waste bin.

In some implementations, the waste bin area 3300 includes waste bins 3305, 3310 for solid waste and an additional fluid waste bin (container) for liquid waste disposal from the APAS. FIG. 7 shows waste bins 702, 704 and liquid waste container 700. As described with reference to FIGS. 6 and FIG. 7, the APAS uses an extraction syringe and needle (e.g., syringe 604 and needle 606) to dispense discarded liquid into a liquid waste drain tube (e.g., liquid waste drain tube 602) located on the syringe manipulator device (e.g., syringe manipulator device 600). The liquid waste drain tube 602 drains the discarded fluid into the liquid waste container 700 located in the waste bin area of the APAS. A user may regularly empty the liquid waste container 700 during APAS idle times.

During a compounding operation, the APAS discards fluid drawn into a syringe from a container. The APAS discards fluid drawn into a syringe during IV bag priming where an indeterminate amount of fluid is drawn into the syringe. The APAS discards fluid from a syringe while equalizing pressure in a container. The APAS discards fluid drawn into a syringe where the fluid draw adjusted the amount of diluent in the preparation of a final volume for an IV bag.

Referring to FIG. 4 and paragraph [0083] of the previously incorporated by reference U.S. patent application Ser. No. 12/271,828, entitled "Method And Apparatus For Automated Fluid Transfer Operations," and filed by Eliuk et al. on Nov. 14, 2008, a syringe expels fluid previously drawn into a syringe into a drip catcher. A syringe manipulator device includes a drip catcher. A syringe manipulator device in an APAS is described with reference to FIG. 7 of previously incorporated by reference U.S. patent application Ser. No. 11/937,846, entitled "Control of Fluid Transfer Operations," and filed by Doherty et al. on Nov. 9, 2007.

The fluid waste bin accepts fluid waste from the drip catcher included in the syringe manipulation device. The APAS uses gravity to assist drip catching from the drip catcher and into the fluid waste bin. For example, a fluid waste bin having suction derived from an exhaust fan in the APAS compounding cell assists the gravity fed drip catching.

The APAS interacts with and monitors the fluid waste bin in a similar manner as a solid waste bin. The APAS confirms the presence of the fluid waste bin. The fluid waste bin includes a waste-level sensor. The fluid waste bin is designed to accept a sealing lid.

In some implementations, the APAS includes two or more solid waste bins in order to segregate solid waste along with a liquid waste bin. The APAS includes a first waste bin for glass containers (e.g., vials), a second waste bin for plastic waste (e.g., IV bags) and a third waste bin for sharps (e.g., syringes with needles attached). Additionally, the APAS includes a fourth waste container for liquids. Segregating solid waste may reduce the risk of breakage of glass containers. Segregating solid waste separates containers that may contain drug residue (e.g., glass vials that contain a medicament) separately from containers that may contain little or no drug residue (e.g., plastic IV bags that contain a diluent). Segregating the sharps from the remaining solid waste reduces if not eliminates the possibility of operator injury when disposing of syringes with needles.

Monitoring of Output Chutes

An example of output chutes included in an APAS is described with reference to FIGS. 35A-35C and FIGS. 36A-36B of previously incorporated by reference U.S. patent application Ser. No. 11/389,995, entitled "Automated Pharmacy Admixture System," and filed by Eliuk et al. on Mar. 27, 2006.

FIGS. 34A-34E show example views of a product output chute 3400 in an APAS. A robot places products leaving the APAS in the product output chute 3400. The product output chute 3400 includes one or more product passages (e.g., chutes 3405, 3410, 3402), an interior door 3415, an exterior door 3420, an interior face 3425 and an exterior face 3430. The product output chutes 3405, enable the segregation of products (e.g., syringes, IV bags, etc.) leaving the APAS. The chutes 3405, 3410, 3402 include vertical product passages where one or more motor-actuated doors close off the ends of the vertical product passages. The interior door 3415 covers both product passages. The exterior door 3420 closes off both product passages.

Figures 35A, 35B:
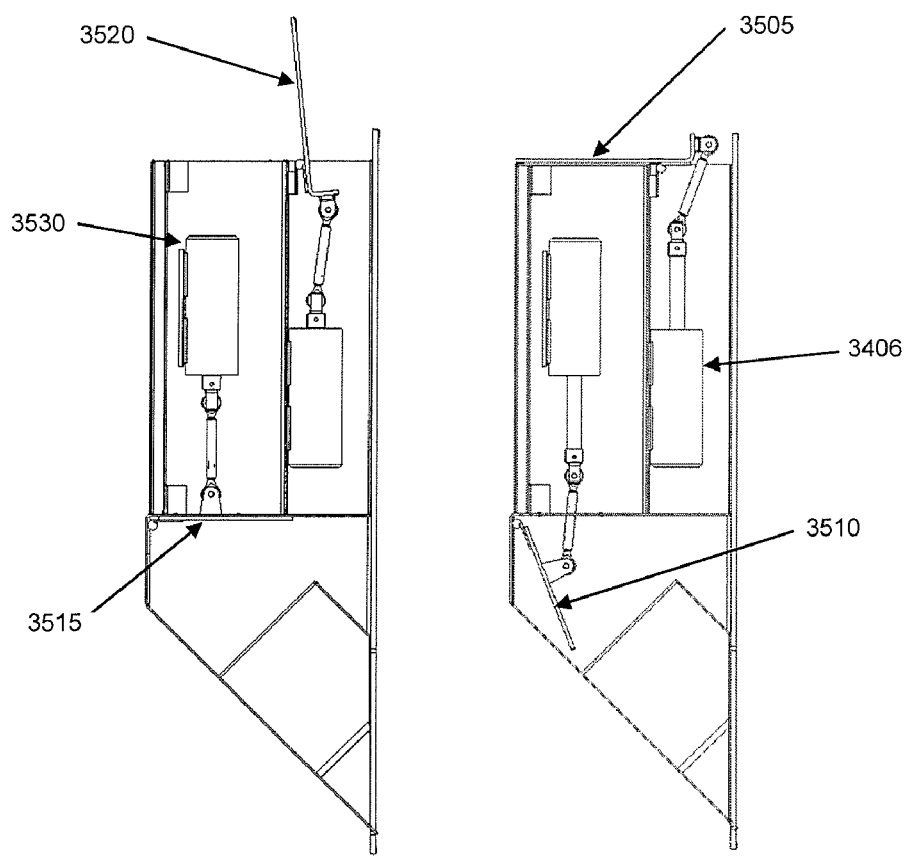
FIGS. 35A-35B show example views of a product output chute in the course of releasing a product from an APAS.

FIGS. 35A-35B show example views of a product output chute 3400 in the course of releasing a product from an APAS. An interior door (e.g., interior door 3415) on the product output chute is normally closed (e.g., closed interior door 3505) while an exterior door (e.g., exterior door 3420) is normally open (e.g., open exterior door 3510). When a product is ready for release from the APAS, the exterior door closes (e.g., closed exterior door 3515), the interior door opens (e.g., opened interior door 3520) and the robot places the product through the opened interior door 3520 into one of the vertical product passages or chutes (e.g., chutes 3405, 3410, 3402). The robot then releases the product. The product drops into the selected product chute. The dropped product comes to rest on the closed exterior door 3515. The opened interior door 3520 closes (e.g., closed interior door 3505). Sometime later (e.g., one or more seconds), the exterior door opens (e.g., opened exterior door 3510) and gravity assists the product in exiting the product output chute 3400. Additionally, one or more actuators located in the product passages can dislodge products that may adhere to the product passage walls. The exterior door 3515 then closes when the APAS detects that the product has dropped from the output chute. The air in the output chute is purged to be clean when the interior door 3520 opens.

Referring to both FIGS. 34A-34E and FIGS. 35A-35B, actuator 3406 controls the opening and closing of the interior door 3415. Actuator 3530 controls the opening and closing of the exterior door 3420. Each vertical product passage or chute has a separately controllable interior door, exterior door, or both. The output chute doors (interior door 3415, exterior door 3420) are operated by actuators that include, but are not limited to, solenoids, stepper motors, servo motors, pneumatics, ball screws, belt drives and force multiplying mechanical linkages. The output chute doors (interior door 3415, exterior door 3420) include sensors to indicate the position of the output chute doors. Each door includes one or more sensors to indicate the position of the door (e.g., opened or closed).

A sensor for an output chute door supplies a digital signal to the APAS controller that indicates if the output chute door is open or closed. The digital signal provided by the sensor is equal to a logical "1" (or is at a high level) when the output chute door is open. The digital signal provided by the sensor is equal to a logical "0" (or is at a low level) when the output chute door is closed.

A sensor for an output chute door supplies an analog signal to the APAS controller that indicates if the output chute door is open, closed or in a position somewhere in-between open and closed. The analog signal provided by the sensor is equal to a maximum signal output level (e.g., a high level) when the output chute door is fully open. The analog signal provided by the sensor is equal to a minimum signal output level (e.g., a low level) when the output chute door is fully closed. Using feedback, the analog signal provided by the sensor is at signal levels between the maximum and minimum levels dependent on the position of the output chute door between fully open and fully closed, respectively.

Referring to FIGS. 34A-34E, a bottom passage (bottom chute opening 3445) of the product passages (chutes 3405, 3410, 3402) includes a monitoring device 3440a, 3440b mounted inside of a protective shroud 3404 on the exterior of the APAS. The monitoring device 3440a, 3440b monitors the successful exit of products from the APAS. Signals generated by the monitoring device 3440a, 3440b indicate the passage of the product out of the bottom chute opening 3445.

In some implementations, the monitoring device 3440a, 3440b is a high-density light curtain. As a product exits the APAS through bottom chute opening 3445, the product passes through the high-density light curtain. The signals generated by the high-density light curtain follow the passage of the product through the bottom chute opening 3445 and out of the APAS. A light curtain includes a transmitter and a receiver (monitoring device 3440a and monitoring device 3440b, respectively). The transmitter of a high-density light curtain projects a high-density array of parallel infrared light beams to the receiver. The receiver of a high-density light curtain includes of large number of photoelectric cells. As a product passes through the bottom chute opening 3445, the product breaks one or more of the beams between the transmitter and the receiver. Therefore, the monitoring device 3440a, 3440b monitors the passing of a product through the bottom chute opening 3445 and out of the APAS. If a product does not pass through the bottom chute opening 3445 (it is stuck), one or more of the beams between the transmitter and the receiver is broken, indicating the presence of the product passing through the bottom chute opening 3445.

Figure 36:
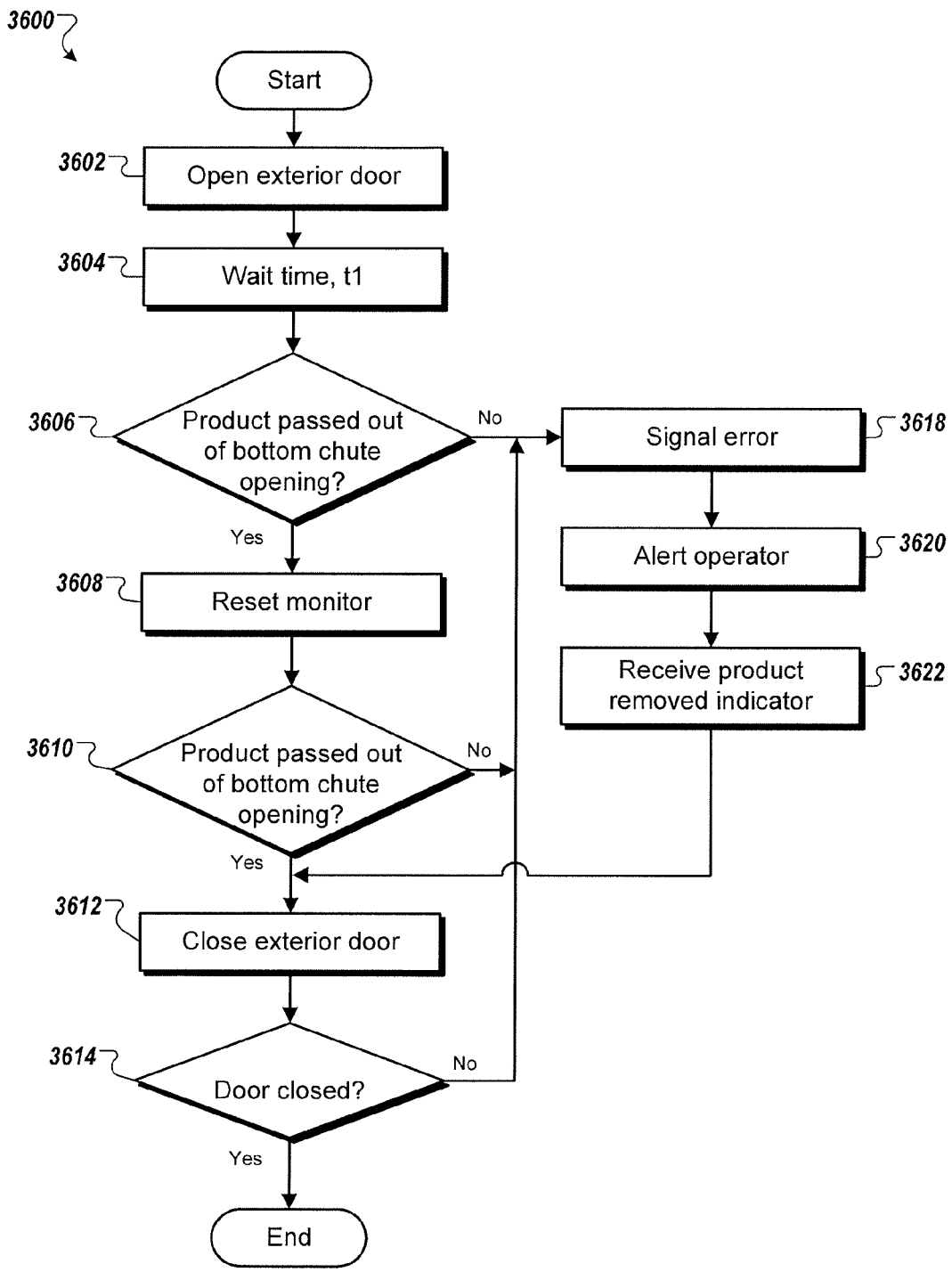
FIG. 36 is an illustrative flow chart showing example operations for detecting the presence of a product in a product output chute.

FIG. 36 is an illustrative flow chart showing example operations 3600 for detecting the presence of a product in a product output chute (e.g., product output chute 3400). The operations 3600 can be performed by a processor that executes instructions stored in a computer-readable medium. For example, a computer device operated by and included in the APAS can perform the operations 3600.

The operations 3600 are described with reference to FIGS. 34A-34E. The operations 3600 begin when the robotic arm is releasing the product. In step 3602, the APAS opens the exterior door 3420. The APAS waits a first predetermined time (e.g., time t1) in step 3604. The predetermined time (e.g., time t1) is determined based on an average time for a product to exit the APAS through the bottom chute opening 3445. In step 3606, the APAS controller determines if the product passed through the bottom chute opening 3445 by checking the monitoring device 3440a, 3440b. The monitoring device 3440a, 3440b indicates the presence of the product during passage through the bottom chute opening 3445. The monitoring device 3440a, 3440b indicates the product has cleared the bottom chute opening 3445 when the APAS controller attempts to reset the monitoring device in step 3608. In step 3610, the APAS controller checks the monitoring device 3440a, 3440b to see if the product remains in the bottom chute opening 3445. If the monitoring device 3440a, 3440b continues to detect the presence of the product in the bottom chute opening 3445, the remote user station alerts an operator of the obstruction in step 3620. The remote user station instructs the operator to clear manually the bottom chute opening 3445 before closing the exterior door 3420 (e.g., remove the product by hand from the bottom chute opening 3445). Once the operator removes the product, the operator indicates to the remote user station that they have removed the product in step 3622, clearing the obstruction.

Additionally, in step 3610, if the monitoring device 3440a, 3440b does detect a product in the field of view of the monitoring device 3440A, 3440b, then the APAS controller closes the exterior door 3420 of the product output chute 3400, in step 3612.

Once the APAS controller closes the exterior door 3420 in step 3612, the APAS controller checks one or more output chute door sensors, as described above, for the exterior door 3420 to verify that the exterior door 3420 is fully closed and sealed. If the output chute door sensors for the exterior door 3420 indicate that either door is not fully closed and sealed, the remote user station alerts an operator to the error in step 3618. The operator is instructed to clear the blockage (e.g., the stuck product) and provide an indication to the remote user station that the blockage has been cleared (e.g., the product has been removed) which is received by the APAS in step 3622. The APAS controller then instructs the exterior door 3420 to close.

If the output chute door sensors for the exterior door 3420 indicate that the exterior door is fully closed and sealed, the operations 3600 end. The remote user station indicates to an operator the successful exiting of the product from the APAS. The APAS will then be ready to release the next product.

In some implementations, the monitoring device 3440a, 3440b is high-density light curtain that includes a feature to self calibrate and self check its own functionality. If the light curtain self check discovers an internal problem with the light curtain, an alarm flag is raised and the APAS control software using the remote user station alerts the operator of the problem.

Cross Contamination Management

During a reconstitution process, the robotic arm transfers a syringe between stations using one or more gripper devices. The gripper devices include gripper fingers used to grasp and hold the syringe while transferring it between stations. The gripper fingers hold the syringe while the APAS performs a particular operation. Examples of gripper devices and gripper fingers are described in previously incorporated by reference U.S. patent application Ser. No. 12/209,097, entitled "Gripper Device," and filed by Eliuk et al. on Sep. 11, 2008.

Figure 46:
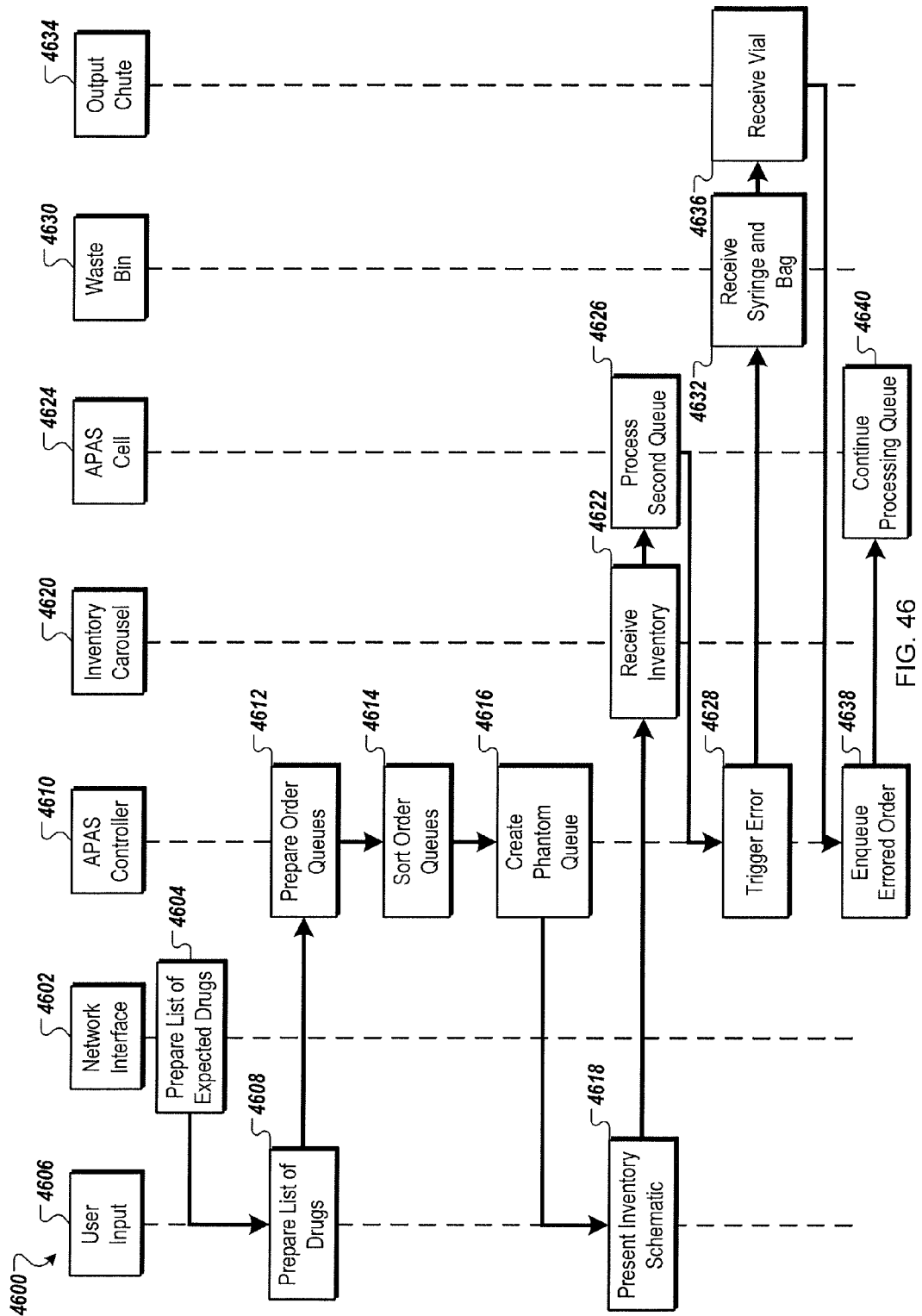
FIG. 46 is an example swimlane diagram showing a system for using an APAS.

Because a syringe may contain fluid, there is the possibility of small drips on the end of a needle prior to deneedling (removal of the needle from the syringe) or on a luer lock hub on the syringe after deneedling due to the squeeze of gripper fingers on the barrel of the syringe. FIG. 46 of previously incorporated by reference U.S. patent application Ser. No. 11/389,995, entitled "Automated Pharmacy Admixture System," and filed by Eliuk et al. on Mar. 27, 2006 shows an example of a syringe for use in an APAS. The robotic arm is programmed to identify and/or follow a motion trajectory when carrying a syringe from station to station to minimize the opportunity for cross contamination. The path in the APAS to a syringe capping station from a needle removal station is arranged so as not to pass over any other equipment to substantially minimize the chance that any drops might fall on other surfaces (e.g., unused syringe caps, other medical containers, surfaces that contact medical containers). Any drips from the syringe are arranged to drop onto a drip pan that can be cleaned. Additionally, disposable drip mats may cover the drip pan. FIG. 24 in previously incorporated by reference U.S. patent application Ser. No. 11/389,995, entitled "Automated Pharmacy Admixture System," and filed by Eliuk et al. on Mar. 27, 2006 shows an example of a needle removal station. FIG. 59 in previously incorporated by reference U.S. patent application Ser. No. 11/389,995, entitled "Automated Pharmacy Admixture System," and filed by Eliuk et al. on Mar. 27, 2006 shows an example of a syringe capping station.

A syringe cap tray includes a plurality of syringe caps for placement on the luer of a syringe by the APAS. FIG. 57 of previously incorporated by reference U.S. patent application Ser. No. 11/389,995, entitled "Automated Pharmacy Admixture System," and filed by Eliuk et al. on Mar. 27, 2006 shows an example of a syringe cap tray. When the robotic arm in the APAS delivers an uncapped syringe to the syringe capping station, the APAS software controls the robotic arm so that the uncapped syringe does not pass over any of the other syringe caps to prevent any chance of drip cross contamination. The robotic arm selects available syringe caps from the outer edges of the syringe cap tray, or via some path that substantially avoids an approach to a syringe cap that passes over any other syringe cap on the way.

The possibility of small drips from a syringe occurs with and without a needle on the syringe. The APAS performs drip management to prevent cross contamination for syringes with and without needles. The possibility of small drips on the fluid transfer port of an IV bag occurs when injecting fluid into or drawing fluid from an IV bag. The APAS performs drip management to prevent cross contamination when handling IV bags.

Gripper fingers can be programmed to have a particular grip force to prevent fluid from being squeezed out of the syringe. The programmed gripper finger forces are different dependent on the size of the syringe and the action being performed. For example, the grip force for the syringe capping operation is higher than the grip force for the operation for picking up a syringe from a syringe scale.

When syringes are transported by the robotic arm within the APAS, the orientation of the syringe is selected so that the force of gravity and the acceleration and deceleration forces of transport acting on the fluid inside the syringe do not act to pull fluid from the needle or luer end of the syringe. This may substantially reduce or eliminate the occurrence of any drips from the needle and/or luer end of the syringe.

A syringe manipulator device employs a slurp function for drip management. FIGS. 6 and 7 in previously incorporated by reference U.S. patent application Ser. No. 11/937,846, entitled "Control of Fluid Transfer Operations," and filed by Doherty et al. on Nov. 9, 2007 show examples of a syringe manipulator device. The slurp function draws fluid out of the needle and into the luer lock hub of the syringe. With the fluid level contained substantially inside the syringe, the net effects of the compression forces generated by the gripper fingers, the force of gravity and the forces of transport are less likely to generate or liberate a drip at the end of the needle or luer lock hub.

The APAS manages drips using a drip catcher. A drip catcher is a suction device that includes a catcher or tray that is available on a syringe manipulator device where a syringe purges excess air, fluid or drips into the catcher. A drip catcher is also described with reference to FIGS. 33A and 33B. Syringes used to transfer diluent to a specific vial are used for the vial and the source diluent bag.

The APAS performs drip management to prevent cross contamination when using IV bags. The APAS controls the position and monitors the height of an IV bag port to control drips to prevent cross contamination. Examples of the control and management of IV bags are described in the previously incorporated by reference U.S. patent application Ser. No. 11/389,995, entitled "Automated Pharmacy Admixture System," and filed by Eliuk et al. on Mar. 27, 2006. The position of an IV bag port is tightly controlled in an inventory rack. Additionally, the APAS performs a second check on the position of the IV bag port by using a port height sensor included in a syringe manipulator device, an example of which is shown in FIG. 7 in previously incorporated by reference U.S. patent application Ser. No. 11/937,846, entitled "Control of Fluid Transfer Operations," and filed by Doherty et al. on Nov. 9, 2007. By controlling and monitoring the height of the IV bag port, the syringe manipulator device accurately controls the penetration of the needle of a syringe into the IV bag port. Accurate monitoring of the IV bag port height prevents the IV bag port from contacting the needle gripper included on the syringe manipulator device.

The syringe manipulator device controls the penetration of the needle of a syringe into the port of the IV bag. Slowly penetrating the port of an IV bag with the needle of a syringe on the syringe manipulator device enables the rubber portion of the IV bag port to flow past the needle. Slow retraction of the port of the IV bag from the needle prevents the creation of a vacuum or suction in the neck of the IV bag preventing the needle from creating drips on surfaces in the syringe manipulator device.

In some implementations, IV bag ports are covered or "taped" when inside the APAS. The covered IV bag ports contain the injection site and any fluid residue that may be present on the injection site on the port of the IV bag.

Release of Labeled Items from Gripper Fingers

Gripper devices include gripper fingers used to grasp and hold a vial while transferring it between stations in the APAS. The robotic arm 218 shown in FIG. 2 further includes gripper fingers in order to grasp, hold and transport a vial between stations in the APAS 100. The gripper fingers hold the vial while the APAS performs a particular operation. Examples of gripper devices and gripper fingers are described in previously incorporated by reference U.S. patent application Ser. No. 12/209,097, entitled "Gripper Device," and filed by Eliuk et al. on Sep. 11, 2008 and previously incorporated by reference U.S. patent application Ser. No. 11/389,995, entitled "Automated Pharmacy Admixture System," and filed by Eliuk et al. on Mar. 27, 2006.

Figure 45:
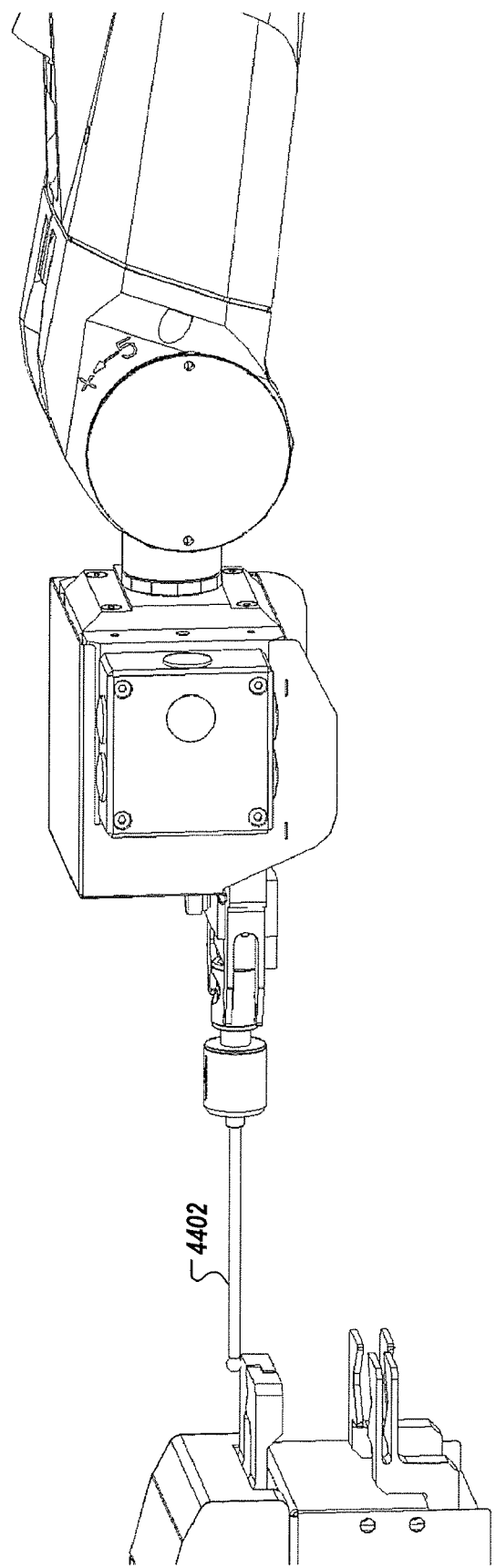
FIG. 45 is an illustration of an example touch probe teach tool in the process of autonomous point teaching.

A vial has an adhesive-backed label applied to the vial. The label includes information regarding the medicament contained in the vial (e.g., drug name, expiration date, bar code, etc.). FIG. 45 of previously incorporated by reference U.S. patent application Ser. No. 11/389,995, entitled "Automated Pharmacy Admixture System," and filed by Eliuk et al. on Mar. 27, 2006 shows an example of a vial that includes an adhesive-backed label. A robotic arm includes a set of gripper fingers for grasping the vial. When the robotic arm grasps a vial that includes an adhesive-backed label, a self-centering process occurs that allows the gripper fingers to grasp the vial substantially in the center of the label. When grasping the vial with the gripper fingers, the gripper fingers of the robotic arm may abraid the vial label. The abraiding of the label by the gripper fingers of the robotic arm causes a portion of the adhesive on the label to contact the gripper fingers. While transporting the vial within the APAS, the robotic arm grasps the vial at a first station and transports the vial to a second station. When the robotic arm places the vial at the second station, the gripper fingers open to release the vial, and the vial may remain lightly stuck to one of the gripper fingers. As the robotic arm retreats, the robotic arm may pull the vial along. This causes the vial to tip over during an upward motion or fall from the gripper fingers once the second station no longer provides support for the vial.

To correct for the partial sticking of a vial label to the gripper fingers upon release of the vial from the gripper fingers, when the robotic arm places the vial at the second station, the gripper fingers open less than a full open amount (e.g., approximately 1 mm). The robotic arm then moves down along the vial axis a distance (e.g., a few millimeters) in order to unstick the vial label from the gripper fingers (break any residual stiction between the gripper fingers and the vial label). The gripper fingers then continue to open to their full open amount. The robotic arm retreats from the station leaving the vial behind for further processing by the APAS.

Handling of IV Bag Differences

The APAS handles multiple sizes and brands of IV bags as described in previously incorporated by reference U.S. patent application Ser. No. 11/389,995, entitled "Automated Pharmacy Admixture System," and filed by Eliuk et al. on Mar. 27, 2006. The APAS is configured to use a specific brand or type of IV bag. Once configured for a brand or type of IV bag, the APAS handles all sizes of that brand or type of IV bag. In order for the APAS to handle and process all sizes of a particular type or brand of IV bag, the IV bag should exhibit consistent port geometry for the port of the IV bag over the full range of IV bag sizes.

A plurality of stations and devices in the APAS include IV bag specific interfaces in order to handle the plurality of IV bags configured for use in the APAS. Referring to FIG. 2, the stations and devices include, but are not limited to: robot gripper fingers (previously incorporated by reference U.S. patent application Ser. No. 11/389,995, entitled "Automated Pharmacy Admixture System," and filed by Eliuk et al. on Mar. 27, 2006 shows examples of robot gripper fingers); IV bag racks (e.g., racks 210 that can include IV bags); an IV bag scale (e.g., scale station 226); a port sanitization system (previously incorporated by reference U.S. patent application Ser. No. 11/389,995, entitled "Automated Pharmacy Admixture System," and filed by Eliuk et al. on Mar. 27, 2006 shows examples of port sanitization systems); a temporary bag storage location (e.g., IV bag parking location 800); a syringe manipulator device (e.g., needle-down syringe manipulator 234) and a container compressor (previously incorporated by reference U.S. patent application Ser. No. 12/271,828, entitled "Method And Apparatus For Automated Fluid Transfer Operations," and filed by Eliuk et al. on Nov. 14, 2008, shows examples of container compressors).

The APAS switches from using one brand or type of IV bag to another brand or type of IV bag with the use of a kit. A series of kits allow the conversion of the APAS to an IV bag type compatible with the needs of a particular customer or hospital.

In some implementations, the APAS uses an IV bag specific interface for some but not all IV bags used in the port sanitization system. The APAS uses a non-specific IV bag interface on a station or device for labeling an IV bag (e.g., bag labeler tray station 242), identifying an IV bag (e.g., output scanner station 230) and for outputting an IV bag (e.g., IV bag discharge chute 244). The non-specific bag interface may not require the use of a kit or other specific hardware changes when reconfiguring the APAS for use with a new brand or type of IV bag.

In some implementations, an operator places a clip or other type of attachment onto the port of the IV bag or onto the entire IV bag or a portion of the IV bag. The exterior of the attachments have standard features that interface with the stations and devices described. The clips allow the APAS to use different brands and types of IV bags concurrently as long as the appropriate clip or attachment is available to match the brand and type of IV bag.

The use of clips or attachments for IV bags that enable the APAS to use a plurality of brands and types of IV bags concurrently is convenient to design and implement. However, an operator has to install manually the clips or attachments on each IV bag before loading the IV bag onto the inventory racks. Additionally, the operator may have to remove the clip or attachment from the IV bag once the IV bag is dispensed from the APAS. Alternatively, the robotic arm may remove the clip or attachment prior to dispensing the IV bag from the APAS.

Additionally, the clips or attachments are sanitized prior to use, between uses, or on a schedule (if they are reusable). Alternatively, the attachments are disposable one-time use devices. The customer may determine the use of a one-time use attachment verses the use of a multi-use attachment based on cost (e.g., the cost of using the attachment once verses the cost of cleaning and reusing the attachment).

Printer Platen for Syringe Labeling

Figure 37A:
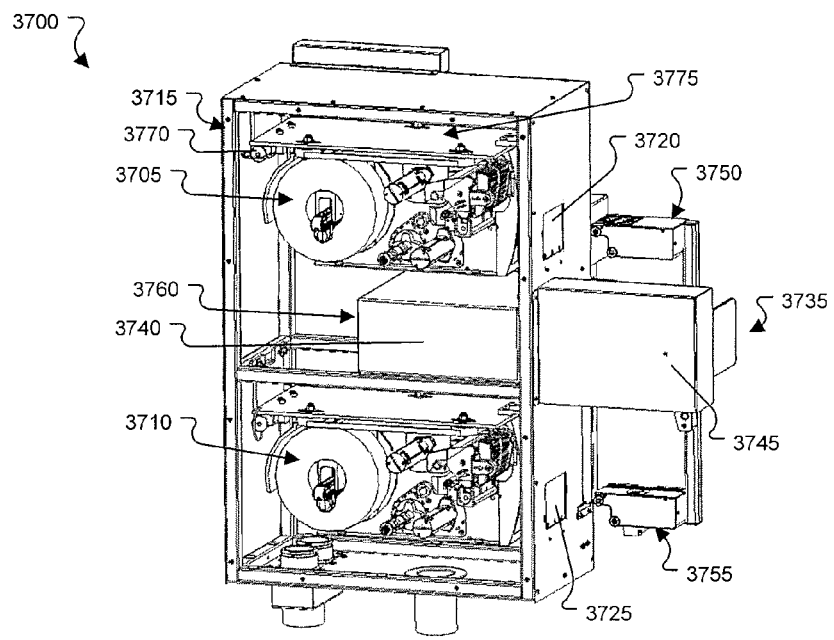
FIGS. 37A-37B show an illustrative printer system for an APAS.
Figure 37B:
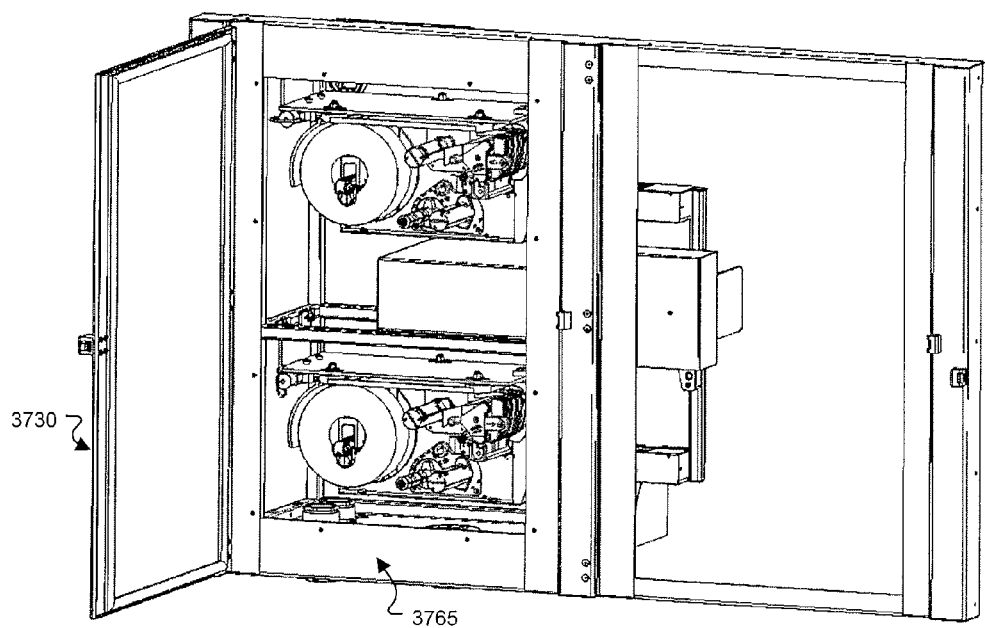
Figure 38:
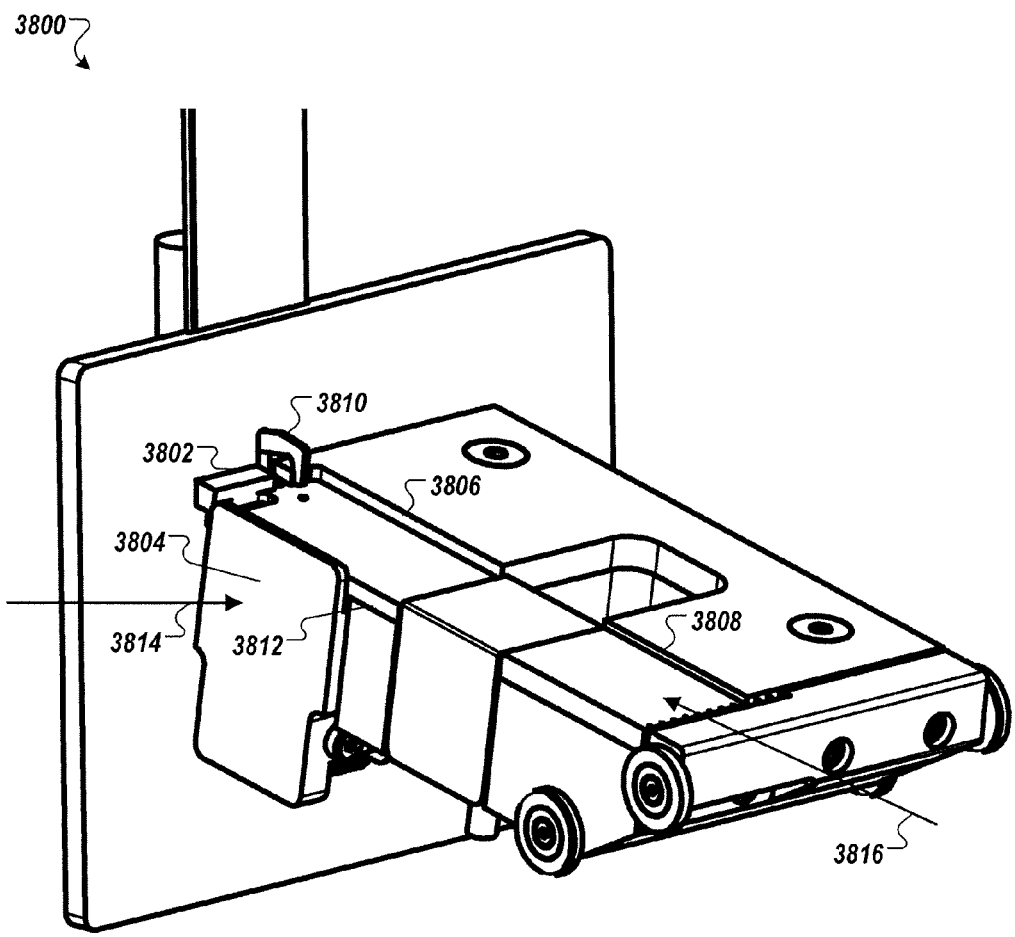
FIG. 38 is an illustration of a printer platen for labeling syringes in a printer system.

Referring to FIG. 2, the labeling station 228 includes one or more printers for printing labels for output containers (e.g., syringes, IV bags). The labeling station 228 interacts with the bag labeler tray station 242 where a label printed by a printer included in the labeling station is applied to an IV bag. FIGS. 37A-37B in previously incorporated by reference U.S. patent application Ser. No. 11/389,995, entitled "Automated Pharmacy Admixture System," and filed by Eliuk et al. on Mar. 27, 2006 show an example of a printer system for a labeling station (e.g., labeling station 228). FIG. 38 in previously incorporated by reference U.S. patent application Ser. No. 11/389,995, entitled "Automated Pharmacy Admixture System," and filed by Eliuk et al. on Mar. 27, 2006 shows an example of a label tray that may be a syringe label tray or an IV bag label tray.

FIGS. 37A-37B show an illustrative printer system 3700 for an APAS. The printer system 3700 includes printers 3705, 3710 mounted in an enclosure 3715 that includes an automated label shuttle 3735 that provides a pass through into the compounding area. The printer system 3700 includes a printer mounting plate 3775 that includes a quick release pin 3770 that enables the easy removal of the printer mounting plate 3775 assembly. The enclosure 3715 includes an external door 3730 for an operator to access the printers 3705 and 3710 for loading media and servicing. The printer enclosure 3715 is sealed against a panel 3765 that is located inside of the external door 3730 and mounted to the doorframe. The panel 3765 seals the inside of the APAS from the ambient environment when the operator opens the external door 3730, for example, for printer maintenance.

The APAS controller operates the printer enclosure 3715 at a more negative pressure than the compounding area through a duct providing fluid communication from the interior of the printer housing to a low pressure point in the air handling system and/or active fans. The negative relative pressure may substantially reduce particulate generated by printer operations from migrating from the printer enclosure 3715 into the compounding area. FIGS. 31A-31B in previously incorporated by reference U.S. patent application Ser. No. 11/389, 995, entitled "Automated Pharmacy Admixture System," and filed by Eliuk et al. on Mar. 27, 2006 show an air handling system in an APAS.

The printer system 3700 includes a set of spring-loaded printer housing doors 3720 and 3725 that open into the enclosure 3715 to receive label trays on the automated label shuttle 3735 from the compounding area. The shuttle 3735 includes a slide motor 3740, a slide cover 3745, a slide motor housing 3760, a bag label tray 3750 and a syringe label tray 3755. The shuttle 3735 pushes the pass-through doors 3720 and 3725 open to enter and capture the printed labels for presentation to a syringe or an IV bag for label application.

FIG. 38 is an illustration of a printer platen 3800 (label tray) for labeling syringes in a printer system (e.g., printer system 3700). The printer platen 3800 improves label application on syringes, the placement of the label on the syringe and the reliability of the initial label adhesion for transfer from the printer platen 3800 to the syringe.

As described with reference to FIGS. 37A-37B, a separate printer enclosure 3715 includes the printer system 3700. Housing printers 3705, 3710 in a separate enclosure 3715 prevents printer-generated contamination of critical processes in the compounding area. The printer platen 3800 is located adjacent to the printer enclosure (e.g., labeling station 228 and bag labeler tray station 242).

Figure 39:
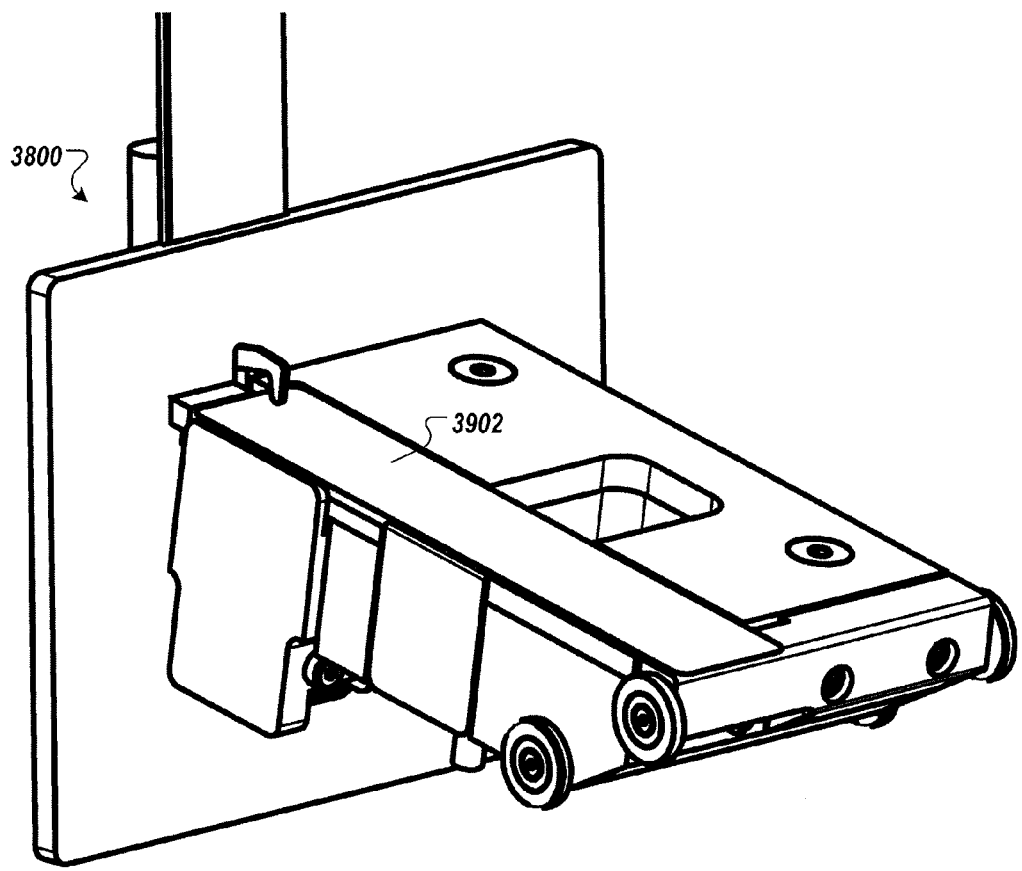
FIG. 39 is an illustration of a printer platen for labeling syringes in a printer system that shows a label.

FIG. 39 is an illustration of the printer platen 3800 for labeling syringes in a printer system (e.g., printer system 3700) that shows a label 3902. The label 3902 is shown with its adhesive side facing up. Referring to FIGS. 38 and 39, the printer platen 3800 moves into the printer enclosure 3715 where a printer feeds the label 3902 coming out of the printer onto the platen 3800 in the direction shown by arrow 3816.

The label 3902 engages an end stop 3802 on the printer platen 3800 as the label 3902 is fed out of the printer and approaches a limit of travel. A lateral actuator 3804, moving in the direction indicated by arrow 3814, pushes the label 3902 against side stops 3806, 3808 that run along the side of the label 3902 to register laterally the label 3902 (register the label 3902 from side to side). However, the edges of the label 3902 should not contact the side stops 3806, 3808 during label feed. The contact should not occur because adhesive on the label 3902 may cause a label edge to stick to anything it touches. Therefore, lateral label registration can occur after the printer fully feeds the label 3902 out of the printer.

To ensure the label 3902 remains registered in place on the printer platen 3800 during movement of the printer platen 3800, a label restraint finger 3810 pushes down on the adhesive side of the label 3902 to pinch the label 3902 in place on the printer platen 3800. The pushing down of the restraint finger 3810 on the adhesive side of the label 3902 ensures that any residual sticking of the label 3902 to backing paper that it was peeled from will not occur. Additionally, the pushing down of the restraint finger 3810 on the adhesive side of the label 3902 ensures that air currents in the APAS cannot disturb the label 3902 on the printer platen 3800 as it moves out of the printer enclosure 3715 for presentation to a syringe.

After positioning and securing the label 3902 on the printer platen 3800, the printer platen 3800 moves out of the printer enclosure 3715 with the label 3902 affixed to the printer platen 3800, bringing the label 3902 into the compounding area.

Figure 40:
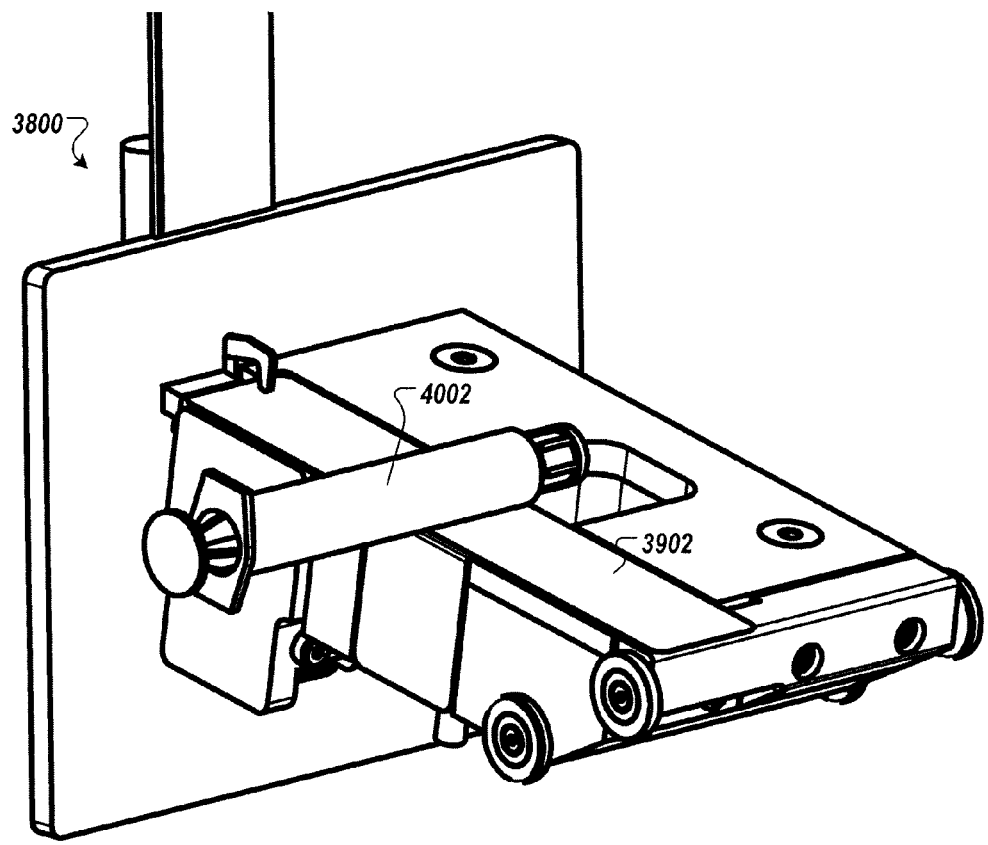
FIG. 40 is an illustration of a printer platen for labeling syringes in a printer system that shows a label and a syringe for labeling.

FIG. 40 is an illustration of the printer platen 3800 for labeling syringes in a printer system (e.g., printer system 3700) that shows a label 3902 and a syringe 4002 for labeling. For example, a robotic arm that includes gripper fingers to hold a syringe presents the syringe 4002 to the printer platen 3800. The robotic arm presents the syringe 4002 with the axis of the syringe perpendicular to the long dimension of the label 3902 and at the mid point of the length along the long dimension of the label 3902, and parallel to the plane of the label 3902. The syringe 4002 touches the surface of the label 3902 in order to stick the label 3902 to the syringe 4002 in an initial line of contact. The printer platen 3800 includes a compliant area, in a compliant platen section 3812, beneath the location on the printer platen 3800 where the syringe 4002 pushes down on the label 3902. Additionally, the syringe 4002 pushes down on the label 3902 to a level of approximately one millimeter below the initial contact of the syringe 4002 and the label adhesive.

The restraint finger 3810 and the lateral actuator 3804 are released. The robotic arm pushes the syringe down by an additional approximate four to five millimeters. The additional pushing down of the syringe 4002 results in further deflection of the compliant platen section 3812.

Improvement in the repeatability of the placement of the label 3902 on the printer platen 3800 by a label printer (e.g., printers 3705, 3710) improves the repeatability of the placement of the label 3902 on the syringe 4002. The use of the lateral actuator 3804 to register laterally the label 3902, and the restraint finger 3810 to secure the label in place until the syringe has initially contacted the label 3902 improves label placement repeatability. Additionally, the compliant platen section 3812 improves initial contact and affixing of the label 3902 to the syringe 4002. The lateral actuator 3804 registers the label 3902 in a repeatable manner from side to side. The lateral actuator 3804 fully constrains the label so that the presentation of the label 3902 to the syringe 4002 is repeatable. An electronic device moves the lateral actuator 3804. Alternatively, the printer platen 3800 uses an electric solenoid to move the lateral actuator 3804.

The pressing down of the syringe 4002 by the robotic arm in the compliant platen section 3812 improves the reliability of the initial adhesion of the label 3902 to the syringe 4002. The use of a rigid platen section enables the robotic arm holding a nominal-diameter syringe to touch the syringe lightly to the adhesive side of the label. In some cases, a smaller-than-nominal-diameter syringe may fail to make contact with the adhesive side of the label resulting in a label pickup failure. In some cases, a larger-than-nominal-diameter syringe may fail to make contact with the adhesive side of the label resulting in a label pickup failure. The larger-than-nominal-diameter syringe may erroneously contact the edge of the printer platen. This contact may pitch up the syringe not allowing the syringe to make adequate contact with the adhesive side of the label.

The incorporation of the compliant platen section 3812 in a printer platen 3800 improves the syringe to label contact for all diameter syringes. The compliant platen section 3812 is a spring actuated rigid section in the printer platen 3800. Alternatively, the compliant platen section 3812 is a thick foam pad, a pneumatic cushion, or a pneumatic actuated rigid section.

Manual and Autonomous Robot Teaching of Interfaces

As described with reference to FIG. 2, the processing chamber 204 includes a multiple degree of freedom robotic arm (robot) 218. For example, the robotic arm 218 includes gripper fingers that can pick items from a pocket on an inventory rack or that can grasp items within the APAS for manipulation. The robotic arm 218 responds to command signals from a controller to pick up, manipulate, or reposition inventory items within the processing chamber 204, and in or around the carousels 210, 212.

Figure 41:
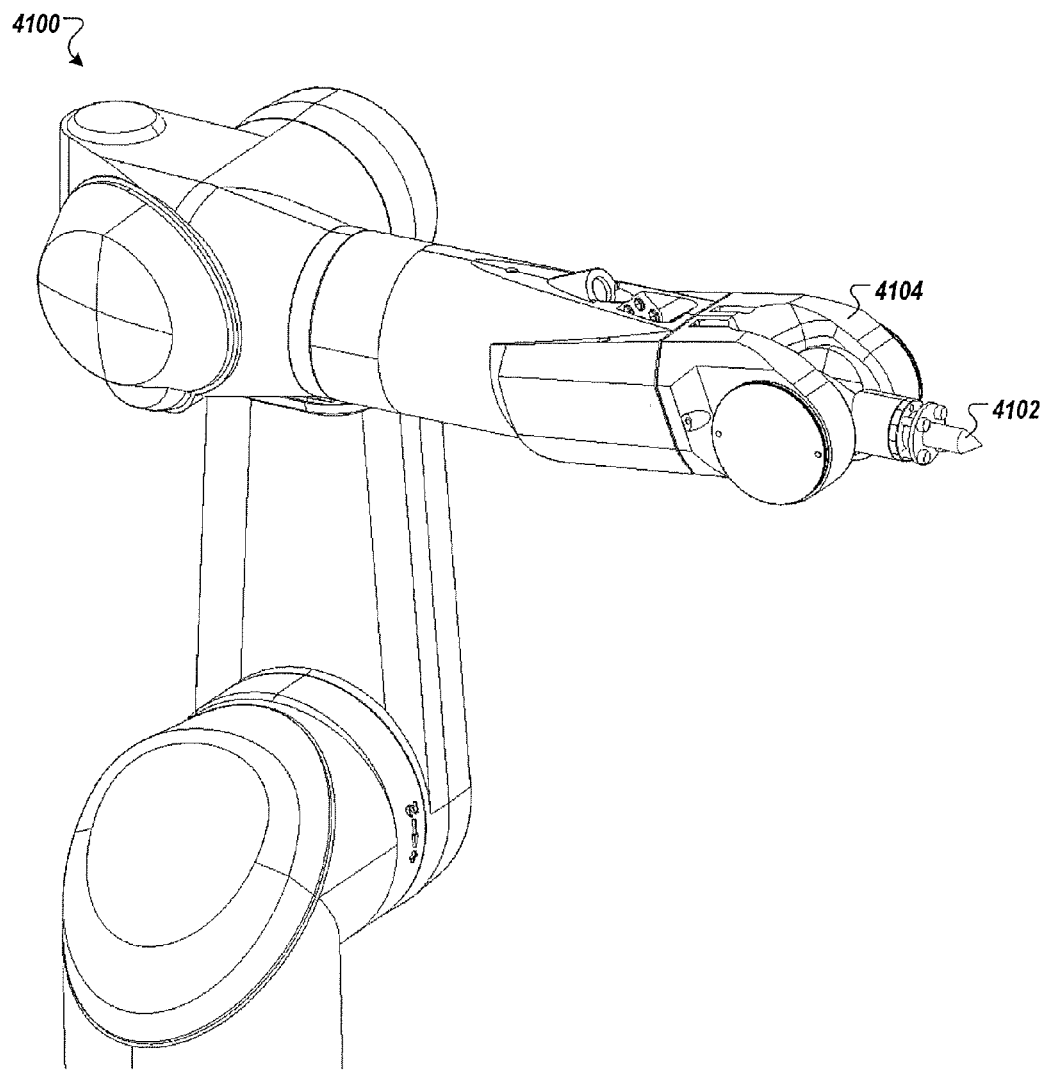
FIG. 41 is an illustration of an example robot that includes a Z pointer direct mounted teach tool.

FIG. 41 is an illustration of an example robot (robotic arm) 4100 that includes a Z pointer direct mounted teach tool 4102. The APAS 100 can use the robot 4100. In order to safely and reliably operate the APAS, tight control of the robot 4100 and its interfaces and the interfaces of any other moving and interacting components within the APAS are required. In general, repeatability within the domain of a robot coordinate system may be higher than the absolute accuracy of the robot over its working sphere. Therefore, robots are "taught" where interfaces are, and the robots then return to the location of the taught interfaces with high accuracy.

Direct taught points in a local coordinate reference frame represent the location of the interfaces. A series of three taught points defines a reference frame for the robot 4100. The robot 4100 can work accurately within the referenced frame. The APAS controller commands the robot 4100 to move to various features in the APAS with known geometry. The APAS controller commands the robot 4100 to move to computed or measured positions relative to the robot 4100. The direct teaching of points within the reference frame for the robot 4100 for critical interfaces improves the accuracy of the robot 4100 within the APAS. In some implementations, the series of taught points includes a number of points more than or less than three.

Manual robot controls and manual measurements can be used for teaching robot points. A robot flange 4104 is equipped with one or more teach tools (e.g., teach tool 4102) mounted directly to a robot flange interface.

Figure 42:
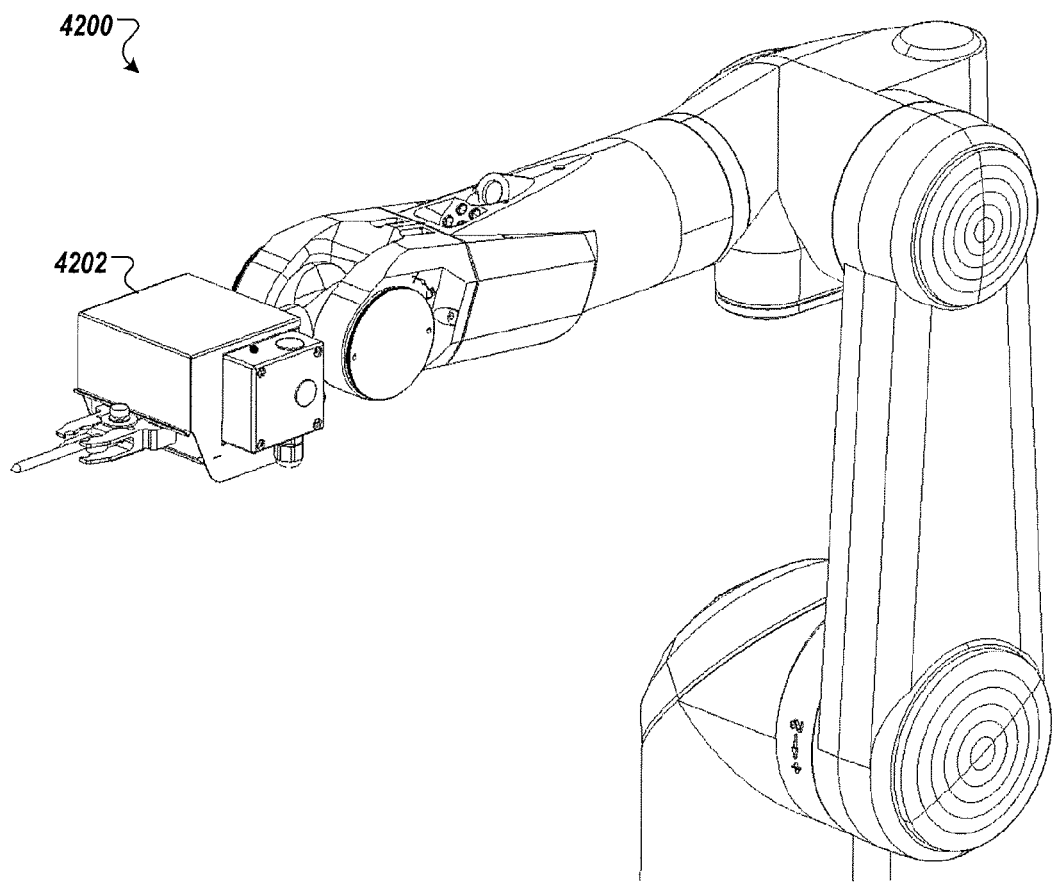
FIG. 42 is an illustration of an example robot that includes a straight pointer teach tool.
Figure 43:
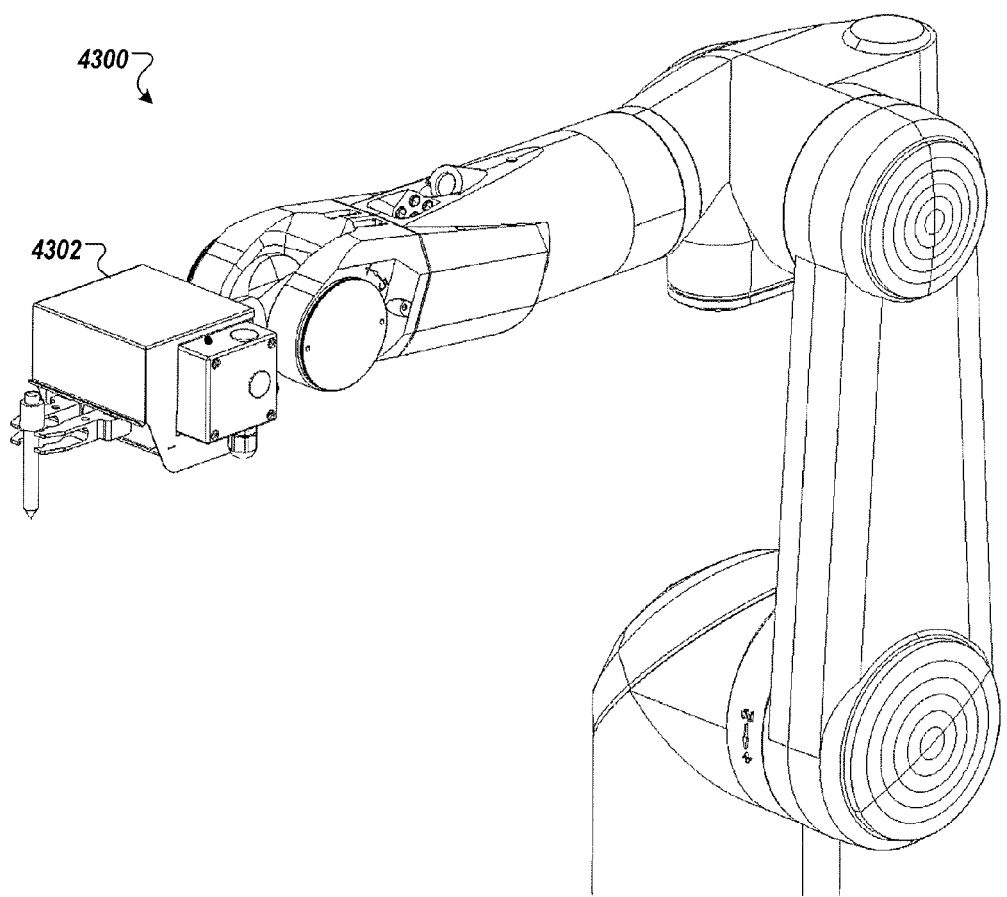
FIG. 43 is an illustration of an example robot that includes an offset pointer teaching tool.

FIG. 42 is an illustration of an example robot (robotic arm) 4200 that includes a straight pointer teach tool 4202. FIG. 43 is an illustration of an example robot (robotic arm) 4300 that includes an offset pointer teaching tool 4302. The robot flange 4104 is equipped with a gripper. The gripper grasps the teach tool. FIG. 42 shows an example of a straight pointer teach tool 4202 held by a robot gripper. FIG. 43 shows an example of an offset pointer teach tool 4302 held by a robot gripper.

The relationship of the teach tool to the end of the robot is geometric. The relationship of the teach tool to the end of the robot is taught through direct measurement. The relationship of the teach tool to the end of the robot is taught through measurements and statistical techniques that are based on one or more fixed data points in the APAS or on the robot.

In a manual teaching process, the operator manually guides the robot to the taught reference point using a robot teach pendant and the assistance of software controls. At the appropriate taught reference point, the operator enters that "here" (the location pointed to (touched) by the end of the robot (the teach tool)) is where the taught reference point is. The taught reference point (measurement data) can be saved in a robot controller. Alternatively, the taught reference point is transferred manually or autonomously to the APAS control computer. Alternatively, the taught reference point is saved in both the robot controller and the APAS control computer.

The process for teaching a reference frame is the same as the process for teaching reference points. In the case of reference frame teaching, the process uses three points as reference frame points. The process calculates the reference frame and saves the reference frame. Alternatively, the process saves the reference frame as a series of reference points where the process calculates the reference frame at run time.

Manual teaching can be slow, laborious and error prone and can require a relatively high level of operator skill. Additionally, manual teaching can require visual access to teach points, which may be difficult to achieve. Additionally, manual teaching can discourage routine teach point checking, which can be a significant aid to reliable operation.

Autonomous teaching is used to teach robot points. The concept of autonomous teaching is to equip the robot with the devices needed to allow the robot itself to determine its own interface relationships. This enables the robot to determine and update its interface relationships with a minimum amount of manual setup and intervention.

Figure 44:
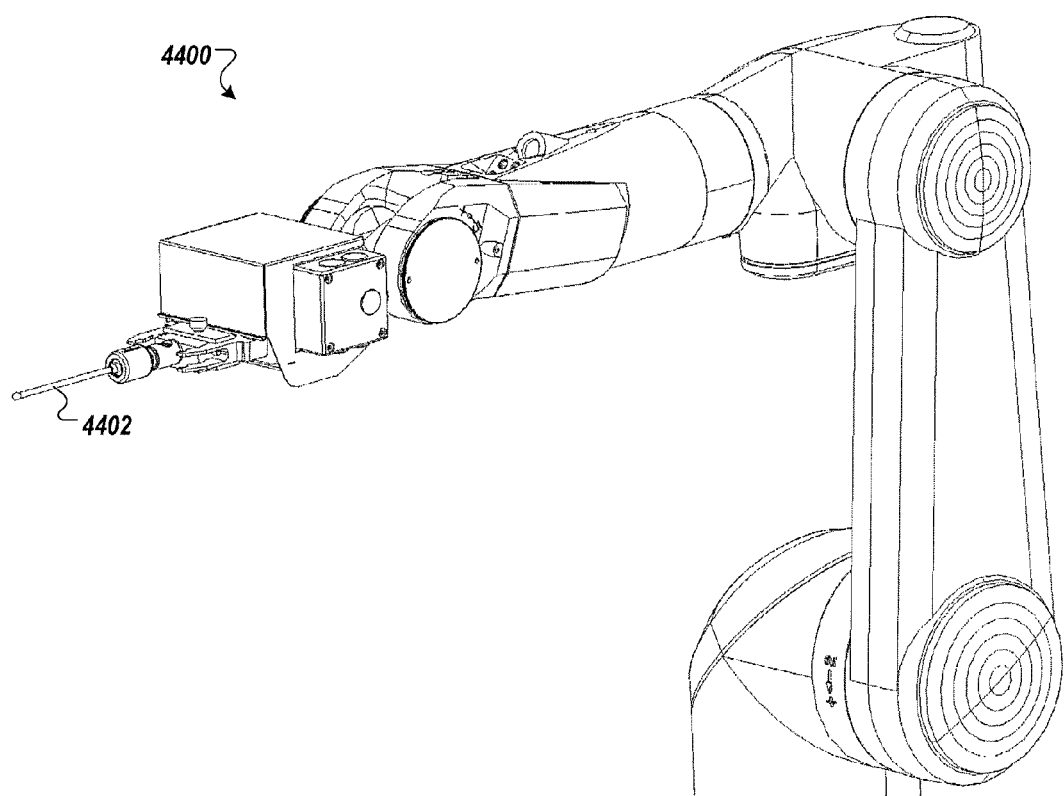
FIG. 44 is an illustration of an example robot that is a wielding touch probe teach tool.

FIG. 44 is an illustration of an example robot (robotic arm) 4400 that includes a wielding touch probe teach tool 4402. The robot utilizes an attached sensor in autonomous teaching. For example, the sensor is an analog or digital sensor and operates by touch or electro-optics. FIG. 44 shows an example wielding touch probe teach tool 4402 that includes a sensor. The robot gripper grasps the touch probe teach tool 4402 and uses it for teaching. The touch probe teach tool 4402 is handed off by the operator for the robot to grasp. The touch probe teach tool 4402 is picked up by the robot autonomously in the APAS. The touch probe teach tool 4402 is directly wired to the APAS or robot. Alternatively, the touch probe teach tool 4402 operates wirelessly using, for example, an optical, radio frequency (RF), or other type of wireless connection. The robot 4400 picks up the touch probe teach tool 4402 with no change in its operating configuration. This enables the robot 4400 to transition to and from a teaching configuration quickly and with minimal effort.

After the robot 4400 picks up the touch probe teach tool 4402, the APAS performs a self-check operation on the touch probe teach tool 4402. The APAS re-teachs or verifies the touch probe teach tool 4402 relative to the robot mounting flange. The APAS performs the verification using a fixed hard point that is invariant relative to the robot and measured autonomously or re-taught with the touch probe teach tool 4402.

FIG. 45 is an illustration of the touch probe teach tool 4402 in the process of autonomous point teaching. The touch probe teach tool 4402 finds, touches and teaches key points in the APAS. The APAS teaches reference points directly in a nominal "world" frame for the robot, or, in most cases, the APAS determines a reference frame to use in interfacing to a subsystem or group of points in the APAS.

In some implementations, the APAS uses techniques that allow the touch probe teach tool 4402 to safely maneuver and feel its way around the reference points to teach. In some cases, the reference points may be considerably off nominal. For example, points in a new APAS for initialization with a set of "nominal" initial points will initially include points that are significantly off nominal.

The APAS control software uses a plurality of algorithms to teach a reference frame and reference points. The touch probe teach tool 4402 iteratively feels out each of the points associated with a reference frame. The APAS control software renders the reference frame and uses the reference frame for a second refinement of the frame points. The APAS control software uses an algorithm that involves determining two lines to find a plane. Taught points may not be real corners or identifiable physical points. Taught points are a combination of any surface ordinates that relate to the reference frame in a repeatable way and form a "virtual" point.

The APAS uses a variety of touch probes as teaching tools where the touch probes vary in sensitivity and accuracy. The APAS uses touch probes with different touch probe end (staff) lengths and ball sizes. The APAS uses a touch probe with a longer staff to increase probe reach and sensitivity, however the touch probe with the longer staff can reduce probe accuracy. The APAS may use a touch probe with a shorter staff in order to increase probe accuracy.

The use of a touch probe for autonomous teaching in an APAS can be beneficial. The APAS uses the touch probe on relatively flexible structures (e.g., syringe scale station 226 in FIG. 2) that may be difficult to reach and teach. The APAS controller uses different robot motion speeds for a teaching process. For example, slower robot speeds may increase accuracy. The APAS controller may use higher robot speeds in order to save time.

Typical touch probe repeatability can be in the range of one micrometer. The APAS uses touch probes whose repeatability can be one, ten or one hundred micrometers. One or more interface relationships between the robot and a subsystem in the APAS requires teaching to the order of 100 micrometers, which is within the repeatability of the touch probe. Additional interface relationships between the robot and a subsystem in the APAS may be less critical and require teaching to the order of 200 micrometers.

The APAS uses the robot 4400 with the touch probe teach tool 4402 to enable the robot itself to determine and update its interface relationships. Additionally, the APAS uses the robot 4400 with the touch probe teach tool 4402 in a local reference frame as a measuring device to teach interface relationships between other items in the APAS. In some implementations, the robot 4400 with the touch probe teach tool 4402 is a coordinate-measuring machine (CMM) device that measures the physical geometrical characteristics of an object. For example, the robot 4400 with the touch probe teach tool 4402 teaches the height relationship of the vial fingers on the syringe manipulator device to the vial scale platen. The APAS uses this relationship to control the robot when dropping off a vial on the vial scale platen. In another example, the robot 4400 with the touch probe teach tool 4402 teaches the dimensions on the syringe manipulator device between the syringe needle gripper and the syringe plunger gripper at a known position for needle tip control. FIG. 52A in previously incorporated by reference U.S. patent application Ser. No. 11/389,995, entitled "Automated Pharmacy Admixture System," and filed by Eliuk et al. on Mar. 27, 2006 shows a syringe manipulator device.

In some implementations, alternative types of sensor probes, such as a beam sensor or a laser range sensor, are affixed to the end of the robot. A sensor is mounted on a subsystem or interface point and the robot includes gripper fingers. The sensor locates the robot gripper fingers and determines the interface of the robot to the subsystem or interface point that includes the sensor. A touch probe sensor may be permanently mounted to an APAS subsystem frame of interest to perform the teaching in order to check the integrity of the robot gripper fingers.

In some implementations, teach tools (teach sensors) include multiple tools in a set where a tool in the set can be autonomously selectable by the robot. The teach tools in a set are located in a fixed or rotating station. The robot that includes gripper fingers selects a tool in the set by grabbing the tool from the fixed or rotating station. Additionally, the teach tools (teach sensors) can include multiple tools in one or more tool sets where a tool set is autonomously selectable by the robot. The robot grabs a set of tools selected by a rotating or other indexer that is autonomously controlled and utilized by the robot. The robot grabbing a set of tools at one time may speed tool switching.

In some implementations, robot interfaces are taught without the use of a sensor or teach tool. The robot contacts or pushes against a subsystem with its flange or gripper fingers. The APAS controller detects the contact of the robot with the subsystem by monitoring the control loop deviation in the robot arm or by monitoring the increase in selective joint currents in the robot arm. For example, an APAS subsystem includes a sensor (e.g., a strain gauge, a beam) to detect the contact or push of the robot against it. In this case, the robot or gripper fingers may not include a sensor. In another example, the APAS uses the robot as a signal-circuit ground. The APAS subsystem can electrically detect the metallic contact of the robot to determine one or more teach points.

In some implementations, the APAS uses vision techniques for autonomous teaching of the robot. For example, a camera mounted on the robot locates subsystem features. The APAS controller uses the location of the subsystem features to teach points or to refine teach points. In another example, a camera on a subsystem is used to teach robot or other interface positions. The robot gripper fingers include fiducial marks that enable the gripper fingers to be located in the field of view of a camera included a syringe capper station. The APAS controller uses this information to refine the robot position in the field of view of the camera to increase the accuracy of syringe capping. FIGS. 57-62 of previously incorporated by reference U.S. patent application Ser. No. 11/389,995, entitled "Automated Pharmacy Admixture System," and filed by Eliuk et al. on Mar. 27, 2006 show a syringe capping station.

A plurality of different controllers can control the teaching protocol used by the APAS. The different controllers can include, but are not limited to, a robot controller, an APAS controller or an external computer interfacing to a database and controller in an APAS where the taught points are autonomously transferred to a database in the APAS.

The benefits of autonomous teaching can include, but are not limited to, reduced teaching time resulting in cost savings; reduced operation cell access requirements; reduced operator skill level and fatigue; improved accuracy and repeatability; and more frequent updates leading to longer term stability and reliability.

FIG. 46 is an example swimlane diagram showing a system 4600 for using an APAS. In the following example, a first user, a doctor, adds a first series of drug orders to an APAS, and a second series of orders, for use by the same doctor, are automatically generated and loaded to the APAS by a hospital's cancer treatment server. A second user prepares the APAS and commands the cell to process both series of drug orders.

During the evening, the hospital's cancer treatment server generates a list of known expected drugs for administration by the doctor to patients with appointments for the doctor that day. The server saves the list of known expected drugs as a first series of drug orders to an FTP server monitored 4604 by the APAS' network interface 4602. Due to a late change in scheduling, the doctor discovers additional drugs will be needed for a new patient. The doctor enters these new orders 4608 as a second series of drug orders via a remote user station's user interface 4606 associated with the APAS.

The APAS controller 4610 creates two queues 4612 of drug orders. A first queue contains the drug orders of the first series. The second queue contains the drug orders of the second series. The second queue is given a priority of "Stat" by the first user so that they will be processed first, and the drugs will be available first. The sequence number of drug orders within each queue is managed and sorted 4614 by the APAS controller 4610 in order to use hospital inventory as efficiently as possible.

A phantom queue is generated 4616 by the APAS controller 4610 and considered by the APAS, along with the first and second queue, for the purposes of determining inventory requirements. In this example, another doctor has required a third series of drug orders every day for the last week. The phantom queue is filled with the third series of drug orders.

After the three queues are prepared, a third user, an APAS operations technician, logs into the APAS. The third user is presented, via the user interface 4606, with the three queues, a list of inventory required to process the three queues, and a schematic diagram of APAS carousels and the inventory that is to be placed in each carousel position 4618. The third user reviews the orders, and loads the inventory 4622 into the carousel 4620 as described in the schematic.

The third user then commands the APAS to begin processing the real orders. The APAS cell 4624 begins processing the second queue 4626, which has the "Stat" priority, according to the sequence number of each drug order. During the processing of the second queue, the APAS can create an intermediary bag. To create the intermediary bag, a vial, IV bag, and syringe are retrieved by the APAS. The bag, having previously been drawn down to 100 ml, was located in a temporary parking area and retrieved using an end effector associated with the IV bag type. The syringe and vial, having been loaded by the second user, are located in the inventory carousel.

The syringe is decapped by the APAS. The IV bag is drawn down to 90 ml. The syringe draws 10 ml of fluid from the vial and inserts the fluid into the bag. To access the fluid in the vial, the syringe punctures the bung of the vial at or in close proximity to a previous puncture hole, if there is one. The syringe can be moved within the APAS in a path so as not to pass over any other equipment to substantially minimize the chance that any drops might fall on other surfaces in the APAS. A label identifying the drugs associated with the order is printed and applied to the syringe on a printer platen. The vial is weighed by the APAS and found to be lighter than expected. This weight discrepancy triggers a weight error by the APAS controller 4628.

To recover from the weight error, any finished and/or salvageable drugs are output or returned to inventory in the APAS. The syringe is recapped and disposed of 4632 in an APAS waste bin 4630 for holding syringes. The IV bag is disposed of 4632 in an APAS waste bin 4630 for holding IV bags. The vial is labeled as containing anomalous contents and output 4636 through an output chute 4634 as a reject. To release the vial into the output chute, gripper fingers holding the vial can open one mm and move down the vertical axis of the vial five mm to unstuck the vial label from the gripper fingers. The third user may determine if the vial should be disposed of or reclaimed for future use. Upon confirmation from the output chute that the vial has been removed, the drug order being processed when the weight error was detected is enqueued 4638 back into the second queue by the APAS controller 4610. The second queue is resorted, and the drug order moves to the head of the queue since it has the highest remaining sequence order. The APAS cell 4624 continues processing the second queue 4640 and outputs the resulting drugs.

A number of embodiments have been described. Nevertheless, it will be understood that various modifications may be made without departing from the spirit and scope. For example, advantageous results may be achieved if the steps of the disclosed techniques were performed in a different sequence, if components in the disclosed systems were combined in a different manner, or if the components were replaced or supplemented by other components. The functions and processes (including algorithms) may be performed in hardware, software, or a combination thereof. Accordingly, other embodiments are contemplated.

We claim:

1. A robotic automated pharmaceutical processing system comprising:
   a processor-based interface configured to receive requests to prepare one or more pharmaceutical prescriptions; and
   a controller coupled to the interface and configured to operate an automated prescription preparation device in response to the received requests, the automated prescription preparation device comprising:
     an inventory chamber comprising a housing to store within the inventory chamber a plurality of inventory items to be used in the preparation of one or more pharmaceutical prescriptions;
     an exterior access portal formed in a first side wall of the housing of the inventory chamber, wherein the exterior access portal is operable between a closed position and an open position to provide an operator access for loading and unloading inventory items in the inventory chamber;
     a compounding chamber access portal in a second side of the inventory chamber;
     a rotatable inventory carousel disposed in the inventory chamber to receive the plurality of inventory items, wherein the carousel is rotatable about a vertical axis and comprises a first plurality of locations each adapted to receive an IV bag, a second plurality of locations each adapted to receive a vial that contains a drug, and a third plurality of locations each adapted to receive a syringe configured with a plunger slidably disposed within a first end of a barrel and a needle coupled to a second opposite end of the barrel, and wherein the carousel is configured to bring a selected one of the locations in proximity to the compounding chamber access portal to present a selected inventory item being stored at the selected location to the compounding chamber access portal;
     a compounding chamber adjacent to the inventory chamber and communicating with the inventory chamber through the compounding chamber access portal in the second side, the second side being disposed between the compounding chamber and the inventory chamber;
     a multi-axis multi-linkage robot disposed within the compounding chamber and configured to grasp an inventory item being presented from the carousel in the inventory chamber to the compounding chamber access portal, convey the grasped inventory item to a first process location, release the inventory item for processing at the first process location, and subsequently convey the processed inventory item to a second process location in the compounding chamber;
     a syringe manipulator station configured to hold a syringe with a needle directed in a generally upward orientation for drawing fluid through the needle from a vial into the held syringe;
     a mixing station configured to impart a motion to the vial to mix the contents of the vial before the drawing of fluid from the vial;
     an air handling system arranged to provide air flow through the compounding chamber;
     a waste container area disposed in proximity to the compounding chamber to receive inventory items that have been processed in the compounding chamber; and
   wherein the controller is adapted to cause articulation of the stations to create an intermediary IV bag with a reconstituted drug at a predetermined intermediate concentration, draw a dose of intermediate concentration from the intermediary IV bag, and further dilute the drawn dose to prepare a final dose at a predetermined final dilution.

2. The system of claim 1, further comprising an aperture that couples the compounding chamber to the waste container area, wherein the air handling system is arranged to cause at least a portion of the provided air flow to flow from an interior region of the compounding chamber through the aperture generally toward a waste container disposed in the waste container area.

3. The system of claim 1, wherein the air handling system is further arranged to produce a substantially uniform airflow from a ceiling of the compounding chamber toward a floor of the compounding chamber.

4. The system of claim 1, wherein the air handling system is further arranged to reduce air pressure inside the compounding chamber to a level substantially below an ambient air pressure proximate and exterior to the compounding chamber.

5. The system of claim 1, wherein the controller is adapted to articulate one or more stations to determine the weight of an empty IV bag.

6. The system of claim 5, wherein the controller is adapted to determine the amount of diluent to remove to accommodate addition of a predetermined amount of medicament to produce a needed concentration level.

7. The system of claim 1, further comprising a vial seal puncturing controller to position successive needles for entry into the same vial puncture site.

8. The system of claim 7, wherein the vial seal puncturing controller determines based at least in part on needle type the needle engagement speed and disengagement speed to minimize leakage and coring.

9. The system of claim 7, wherein the vial seal puncturing controller modifies needle to vial engagement angles to enhance bung puncture performance.

10. The system of claim 7, wherein the vial seal puncturing controller modifies canting of the vial relative to needle bevel to enhance bung puncture performance.

11. The system of claim 7, wherein a needle used to puncture the vial is a pencil point needle that includes side ports.

12. The system of claim 7, wherein the vial seal puncturing controller adjusts needle penetration to maximize the amount of diluent that can be withdrawn from the vial.

13. The system of claim 1, wherein the controller manages batch mode production queues at least in part by assigning priority of drug orders in the queues.

14. The system of claim 13, wherein the controller executes software polling via FTP and selectively interrupts batch mode processing.

15. The system of claim 13, wherein the controller determines the queue in which a drug order belongs by priority sorting, drug type sorting, or location sorting.

16. The system of claim 13, wherein the controller combines a phantom queue for future processing with an existing first group of drug orders for current processing, resulting in a third group of drug orders for processing and entry into the system.

17. The system of claim 1, wherein the controller detects and recovers from errors by recovery of unused drugs, diluent and containers and re-queuing drug orders.

18. The system of claim 1, wherein the controller acquires through training or programming an actual amount of accessible fluid in a specific container, wherein the actual amount of fluid in a container is more than or less than the nominal amount of fluid in the container.

19. The system of claim 1, comprising separate waste containers for specific types of medical waste comprising sharps, glass, plastic, and cytotoxic, wherein the system sorts the types of medical waste into the various waste containers and wherein each waste container has associated level sensors.

20. The system of claim 1, further comprising sensors on output chutes to detect whether a completed product is output from the system and wherein the controller interrupts processing at least in selected circumstances wherein the sensor does not indicate the output of a completed product.

21. The system of claim 1, wherein the controller minimizes cross contamination by controlling gripper finger force, orientation of gripped syringe to minimize affect of acceleration forces, or use of slurp function to draw fluid out of needle and into luer lock of syringe.

22. The system of claim 1, wherein the system is configured to enhance the release of labeled vials from gripper fingers by abrasion of moving grippers along axis of vial after partial release of gripper fingers.

23. The system of claim 1, further comprising a kit to convert the system to use a specific type of IV bag, wherein the kit includes a disposable clip for attachment to an IV bag.

24. The system of claim 1, further comprising a syringe printer platen adapted to register a label, the platen having a compliant area for improved adhesion of the label to a syringe.

25. The system of claim 1, wherein the controller includes a training interface to teach the robot interface relationships including locations of system stations or subsystems.

26. The system of claim 25, wherein the robot retains a teaching tool used during training operations, wherein the tool is optionally an optical transducer.

* * * * *